United States Patent
Cloherty et al.

(10) Patent No.: US 12,235,273 B2
(45) Date of Patent: Feb. 25, 2025

(54) HBV DIAGNOSTIC, PROGNOSTIC, AND THERAPEUTIC METHODS AND PRODUCTS

(71) Applicant: Abbott Laboratories, Abbott Park, IL (US)

(72) Inventors: Gavin A. Cloherty, Abbott Park, IL (US); Mary Kuhns, Abbott Park, IL (US); Ka-Cheung Luk, Abbott Park, IL (US); Peter J. Karabatsos, Abbott Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 1031 days.

(21) Appl. No.: 17/052,685

(22) PCT Filed: May 3, 2019

(86) PCT No.: PCT/US2019/030738
§ 371 (c)(1),
(2) Date: Nov. 3, 2020

(87) PCT Pub. No.: WO2019/213619
PCT Pub. Date: Nov. 7, 2019

(65) Prior Publication Data
US 2021/0239700 A1 Aug. 5, 2021

Related U.S. Application Data

(60) Provisional application No. 62/689,963, filed on Jun. 26, 2018, provisional application No. 62/667,220, filed on May 4, 2018.

(51) Int. Cl.
*G01N 33/576* (2006.01)
*C12Q 1/48* (2006.01)
*C12Q 1/6837* (2018.01)

(52) U.S. Cl.
CPC .......... *G01N 33/5764* (2013.01); *C12Q 1/48* (2013.01); *C12Q 1/6837* (2013.01); *G01N 33/5762* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| | | | | |
|---|---|---|---|---|
| 5,659,023 A | * | 8/1997 | Alexander | .......... C07F 9/65616 |
| | | | | 435/6.12 |
| 2015/0192583 A1 | | 7/2015 | Klause et al. | |
| 2017/0152303 A1 | * | 6/2017 | Zhang | .................... A61K 45/06 |

FOREIGN PATENT DOCUMENTS

| | | |
|---|---|---|
| WO | 1997035204 A1 | 9/1997 |
| WO | 2001094559 A1 | 12/2001 |

OTHER PUBLICATIONS

Honer Zu Si Ederdissen Christoph et al: "What is new on HBsAg and other diagnostic markers in HBV infection?" Best Practice & Research. Clinical Gastroenterology Jun. 2017. vol. 31. No. 3. Jun. 1, 2017 (Jun. 2017). pp. 281-289. XP002792984.
Oliveri F et al: "Low viremic HBeAg negative HBsAg carriers: clinical outcome and non invasive diagnostic accuracy for chronic hepatitis B or inactive infection by combinations of HBV markers", Journal of Hepatology, vol. 66, No. 1, Jan. 1, 2017, XP085012470, ISSN: 0168-8278.
Ferruccio Bonino et al: "Diagnostic markers of chronic hepatitis B infection and disease", Antiviral Therapy—an Official Publication of the International Society for Antiviral Research, vol. 15, No. Suppl3, Jan. 1, 2010 (Jan. 1, 2010), pp. 35-44, XP055605696.
Ali Amini et al: "Diagnostic accuracy of tests to detect hepatitis B surface antigen: a systematic review of the literature and meta-analysis", BMC Infectious Diseases, Biomed Central Ltd, London, UK, vol. 17, No. 1, Nov. 1, 2017 (Nov. 1, 2017), pp. 19-37, XP021250341.
Ajay Kumar et al: "Significance of Alanine Aminotransferase Testing in Diagnosis of Acute and Chronic HBV Infection", Asian Pacific Journal of Cancer Prevention J Cancer Prev, vol. 10, No. 6, Jun. 1, 2009 (Jun. 1, 2009), pp. 1171-1172, XP055605893.
Li Jiancheng et al: "Development and Implementation of Autoverification Rules for ELISA Results of HBV Serological Markers". Journal of Laboratory Automation Oct. 2016, vol. 21, No. 5, Oct. 2016 (Oct. 2016), pp. 642-651, XP002792985.
International Searching Authority, International Search Report and Written Opinion for International Application No. PCT/US2019/030738 mailed Jul. 30, 2019.
International Searching Authority, International Preliminary Report on Patentability for International Application No. PCT/US2019/030738 mailed Nov. 19, 2020.

* cited by examiner

*Primary Examiner* — David W Berke-Schlessel
(74) *Attorney, Agent, or Firm* — Lisa Mueller; Casimir Jones SC

(57) ABSTRACT

Provided herein are compositions, systems, and methods for assessing and monitory disease stage and phases, predicting likelihood of disease progression, and predicting and monitoring responses to disease therapies (e.g., in HBV infection).

6 Claims, No Drawings

HBV DIAGNOSTIC, PROGNOSTIC, AND THERAPEUTIC METHODS AND PRODUCTS

CROSS-REFERENCE TO RELATED APPLICATIONS

This application is a national phase application under 35 U.S.C. § 371 of PCT International Application No. PCT/US2019/030738, filed May 3, 2019, which claims the benefit of U.S. Application No. 62/689,963, filed Jun. 26, 2019, and U.S. Application No. 62/667,220, filed May 4, 2018, each of which are herein incorporated by reference in its entirety.

FIELD

Provided herein are compositions, systems, and methods for assessing and monitoring disease stage and phases, predicting likelihood of disease progression, and predicting and monitoring responses to disease therapies (e.g., in HBV infection).

BACKGROUND

Hepatitis is a general term meaning 'inflammation of the liver' and has a number of causes. Viral causes are among the most common, and may be caused by hepatitis A, B, C, D or E virus. Hepatitis B virus (HBV), in particular, is a serious and common infectious disease of the liver, affecting millions of people throughout the world.

HBV is a hepatotrophic DNA virus belonging to the Hepadnaviridae. The full-length of the viral genome is about 3.2 kb, and it has four open reading frames (ORFs) including surface antigen (the "S gene"), core antigen (the "C gene"), DNA polymerase (the "P gene") and a gene of undetermined function referred to as the "X gene".

More than 2 billion people alive today have been infected with HBV at some time in their lives and of these about 350 million remain chronically infected and become carriers of the virus. HBV infection can cause acute and chronic type B hepatitis, and may eventually lead to the development of chronic hepatic insufficiency, cirrhosis, and hepatocellular carcinoma. In addition, HBV carriers can transmit the disease for many years.

HBV is transmitted by percutaneous or parenteral contact with infected bodily fluids or blood. The most common route of infection is via vertical transmission from mother to her baby, and in adults through sexual intercourse or shared intravenous needles or ear-piercing equipment. Many cases of acute HBV infection occur without a traceable route of infection.

Persons with chronic HBV infection ("carriers") have a 12-300 times higher risk of developing hepatocellular carcinoma than non-carriers and globally HBV causes 60-80% of the world's primary liver cancers. Every year about 25% of the over 4 million acute clinical cases die from chronic active hepatitis, cirrhosis or HBV-induced liver cancer. As a consequence, HBV ranks second only to tobacco as a known human carcinogen.

Although vaccines against HBV has been widely used for several decades, the HBV prevalence rate in the population still remains high. Current therapies for chronic HBV infection have only limited inhibitory effects on viral gene expression and replication in the majority of chronically infected patients. Lamivudine, for example, suppresses HBV replication in carriers, but the effect is reversible if therapy is stopped. Moreover, a major limitation of chronic Lamivudine therapy is the development of viral resistance, which typically develops after six months of treatment. Resistance is usually associated with mutations in the highly conserved catalytic region of the HBV polymerase gene.

For these reasons, there remains a need for new treatment courses of action and methods of selecting appropriate treatments for HBV infection.

SUMMARY

Provided herein are compositions, systems, and methods for assessing and monitory disease stage and phases, predicting likelihood of disease progression, and predicting and monitoring responses to disease therapies (e.g., in HBV infection).

The compositions and methods described herein provide improvements in quality of life and disease outcome by identifying optimum therapies and providing prognostic information to subjects and their health care providers.

For example, in some embodiments, provided herein is a method of assessing and monitoring disease stage or phase, predicting likelihood of disease progression, or predicting or monitoring response to a Hepatitis B (HBV) therapy (such as, for example, a HBV therapeutic), the method comprising the steps of; (a) contacting a test sample obtained from a subject being administered a treatment for HBV (such as, for example, a HBV therapeutic) or diagnosed with HBV with reagents for detection of the presence, level, or status of one or more markers selected from, for example, Hepatitis B e-antigen (HBeAg), Hepatitis B surface antigen (HBsAg), an isoform of HBsAg, Hepatitis B core antigen (HBcAg), HBV DNA (including one or more splice variants of HBV DNA), HBV RNA, Hepatitis B core-related antigen (HBcrAg), anti-Hepatitis B surface antigen antibody (anti-HBs), anti-Hepatitis B e-antigen antibody (anti-HBe), anti-Hepatitis B core antigen antibody (anti-HBc (e.g., IgM, IgG or both), complexes formed between HBsAg and anti-HBs (also referred to herein as "HBsAg immune complexes"), alanine aminotransferase (ALT), or aspartate aminotransferase (AST); and (b) assessing and monitoring disease stage or phase, predicting likelihood of disease progression, or predicting or monitoring response to a Hepatitis B (HBV) therapy based on the presence, level, or status of the one or more markers.

The above method can be repeated until the subject (i) has obtained HBsAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (ii) has obtained HBeAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iii) is negative for HBV DNA for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iv) demonstrates no evidence of liver injury based on ALT and/or AST levels for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; or (v) any combinations of (i)-(iv).

Further embodiments provide a method of detecting the presence, level, or status of one or more markers, comprising: (a) contacting a test sample obtained from a subject being administered a treatment for HBV (such as, for example, a HBV therapeutic) or diagnosed with HBV with reagents for detection of the presence, level, or status of one or more markers selected from, for example, Hepatitis B e-antigen (HBeAg), Hepatitis B surface antigen (HBsAg), an isoform of HBsAg, Hepatitis B core antigen (HBcAg), HBV DNA (including one or more splice variants of HBV DNA), HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), or aspartate aminotransferase (AST); and (b) determining the presence, level, or status of the one or more markers.

The above method can be repeated until the subject (i) has obtained HBsAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (ii) has obtained HBeAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iii) is negative for HBV DNA for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iv) demonstrates no evidence of liver injury based on ALT and/or AST levels for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; or (v) any combinations of (i)-(iv).

Additional embodiments provide a method of treating HBV, comprising: contacting a test sample obtained from a subject being administered a treatment for HBV (such as, for example, a HBV therapeutic) or diagnosed with HBV with reagents for detection of the presence, level, or status of one or more markers selected from, for example, Hepatitis B e-antigen (HBeAg), Hepatitis B surface antigen (HBsAg), an isoform of HBsAg, Hepatitis B core antigen (HBcAg), HBV DNA (including one or more splice variants of HBV DNA), HBV RNA, Hepatitis B core-related antigen (HBcrAg), anti-Hepatitis B surface antigen antibody (anti-HBs), anti-Hepatitis B e-antigen antibody (anti-HBe), complexes formed between HBsAg and anti-HBs (also referred to herein as "HBsAg immune complexes"), alanine aminotransferase (ALT), or aspartate aminotransferase (AST); (b) identifying a treatment for HBV based on the presence, level, or status of said one or more markers; and (c) administering the treatment (which can involve, for example, administering one or more HBV therapeutics).

In some embodiments, the treatment (e.g, the HBV therapeutic) is selected from, for example, interferon, a nucleos (t)ide analogue, a nucleic acid, an immunodulator, a core protein assembly inhibitor, an HBsAg release inhibitor, an entry inhibitor, or a combination thereof. In some embodiments, the interferon is interferon alpha-2a or PEGylated interferon alpha-2a. In some embodiments, the nucleos(t)ide analogue is, for example, lamivudine, adefovir, tenofovir, telbivudine, or entecavir. In some embodiments, the nucleic acid an siRNA, an antisense oligonucleotide, an shRNA, or a miRNA. In some embodiments, the core protein assembly inhibitor is NVR 3-1983, GLS4, or BAY 41-4109. In some embodiments, the HBsAg release inhibitor is REP 9 AC. In some embodiments, the entry inhibitor is Myrcludex-B. In some embodiments, the reagent is, for example, one or more of a plurality of nucleic acid primers that specifically hybridize to HBV DNA or RNA, a plurality of nucleic acid probes that specifically hybridize to HBV DNA or RNA, an antibody, antibody fragment, other immunoglobulin or other marker-specific binding molecule that specifically binds to an HBV protein, or reagents for enzymatic detection of ALT and/or AST. In some embodiments, the method further comprises altering treatment of HBV based on said presence, level, or status of the one or more markers. In some embodiments, the altering is starting, stopping, or changing the treatment. In some embodiments, the one or more markers comprises 2, 3, 4, 5, 6, 7, 8, 9, 10, or more markers. In some embodiments, the method is repeated one or more times (e.g., during treatment or monitoring of subjects). In some embodiments, the method is adapted for use in an automated system or semi-automated system.

Moreover, in some embodiments, the above treatment being administered to the subject is an individualized treatment regimen that is specific to that subject. The individualized treatment regimen can be designed or developed for the subject by a clinician (e.g., physician) based on clinical parameters, cutoffs, publications or a combination thereof. Additionally, the subject's treatment history to date can also be used in the design or development of the individualized treatment regimen.

Moreover, in some embodiments, the above treatment is being administered as part of one or more clinical trial(s) and comprises a treatment regimen designed or developed for one or more subjects based on clinical parameters, cutoffs, clinical parameters and cutoffs obtained from prior clinical trials, patient profiles, publications or a combination thereof. Additionally, the subject's treatment history to date can also be used in the design or development of the individualized treatment regimen.

The above method can be repeated until the subject (i) has obtained HBsAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (ii) has obtained HBeAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iii) is negative for HBV DNA for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iv) demonstrates no evidence of liver injury based on ALT and/or AST levels for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; or (v) any combinations of (i)-(iv).

Yet other embodiments provide a kit or system, comprising: reagents for detection of the presence, level, or status of one or more markers selected from, for example, Hepatitis B e-antigen (HBeAg), Hepatitis B surface antigen (HBsAg), an isoform of HBsAg, Hepatitis B core antigen (HBcAg), HBV DNA (including one or more splice variants of HBV DNA), HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), or aspartate aminotransferase (AST). In some embodiments, the kit or system further comprises software and a processor for analyzing said presence, level, or status of said one or more markers and providing an assessment of disease stage or phase, a prediction of likelihood of disease progression, or a prediction of a response to a Hepatitis B (HBV) therapy.

Still further embodiments provide the use of reagents for detection of the presence, level, or status of one or more markers selected from, for example, Hepatitis B e-antigen (HBeAg), Hepatitis B surface antigen (HBsAg), an isoform of HBsAg, Hepatitis B core antigen (HBcAg), HBV DNA (including one or more splice variants of HBV DNA), HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), or aspartate aminotransferase (AST).

Embodiments of the present disclosure also include a method of assessing efficacy of treatment with a Hepatitis B virus (HBV) therapeutic in a subject suffering from a chronic HBV infection. In accordance with these embodiments, the method includes: (a) performing an assay on a sample obtained from the subject to detect or measure a level of at least one HBV antigen biomarker, at least one HBV genomic biomarker, or at least one HBV antigen marker and at least one HBV genomic biomarker; and (b) determining whether seroclearance has been achieved by comparing the level of the at least one HBV antigen biomarker, the at least one HBV genomic biomarker, or the at least one HBV antigen marker and the at least one HBV genomic biomarker to a predetermined or reference level of the at least one HBV antigen biomarker, the at least one HBV genomic biomarker, or the at least one HBV antigen marker and the at least one HBV genomic biomarker; wherein: (i) the treatment is determined not to be efficacious if the level of the at least one HBV antigen biomarker, the at least one HBV genomic biomarker, or the at least one HBV antigen marker and the at least one HBV genomic biomarker is unfavorable when compared to the predetermined or reference level of the at least one HBV antigen biomarker, the at least one HBV genomic biomarker, or the at least one HBV antigen marker and the at least one HBV genomic biomarker; or (ii) the treatment is determined to be efficacious if the level of the at least one HBV antigen biomarker, the at least one HBV genomic biomarker, or the at least one HBV antigen marker and the at least one HBV genomic biomarker is favorable when compared to the predetermined or reference level of the at least one HBV antigen biomarker, the at least one HBV genomic biomarker, or the at least one HBV antigen marker and the at least one HBV genomic biomarker.

Embodiments of the present disclosure also include a method of determining whether a subject suffering from a chronic Hepatitis B virus (HBV) infection will benefit from receiving treatment with an HBV therapeutic. In accordance with these embodiments, the method includes: (a) performing an assay on a sample obtained from the subject to detect or measure a level of at least one HBV antigen biomarker, at least one HBV genomic biomarker, or at least one HBV antigen marker and at least one HBV genomic biomarker; and (b) determining the likelihood of seroclearance by comparing the level of the at least one HBV antigen biomarker, the at least one HBV genomic biomarker, or the at least one HBV antigen marker and the at least one HBV genomic biomarker to a predetermined level of the at least one HBV antigen biomarker, the at least one HBV genomic biomarker, or the at least one HBV antigen marker and the at least one HBV genomic biomarker; wherein it is determined that: (i) the subject will not benefit from an HBV therapeutic if the level of the at least one HBV antigen biomarker, the at least one HBV genomic biomarker, or the at least one HBV antigen marker and the at least one HBV genomic biomarker is unfavorable when compared to the predetermined or reference level of the at least one HBV antigen biomarker, the at least one HBV genomic biomarker, or the at least one HBV antigen marker and the at least one HBV genomic biomarker; or (ii) the subject will benefit from an HBV therapeutic if the level of the at least one HBV antigen biomarker, the at least one HBV genomic biomarker, or the at least one HBV antigen marker and the at least one HBV genomic biomarker is favorable when compared to the predetermined or reference level of the at least one HBV antigen biomarker, the at least one HBV genomic biomarker, or the at least one HBV antigen marker and the at least one HBV genomic biomarker.

DETAILED DESCRIPTION

Provided herein are compositions, systems, and methods for assessing and monitory disease stage and phases, predicting likelihood of disease progression, and predicting and monitoring responses to disease therapies (e.g., in HBV infection).

The genome of HBV is made of circular DNA, but it is unusual because the DNA is not fully double-stranded. One end of the full-length strand is linked to the viral DNA polymerase. The genome is 3020-3320 nucleotides long (for the full-length strand) and 1700-2800 nucleotides long (for the short length-strand). The negative-sense, (non-coding), is complementary to the viral mRNA. The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. Non-coding bases are removed from the ends of the (−) sense strand and the ends are rejoined. There are four known genes encoded by the genome, called C, X, P, and S. The core protein is coded for by gene C (HBcAg), and its start codon is preceded by an upstream in-frame AUG start codon from which the pre-core protein is produced. HBeAg is produced by proteolytic processing of the pre-core protein. The DNA polymerase is encoded by gene P (Pol). Gene S is the gene that codes for the surface antigen (HBsAg). The HBsAg gene is one long open reading frame but contains three in frame start (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. Because of the small size of the genome, many of the open reading frames overlap. For example the S open reading frame overlaps with the Pol open reading frame, specifically, HBV nucleotide positions 155 to 832, coding 226 amino acids of the surface antigen, overlaps with the RT region, nucleotide positions 130 to 1161, of the Pol gene. Drug resistance is associate with mutations in the RT region.

The virus is divided into four major serotypes (adr, adw, ayr, ayw) based on antigenic epitopes presented on its envelope proteins, and into nine genotypes (A-I) according to overall nucleotide sequence variation of the genome. The genotypes have a distinct geographical distribution and are used in tracing the evolution and transmission of the virus. Differences between genotypes affect the disease severity, course and likelihood of complications, and response to treatment and vaccination. Genotypes differ by at least 8% of their sequence and were first reported in 1988 when six were initially described (A-F). Norder H, Courouce A M, Magnius L O (1994). "Complete genomes, phylogenic relatedness and structural proteins of six strains of the hepatitis B virus, four of which represent two new genotypes." Vinology 198 (2): 489-503; herein incorporated by reference in its entirety. Three further types have since been described (G, H, and I). Shibayama T, Masuda G, Ajisawa A, Hiruma K, Tsuda F, Nishizawa T, Takahashi M, Okamoto H (May 2005). "Characterization of seven genotypes (A to E, G and H) of hepatitis B virus recovered from Japanese patients infected with human immunodeficiency virus type 1." *Journal of Medical Virology* 76 (1): 24-32; herein incorporated by reference in its entirety. "A complex hepatitis B virus (X/C) recombinant is common in Long An county, Guangxi and may have originated in southern China." *Journal of General Virology* (2011), 92, 402-411; herein incorporated by reference in its entirety. Most genotypes are now divided into subgenotypes with distinct properties. Schaefer S (January 2007). "Hepatitis B virus taxonomy and hepatitis B virus genotypes." *World Journal of Gastroenterology: WJG* 13 (1): 14-21; herein incorporated by reference in its entirety.

HBV has a high degree of genetic variation with nine known genotypes (A-I). Different mutations in the various HBV genotypes are associated with how the virus can escape the immune system or become resistant to antiviral drugs. Ray, K, "Hepatitis: Genetic variability in HBV resistance." *Nature Reviews Gastroenterology and Hepatology* 8, 535 (October 2011).

Accordingly, biomarkers or markers (the terms "biomarkers" and "markers" are used interchangeably herein) described herein identify details such as genotype, serotype, virility, drug resistance, etc. of HBV present in a subject diagnosed with HBV. Such markers find use in providing a prognosis, determining and administering treatment, and monitory treatment.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Various embodiments of the methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As used herein, the term "algorithm" refers to a process or set of rules to be followed in calculations or other problem-solving operations (such as, for example, by one or more computers containing one or more software programs that analyze data from one or more markers and optionally, one or more biometric data (such as for example, history of intravenous drug use, chronic liver and/or kidney disease, employment history as a healthcare worker, age, gender, race, etc.), and includes the requisite code to execute the algorithm). For example, analysis of HBV marker data performed using an algorithm(s) can include analyzing: (1) single biomarkers (e.g, Hepatitis B e-antigen (HBeAg), Hepatitis B surface antigen (HBsAg), an isoform of HBsAg, Hepatitis B core antigen (HBcAg), HBV DNA (including one or more splice variants of HBV DNA), HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes") alanine aminotransferase (ALT) or aspartate aminotransferase (AST)); (2) single markers with one or more biometric data; (3) groups of single markers (e.g., Hepatitis B e-antigen (HBeAg), Hepatitis B surface antigen (HBsAg) an isoform of HBsAg, Hepatitis B core antigen (HBcAg), HBV DNA (including one or more splice variants of HBV DNA), HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), aspartate aminotransferase (AST) or combinations thereof); or (4) groups of single markers with one or more biometric data. Still further approaches can employ multiple analyte algorithms (such as described in U.S. Patent Publication no. 2016/0342757, herein incorporated by reference) rather than a single marker (with or without biometric data) or a group of single markers (with or without biometric data). Such algorithms can be used as part of the methods described herein to derive one or more values that reflect disease status, stage, or phase, to predict likelihood of disease progression, and/or predict or monitor response to therapy or treatment.

As used herein, the term "antibody" refers to an immunoglobulin molecule or immunologically active portion thereof, namely, an antigen-binding portion. Examples of immunologically active portions of immunoglobulin molecules include F(ab) and F(ab')$_2$ fragments which can be generated, e.g., by treating an antibody with an enzyme such as pepsin. Examples of antibodies that can be used in the present disclosure include, but are not limited to, polyclonal antibodies, monoclonal antibodies, chimeric antibodies, human antibodies, humanized antibodies, recombinant antibodies, single-chain Fvs ("scFv"), affinity matured antibodies, single chain antibodies, single domain antibodies, F(ab) fragments, F(ab') fragments, disulfide-linked Fvs ("sdFv"), and antiidiotypic ("anti-Id") antibodies, among others, and functionally active epitope-binding fragments of any of the above. The antibody may be of classes IgG, IgM, IgA, IgD or IgE, or fragments or derivatives thereof. The antibody may be derivatized by the attachment of one or more chemical, peptide, or polypeptide moieties known in the art. The antibody may be conjugated with a chemical moiety.

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The "area under curve" or "AUC" refers to area under a ROC curve. AUC under a ROC curve is a measure of accuracy. An AUC of 1 represents a perfect test, whereas an AUC of 0.5 represents an insignificant test. A preferred AUC may beat least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

A "receiver operating characteristic" curve or "ROC" curve refers to a graphical plot that illustrates the performance of a binary classifier system as its discrimination threshold is varied. For example, an ROC curve can be a plot of the true positive rate against the false positive rate for the different possible cutoff points of a diagnostic test. It is created by plotting the fraction of true positives out of the positives (TPR=true positive rate) vs. The fraction of false positives out of the negatives (FPR=false positive rate), at various threshold settings. TPR is also known as sensitivity, and FPR is one minus the specificity or true negative rate. The ROC curve demonstrates the tradeoff between sensitivity and specificity (any increase in sensitivity will be accompanied by a decrease in specificity); the closer the curve follows the left-hand border and then the top border of the ROC space, the more accurate the test; the closer the curve comes to the 45-degree diagonal of the ROC space, the less accurate the test; the slope of the tangent line at a cutoff point gives the likelihood ratio (LR) for that value of the test; and the area under the curve is a measure of test accuracy.

"Bead" and "particle" are used herein interchangeably and refer to a substantially spherical solid support. One example of a bead or particle is a microparticle. Microparticles that can be used herein can be any type known in the art. For example, the bead or particle can be a magnetic bead or magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeOfe_2O_3$). Beads can have a solid core portion that is magnetic and is surrounded by one or more non-magnetic layers. Alternately, the magnetic portion can be a layer around a non-magnetic core. The microparticles can be of any size that would work in the methods described herein, e.g., from about 0.75 to about 5 nm, or from about 1 to about 5 nm, or from about 1 to about 3 nm.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (also referred to as hybrid-hybridoma technology; see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Favorable" as used herein means in certain aspects that when the level(s) of one or more biomarkers measured and/or determined according to the methods described herein is compared to one or more reference levels is less than or lower than the reference level(s). However, in other aspects, depending on the biomarker(s) being measured or determined, the term "favorable" may mean that the level(s) of the one or more biomarkers measured and/or determined according to the methods described herein is higher or greater than the one or more reference levels. Whether a "favorable" level is higher or lower compared to the reference level depends on whether there is a rise or fall of the biomarker in the context of HBV infection. Generally, a favorable level of a biomarker is one that suggests an absence of HBV infection, improvement in a subject's health with respect to an HBV infection, or that a subject is likely to benefit from treatment (or continued treatment) with an HBV therapeutic. Methods for determining if the level(s) of one or more biomarkers measured and/or determined according to the methods described herein are favorable when compared to the reference level are well known in the art. For instance, one measure is clinical improvement of the subject which can be determined by any number of a variety of parameters (e.g., patient reports, improvement in skin color (e.g., less yellow or jaundice in color), a reduction in the amount of liver inflammation, etc.).

"Unfavorable" as used herein means in certain aspects that when the level(s) of one or more biomarkers measured and/or determined according to the methods described herein is compared to one or more reference levels is higher or greater than the reference level(s). However, in other aspects, depending on the biomarker(s) being measured or determined, the term "unfavorable" may mean that the level(s) of the one or more biomarkers measured and/or determined according to the methods described herein is less than or lower than the one or more reference levels. As described above, whether an "unfavorable" level is higher or lower compared to the reference level depends on whether there is a rise or fall of the biomarker in the context of HBV infection. Generally, an unfavorable level of a biomarker is one that suggests a presence of HBV infection, worsening of a subject's health with respect to an HBV infection, or that a subject is not likely to benefit from treatment (or continued treatment) with an HBV therapeutic. Methods for determining if the level(s) of one or more biomarkers measured and/or determined according to the methods described herein are unfavorable when compared to the reference level are well known in the art. For instance, one measure is a worsening of the condition of the subject which can be determined by any number of a variety of parameters (e.g., patient reports, a change or worsening of skin color (e.g., an increase in yellow or greater jaundice in color), increase in liver inflammation, etc.).

"Identical" or "identity" as used herein in the context of two or more polypeptide or polynucleotide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

"Isoform(s) of hepatitis surface antigen or HBsAg" or "hepatitis surface antigen or HBsAg isoform(s)" as used herein refers to one or more polypeptides encoded by the pre-S1, pre-S2 and/or S sections of the HBsAg gene which are referred to as large (L), middle (M) and small (S) HBs. Each of the large, middle and small HBs contain the S domain. The middle HBs protein (MHBs) has a 55-amino acid long N-terminal extension, the preS2 domain. The HBV large surface protein (LHBs) has an additional 108 or 119-amino acid N-terminal extension, the preS1 domain. The HBsAg of infectious virions and subviral particles consists predominantly of HBV small surface proteins (SHBs), with LHBs and MHBs as minor components. The isoforms contemplated herein can comprise the (i) large HBs only; (ii) the middle HBs only; (iii) the small HBs only (iv) the large HBs and middle HBs; (v) the large HBs and small HBs; (vi) the middle HBs and small HBs; or (vii) the large HBs, middle HBs and small HBs.

"Substantially identical," as used herein may mean that a first and second sequence are at least from about 50% to about 99% identical over a region of from about 8 to about 100 or more residues (including any range within from about 8 to about 100 residues).

As used herein, the term "test sample" or "sample" generally refers to a biological material being tested for and/or suspected of containing an analyte of interest, such as a marker described herein. The test sample may be derived from any biological source, such as, a physiological fluid, including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen and so forth. In some embodiments, the sample is a whole blood sample. In some embodiments, the sample is a plasma sample. In yet other embodiments, the sample is a serum sample. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

As used herein the term "target nucleotide sequence" refers to a molecule that includes the nucleotide sequence of a target nucleic acid (e.g., a nucleic acid to be detected in an assay), such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. i.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

The term "oligonucleotide" is used to refer to a nucleic acid that is relatively short, generally shorter than 200 nucleotides, shorter than 100 nucleotides, in some cases, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, and in some cases, once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-30 nucleotides in length).

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%, 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

"Amplification" encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other sources, Ausbel et al.; *PCR Primer: A Laboratory Manual*, Diffenbach, Ed., Cold Spring Harbor Press (1995); *The Electronic Protocol Book, Chang Bioscience* (2002); Msuih et al., J. Clin. Micro. 34:501-07 (1996); The Nucleic Acid Protocols Handbook, R Rapley, ed., Humana Press, Totowa, N.J. (2002); Abramson et al., *Curr Opin Biotechnol.* 1993 February; 4(1):41-7, U.S. Pat. Nos. 6,027,998; 6,605,451, Barany et al., PCT Publication No. WO 97/31256; Wenz et al., PCT Publication No. WO 01/92579: Day et al., Genomics, 29(1): 152-162 (1995), Ehrlich et al., *Science* 252:1643-50 (1991); Innis et al., PCR Protocols: A Guide to Methods and Applications, Academic Press (1990); Favis et al., *Nature Biotechnology* 18:561-64 (2000); and Rabenau et al., *Infection* 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, *Proc. Natl. Acad. Sci. USA* 88:188-93 (1991); Bi and Sambrook, *Nucl. Acids Res.* 25:2924-2951 (1997); Zirvi et al., *Nucl. Acid Res.* 27:e40i-viii (1999); Dean et al., *Proc Nat Acad Sci USA* 99:5261-66 (2002); Barany and Gelfand, Gene 109:1-11 (1991): Walker et al., *Nucl. Acid Res.* 20:1691-96 (1992); Polstra et al., BMC Inf. Dis. 2:18-(2002); Lage et al., *Genome Res.* 2003 February; 13(2):294-307, and Landegren et al., Science 241:1077-80 (1988), Demidov, V., *Expert Rev Mol Diagn.* 2002 November; 2(6):542-8, Cook et al., *J Microbiol Methods.* 2003 May; 53(2):165-74, Schweitzer et al., *Curr Opin Biotechnol.* 2001 February; 12(1):21-7, U.S. Pat. Nos. 5,830,711, 6,027,889, 5,686,243, PCT Publication No. WO0056927A3, and PCT Publication No. WO9803673A1.

"Reference level" as used herein refers to an assay or cutoff value that is used to assess diagnostic ("diagnostic" cutoff), prognostic, or therapeutic efficacy and that has been linked or is associated herein with various clinical parameters (e.g., presence of disease such as, for example, to rule a subject as having a disease ("rule in") or rule a subject as not having a disease ("rule out")), stage of disease, severity of disease, progression, non-progression, or improvement of disease, etc.) This disclosure provides exemplary reference levels. However, it is well-known that reference levels may vary depending on the nature of the immunoassay (e.g., such as, in an immunoassay, the antibodies employed, reaction conditions, sample purity, etc.) and that assays can be compared and standardized. It further is well within the ordinary skill of one in the art to adapt the disclosure herein for other assays to obtain assay-specific reference levels for those other immunoassays based on the description provided by this disclosure. Whereas the precise value of the reference level may vary between assays, the findings as described herein should be generally applicable and capable of being extrapolated to other assays.

As used herein the term "single molecule detection" refers to the detection and/or measurement of a single molecule of an analyte in a test sample at very low levels of concentration (such as pg/mL or femtogram/mL levels). A number of different single molecule analyzers or devices are known in the art and include nanopore and nanowell devices. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

A "reagent" refers broadly to any agent used in a reaction, other than the analyte (e.g., nucleic acid or polypeptide being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators. Reagents for immunoassay include, for example, antibodies specific for a target marker, detection (e.g., labeled) antibodies, controls, buffers, and the like.

The term "label," as used herein, refers to any atom or molecule that can be used to provide a detectable and/or quantifiable signal. In some cases, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

An "absolute amount" as used herein refers to the absolute value of a change or difference between at least two assay results taken or sampled at different time points and, which similar to a reference level, has been linked or is associated herein with various clinical parameters (e.g., presence of disease, stage of disease, severity of disease, progression, non-progression, or improvement of disease, etc.). "Absolute value" as used herein refers to the magnitude of a real number (such as, for example, the difference between two compared levels (such as levels taken at a first time point and levels taken at a second time point)) without regard to its sign, i.e., regardless of whether it is positive or negative.

This disclosure provides exemplary reference levels and absolute amounts (e.g., calculated by comparing reference levels at different time points). However, it is well-known that reference levels and absolute amounts may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels and absolute amounts for those other immunoassays based on the description provided by this disclosure. Whereas the precise value of the reference level and absolute amount may vary between assays, the findings as described herein should be generally applicable and capable of being extrapolated to other assays.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, whole blood, serum or plasma sample, in accordance with the methods described herein and other methods known in the art. Some components can be in solution or lyophilized for reconstitution for use in an assay.

"Controls" as used herein generally refers to a reagent whose purpose is to evaluate the performance of a measurement system in order to assure that it continues to produce results within permissible boundaries (e.g., boundaries ranging from measures appropriate for a research use assay on one end to analytic boundaries established by quality specifications for a commercial assay on the other end). To accomplish this, a control should be indicative of patient results and optionally should somehow assess the impact of error on the measurement (e.g., error due to reagent stability, calibrator variability, instrument variability, and the like).

"Correlated to" as used herein refers to compared to.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody may be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Hepatitis B core-related antigen (HBcrAg)" as used herein refers to the antigenic reactivity resulting from denatured hepatitis B e antigen (HBeAg). HBV core antigen (HBcAg) and an artificial core-related protein (p22cr).

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The acute phase of an HBV infection generally persists from about 4 weeks to about 6 months after infection, while the chronic phase of an HBV infection generally includes the period of time after the acute phase has ended. In some cases, treating or monitoring a chronic HBV infection includes performing an assay on a sample that was obtained from about 24 weeks after the subject was infected. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, including the side chains of those amino acids, as revealed by the hydrophobicity, hydrophilicity, charge, size, and other properties.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Markers

The present disclosure relates to assays for determining the presence, level, or status of one or more markers in a test sample obtained from a subject. Exemplary markers suitable for use in the compositions, systems, and methods described herein are described below.

Exemplary markers include, but are not limited to, Hepatitis B e-antigen (HBeAg), Hepatitis core antigen (HBcAg), Hepatitis B surface antigen (HBsAg), an isoform of HBsAg, HBV DNA (including one or more splice variants of HBV DNA), HBV RNA (e.g., HBV pregenomic RNA or pgRNA), Hepatitis B core-related antigen (HBcrAg), anti-Hepatitis B surface antigen antibody (anti-HBs), anti-Hepatitis B e-antigen antibody (anti-HBe), anti-Hepatitis surface antigen antibody (anti-HBs) complexes formed between HBsAg and anti-HBs (also referred to herein as "HBsAg immune complexes"), alanine aminotransferase (ALT), or aspartate aminotransferase (AST).

In some embodiments, 1, 2, 3, 4, 5, 6, 7, 8, 9, or 10 or more of the above described markers are detected. For example, in some embodiments, HBeAg and HBsAg; HBeAg and HBcAg; HBsAg and HBcAg; HBeAg, HBsAg and HBcAg; HBeAg and an isoform of HBsAg; an isoform of HBsAg and HBcAg, HBeAg, an isoform of HBsAg and HBcAg; HBeAg and HBV DNA; HBeAg and HBV RNA; HBeAg and HBcrAg; HBeAg and anti-HBs; HBeAg and anti-HBe; HBcrAg and anti-HBc; HBeAg and ALT; HBeAg and AST; HBsAg and HBV DNA; an isoform of HBsAg and HBV DNA; HBsAg and HBV RNA; an isoform of HBsAg and HBV RNA; HBsAg and HBcrAg; an isoform of HBsAg and HBcrAg; HBsAg and anti-HBs; an isoform of HBsAg and anti-HBs; HBsAg and anti-HBe; an isoform of HBsAg and anti-HBe; HBsAg and anti-HBc; an isoform of HBsAg and anti-HBc; HBsAg and ALT; an isoform of HBsAg and ALT; HBsAg and AST; an isoform of HBsAg and AST; HBV DNA and HBV RNA; HBV DNA and HBcrAg; HBV DNA and anti-HBs; HBV DNA and anti-HBe; HBV DNA and anti-HBc; HBV DNA and ALT; HBV DNA and AST; HBV RNA and HBcrAg; HBV RNA and anti-HBs; HBV RNA and anti-HBe; HBV RNA and anti-HBc; HBV RNA and ALT; HBV RNA and AST; HBcrAg and anti-HBs; HBcrAg and anti-HBe; HBcrAg and anti-HBc; HBcrAg and ALT; HBcrAg and AST; anti-HBs and anti-HBe; anti-HBs and ALT; anti-HBe and AST; anti-HBe and ALT; anti-HBs and anti-HBc; anti-HBc and AST; anti-HBc and ALT; anti-HBe and anti-HBc; HBeAg, HBsAg, and HBV DNA; HBeAg, an isoform of HBsAg, and HBV DNA; HBeAg, HBsAg, and HBV RNA; HBeAg, HBsAg, and HBV RNA; HBeAg, HBsAg, and HBcrAg; HBeAg, an isoform of HBsAg, and HBcrAg; HBeAg, HBsAg, and anti-HBs; HBeAg, an isoform of HBsAg, and anti-HBs; HBeAg, HBsAg, and anti-HBe; HBeAg, an isoform of HBsAg, and anti-HBe; HBeAg, HBsAg, and anti-HBc; HBeAg, an isoform of HBsAg, and anti-HBc; HBeAg, HBsAg, and ALT; HBeAg, an isoform of HBsAg, and ALT; HBeAg, HBsAg, and AST; HBeAg, an isoform of HBsAg, and AST; HBeAg, HBV DNA, and HBV RNA; HBeAg, HBV DNA, and HBCrAg; HBeAg, HBV DNA, and anti-HBs; HBeAg, HBV DNA, and anti-HBe; HBeAg, HBV DNA, and anti-HBc; HBeAg, HBV DNA, and ALT; HBeAg, HBV DNA, and AST; HBeAg, HBV RNA and HBcrAG; HBeAg, HBV RNA, and anti-HBs; HBeAg, HBV RNA, and anti-HBe; HBeAg, HBV RNA, and anti-HBc; HBeAg, HBV RNA, and ALT; HBeAg, HBV RNA, and AST; HBeAG, HBcrAg, and anti-HBs; HBeAG, HBcrAg, and anti-HBe; HBeAG, HBcrAg, and anti-HBc; HBeAG, HBcrAg, and ALT; HBeAG, HBcrAg, and AST; HBeAG, anti-HBs, and anti-HBe; HBeAG, anti-HBs, and anti-HBc; HBeAG, anti-HBs, and ALT; HBeAG, anti-HBs, and AST; HBeAG, anti-HBe, and ALT; HBeAG, anti-HBs, and AST; HBeAG, anti-HBc, and ALT; HBeAG, anti-HBe, and AST; HBeAG, anti-HBc, and AST; HBeAG, ALT, and AST; HBsAg, HBV DNA, and HBV RNA; an isoform of HBsAg, HBV DNA, and HBV RNA; HBsAg, HBV DNA, and HBcrAg; an isoform of HBsAg, HBV DNA, and HBcrAg; HBsAg, HBV DNA, and anti-HBs; an isoform of HBsAg, HBV DNA, and antiHBs; HBsAg, HBV DNA, and anti-HBe; an isoform of HBsAg, HBV DNA, and anti-HBe; HBsAg, HBV DNA, and anti-HBc; an isoform of HBsAg, HBV DNA, and anti-HBc; HBsAg, HBV DNA, and ALT; an isoform of HBsAg, HBV DNA, and ALT; HBsAg, HBV DNA, and AST; an isoform of HBsAg, HBV DNA, and AST; HBsAg, HBV RNA, and HBcrAg; an isoform of HBsAg, HBV RNA, and HBcrAg; HBsAg, HBV RNA, and anti-HBs; an isoform of HBsAg, HBV RNA, and anti-HBs; HBsAg, HBV RNA, and anti-HBe; an isoform of HBsAg, HBV RNA, and anti-HBe; HBsAg, HBV RNA, and anti-HBc; an isoform of HBsAg, HBV RNA, and anti-HBc; HBsAg, HBV RNA, and ALT; an isoform of HBsAg, HBV RNA, and ALT; HBsAg, HBV RNA, and AST; an isoform of HBsAg, HBV RNA, and AST; HBsAg, HBcrAg, and anti-HBs; an isoform of HBsAg, HBcrAg, and anti-HBs; HBsAg, HBcrAg, and anti-HBe; an isoform of HBsAg, HBcrAg, and anti-HBe; HBsAg, HBcrAg, and anti-HBc; an isoform of HBsAg, HBcrAg, and anti-HBc; HBsAg, HBcrAg, and ALT; an isoform of HBsAg, HBcrAg, and ALT; HBsAg, HBcrAg, and AST; an isoform of HBsAg, HBcrAg, and AST; HBsAg, anti-HBs, and anti-HBe; an isoform of HBsAg, anti-HBs, and anti-HBe; HBsAg, anti-HBs, and anti-HBc; an isoform of HBsAg, anti-HBs, and anti-HBc; HBsAg, anti-HBs, and ALT; an isoform of HBsAg, anti-HBs, and ALT; HBsAg, anti-HBs, and AST; an isoform of HBsAg, anti-HBs, and AST; HBsAg, anti-HBe, and AST; an isoform of HBsAg, anti-HBe, and AST; HBsAg, anti-HBc, and AST; an isoform of HBsAg, anti-HBc, and AST; HBsAg, anti-HBe, and ALT; an isoform of HBsAg, anti-HBe, and ALT; HBsAg, anti-HBc, and ALT; an isoform of HBsAg, anti-HBc, and ALT; HBsAg, AST, and ALT; an isoform of HBsAg, AST, and ALT, anti-HBs, anti-HBe, and AST; anti-HBs, anti-HBc, and AST; anti-HBs, anti-HBe, and ALT; anti-HBs, anti-HBc, and ALT; anti-HBe, ALT, and AST; anti-HBc, ALT, and AST; HBeAg, HBsAg, HBV DNA, and HBV RNA; HBeAg, an isoform of HBsAg, HBV DNA, and HBV RNA; HBeAg, HBsAg, HBV DNA, and HBcrAg; HBeAg, HBsAg, HBV DNA, and anti-HBs; HBeAg, an isoform of HBsAg, HBV DNA, and HBcrAg; HBeAg, HBsAg, HBV DNA, and anti-HBs; HBeAg, HBsAg, HBV DNA, and anti-HBe; HBeAg, HBsAg, HBV DNA, and anti-HBc; HBeAg, HBsAg, HBV DNA, and ALT; HBeAg, an isoform of HBsAg, HBV DNA, and anti-HBe; HBeAg, an isoform of HBsAg, HBV DNA, and anti-HBc; HBeAg, HBsAg, HBV DNA, and ALT; HBeAg, HBsAg, HBV DNA, and AST; HBeAg, HBsAg, HBV RNA, and HBcrAg; HBeAg, an isoform of HBsAg, HBV DNA, and AST; HBeAg, HBsAg, HBV RNA, and HBcrAg; HBeAg, HBsAg, HBV RNA, and anti-HBs; HBeAg, an isoform of HBsAg, HBV RNA, and anti-HBs; HBeAg, HBsAg, HBV RNA, and anti-HBe; HBeAg, an isoform of HBsAg, HBV RNA, and anti-HBe; HBeAg, HBsAg, HBV RNA, and anti-HBc; HBeAg, an isoform of HBsAg, HBV RNA, and anti-HBc; HBeAg, HBsAg, HBV RNA, and ALT; HBeAg, an isoform of HBsAg, HBV RNA, and ALT; HBeAg, HBsAg, HBV RNA, and AST; HBeAg, an isoform HBsAg, HBV RNA, and AST; HBeAg, HBsAg, HBcrAg, and anti-HBs; HBeAg, an isoform of HBsAg, HBcrAg, and anti-HBs; HBeAg, HBsAg, HBcrAg, and anti-HBe; HBeAg, HBsAg, HBcrAg, and anti-HBc; HBeAg, an isoform of HBsAg, HBcrAg, and anti-HBe; HBeAg, an isoform of HBsAg, HBcrAg, and anti-HBc; HBeAg, HBsAg, HBcrAg, and ALT; HBeAg, an isoform of HBsAg, HBcrAg, and ALT; HBeAg, HBsAg, HBcrAg, and AST; HBeAg, an isoform of HBsAg, HBcrAg, and AST; HBeAg, HBsAg, anti-HBe, and anti-HBs; HBeAg, HBsAg, anti-HBc, and anti-HBs; HBeAg, HBsAg, anti-HBe, and ALT; HBeAg, HBsAg, anti-HBc, and ALT; HBeAg, an isoform of HBsAg, anti-HBe, and and ALT; HBeAg, an isoform of HBsAg, anti-HBc, and and ALT: HBeAg, HBsAg, anti-HBe, and AST; HBeAg, HBsAg, anti-HBs, and ALT; HBeAg, an isoform of HBsAg, anti-HBe, and AST; HBeAg, HBsAg, anti-HBs, and ALT; HBeAg, HBsAg, anti-HBc, and AST; HBeAg, HBsAg, anti-HBs, and ALT; HBeAg, an isoform of HBsAg, anti-HBc, and AST; HBeAg, HBsAg, anti-HBs, and ALT; HBeAg, HBsAg, anti-HBs, and AST; HBeAg, HBsAg, ALT, and AST; HBeAg, an isoform of HBsAg, anti-HBs, and AST; HBeAg, HBsAg, ALT, and AST; HBsAg, HBV DNA, HBV RNA, and HBcrAg; an isoform of HBsAg, HBV DNA, HBV RNA, and HBcrAg; HBsAg, HBV DNA, HBV RNA, and anti-HBs; an isoform of HBsAg, HBV DNA, HBV RNA, and anti-HBs; HBsAg, HBV DNA, HBV RNA, and anti-HBe; an isoform of HBsAg, HBV DNA, HBV RNA, and anti-HBe; HBsAg, HBV DNA, HBV RNA, and anti-HBc; an isoform of HBsAg, HBV DNA, HBV RNA, and anti-HBc; HBsAg, HBV DNA, HBV RNA, and ALT; an isoform of HBsAg, HBV DNA, HBV RNA, and ALT; HBsAg, HBV DNA, HBV RNA, and AST; an isoform of HBsAg, HBV DNA, HBV RNA, and AST; HBsAg, HBV RNA, HBcrAg and ant-HBs; an isoform of HBsAg, HBV RNA, HBcrAg and anti-HBs; HBsAg, HBV RNA, HBcrAg and ant-HBe; an isoform of HBsAg, HBV RNA, HBcrAg and ant-HBe; HBsAg, HBV RNA, HBcrAg and AST; an isoform of HBsAg, HBV RNA, HBcrAg and AST; HBsAg, HBV RNA, HBcrAg and ALT; an isoform of HBsAg, HBV RNA, HBcrAg and ALT; HBsAg, HBcrAg, anti-HBs, and ant-HBe; an isoform of HBsAg, HBcrAg, anti-HBs, and ant-HBe; HBsAg, HBcrAg, anti-HBs, and AST; an isoform of HBsAg, HBcrAg, anti-HBs, and AST; HBsAg, HBcrAg, anti-HBs, and ALT; an isoform of HBsAg, HBcrAg, anti-HBs, and ALT; HBsAg, anti-HBs, anti-HBe, and ALT; HBsAg, anti-HBs, anti-HBe, and AST; an isoform of HBsAg, anti-HBs, anti-HBe, and ALT; an isoform of HBsAg, anti-HBs, anti-HBe, and AST; HBsAg, anti-HBs, anti-HBc, and ALT; HBsAg, anti-HBs, anti-HBc, and AST; an isoform of HBsAg, anti-HBs, anti-HBc, and ALT; an isoform of HBsAg, anti-HBs, anti-HBc, and AST; HBsAg, anti-HBe, AST, and ALT; an isoform of HBsAg, anti-HBe, AST, and ALT; HBsAg, anti-HBc, AST, and ALT; an isoform of HBsAg, anti-HBc, AST, and ALT; HBV DNA, HBV RNA, HBcrAg, and anti-HBs; HBV DNA, HBV RNA, HBcrAg, and anti-HBe; HBV DNA, HBV RNA, HBcrAg, and anti-HBc; HBV DNA, HBV RNA, HBcrAg, and AST; HBV DNA, HBV RNA, HBcrAg, and ALT; HBV DNA, HBV RNA, anti-HBs, and anti-HBe; HBV DNA, HBV RNA, anti-HBs, and anti-HBc; HBV DNA, HBV RNA, anti-HBs, and AST; HBV DNA, HBV RNA, anti-HBs, and ALT; HBV DNA, HBV RNA, anti-HBe, and AST; HBV DNA, HBV RNA, anti-HBc, and AST; HBV DNA, HBV RNA, anti-HBe, and ALT; HBV DNA, HBV RNA, anti-HBc, and ALT; HBV DNA, HBV RNA, AST, and ALT; HBV RNA, HBcrAg, anti-HBs, and anti-HBe; HBV RNA, HBcrAg, anti-HBs, and anti-HBc; HBV RNA, HBcrAg, anti-HBs, and AST; HBV RNA, HBcrAg, anti-HBs, and ALT; HBV RNA, HBcrAg, anti-HBe, and AST; HBV RNA, HBcrAg, anti-HBc, and AST; HBV RNA, HBcrAg, anti-HBe, and ALT; HBV RNA, HBcrAg, anti-HBc, and ALT; HBV RNA, HBcrAg, AST; and ALT; HBcrAg, anti-HBs, anti-HBe, and AST; HBcrAg, anti-HBs, anti-HBc, and AST; HBcrAg, anti-HBs, anti-HBe, and ALT; HBcrAg, anti-HBe, AST, and ALT; HBcrAg, anti-HBs, anti-HBc, and ALT; HBcrAg, anti-HBe, AST, and ALT; anti-HBs, anti-HBe, AST, and ALT; anti-HBs, anti-HBc, AST, and ALT; HBeAg, HBsAg, HBV DNA, HBV RNA, and HBcrAg; HBeAg, an isoform of HBsAg, HBV DNA, HBV RNA, and HBcrAg; HBeAg, HBsAg, HBV DNA, HBV RNA, and anti-HBs; HBeAg, an isoform of HBsAg, HBV DNA, HBV RNA, and anti-HBs; HBeAg, HBsAg, HBV DNA, HBV RNA, and anti-HBe; HBeAg, an isoform of HBsAg, HBV DNA, HBV RNA, and anti-HBe; HBeAg, HBsAg, HBV DNA, HBV RNA, and anti-HBc; HBeAg, an isoform of HBsAg, HBV DNA, HBV RNA, and anti-HBc; HBeAg, HBsAg, HBV DNA, HBV RNA, and AST; HBeAg, an isoform of HBsAg, HBV DNA, HBV RNA, and AST; HBeAg, HBsAg, HBV DNA, HBV RNA, and ALT; HBeAg, an isoform of HBsAg, HBV DNA, HBV RNA, and ALT; HBeAg, HBsAg, HBV DNA, HBcrAg, and HBeAg; HBsAg, HBV DNA, HBcrAg, and anti-HBs; HBeAg, an isoform of HBsAg, HBV DNA, HBcrAg, and HBeAg; HBsAg, HBV DNA, HBcrAg, and anti-HBs; HBeAg, HBsAg, HBV DNA, HBcrAg, and anti-HBe; HBeAg, an isoform of HBsAg, HBV DNA, HBcrAg, and anti-HBe; HBeAg, HBsAg, HBV DNA, HBcrAg, and anti-HBc; HBeAg, an isoform of HBsAg, HBV DNA, HBcrAg, and anti-HBc; HBeAg, HBsAg, HBV DNA, HBcrAg, and AST; HBeAg, HBsAg, HBV DNA, HBcrAg, and AST; HBeAg, HBsAg, HBV DNA, HBcrAg, and ALT; HBeAg, an isoform of HBsAg, HBV DNA, HBcrAg, and ALT; HBeAg, HBsAg, HBV DNA, anti-HBs, and AST; HBeAg, an isoform of HBsAg, HBV DNA, anti-HBs, and AST; HBeAg, HBsAg, HBV DNA, anti-HBs, and ALT; HBeAg, an isoform of HBsAg, HBV DNA, anti-HBs, and ALT; HBeAg, HBsAg, HBV DNA, anti-HBe, and AST; HBeAg, an isoform of HBsAg, HBV DNA, anti-HBe, and AST; HBeAg, an HBsAg, HBV DNA, anti-HBc, and AST; HBeAg, an isoform of HBsAg, HBV DNA, anti-HBe, and AST; HBeAg, HBsAg, HBV DNA, anti-HBe, and ALT; HBeAg, an isoform of HBsAg, HBV DNA, anti-HBe, and ALT; HBeAg, HBsAg, HBV DNA, anti-HBc, and ALT; HBeAg, an isoform of HBsAg, HBV DNA, anti-HBc, and ALT; HBeAg, HBsAg, HBV DNA, AST, and ALT; HBeAg, an isoform of HBsAg, HBV DNA, AST, and ALT; HBsAg, HBV DNA, HBV RNA, HBcrAg, and anti-HBs; an isoform of HBsAg, HBV DNA, HBV RNA, HBcrAg, and anti-HBs; HBsAg, HBV DNA, HBV RNA, HBcrAg, and anti-HBe; an isoform of HBsAg, HBV DNA, HBV RNA, HBcrAg, and anti-HBe; HBsAg, HBV DNA, HBV RNA, HBcrAg, and anti-HBc; an isoform of HBsAg, HBV DNA, HBV RNA, HBcrAg, and anti-HBc; HBsAg, HBV DNA, HBV RNA, HBcrAg, and AST; an isoform of HBsAg, HBV DNA, HBV RNA, HBcrAg, and AST; HBsAg, HBV DNA, HBV RNA, HBcrAg, and ALT; an isoform HBsAg, HBV DNA, HBV RNA, HBcrAg, and ALT; HBsAg, HBV DNA, HBV RNA, anti-HBs, and anti-HBe; an isoform of HBsAg, HBV DNA, HBV RNA, anti-HBs, and anti-HBe; HBsAg, HBV DNA, HBV RNA, anti-HBs, and anti-HBc; an isoform of HBsAg, HBV DNA, HBV RNA, anti-HBs, and anti-HBc; HBsAg, HBV DNA, HBV RNA, anti-HBs, and AST; an isoform of HBsAg, HBV DNA, HBV RNA, anti-HBs, and AST; HBsAg, HBV DNA, HBV RNA, anti-HBs, and ALT; an isoform of HBsAg, HBV DNA, HBV RNA, anti-HBs, and ALT; HBsAg, HBV DNA, HBV RNA, anti-HBe, and AST; an isoform of HBsAg, HBV DNA, HBV RNA, anti-HBe, and AST; HBsAg, HBV DNA, HBV RNA, anti-HBc, and AST; an isoform of HBsAg, HBV DNA, HBV RNA, anti-HBe, and AST; HBsAg, HBV DNA, HBV RNA, anti-HBe, and ALT; an isoform of HBsAg, HBV DNA, HBV RNA, anti-HBe, and ALT; HBsAg, HBV DNA, HBV RNA, anti-HBc, and ALT; an isoform of HBsAg, HBV DNA, HBV RNA, anti-HBc, and ALT; HBsAg, HBV DNA, HBV RNA, AST, and ALT; an isoform of HBsAg, HBV DNA, HBV RNA, AST, and ALT; HBV DNA, HBV RNA, HBcrAg, anti-HBs, and anti-HBe; HBV DNA, HBV RNA, HBcrAg, anti-HBs, and anti-HBc; HBV DNA, HBV RNA, HBcrAg, anti-HBs, and AST; HBV DNA, HBV RNA, HBcrAg, anti-HBs, and ALT; HBV DNA, HBV RNA, HBcrAg, anti-HBe, and AST; HBV DNA, HBV RNA, HBcrAg, anti-HBc, and AST; HBV DNA, HBV RNA, HBcrAg, anti-HBe, and ALT; HBV DNA, HBV RNA, HBcrAg, anti-HBc, and ALT; HBV DNA, HBV RNA, HBcrAg, ALT, and AST; HBV RNA, HBcrAg, anti-HBs, anti-HBe, and AST; HBV RNA, HBcrAg, anti-HBs, anti-HBc, and AST; HBV RNA, HBcrAg, anti-HBs, anti-HBe, and ALT; HBV RNA, HBcrAg, anti-HBs, anti-HBc, and ALT; HBcrAg, anti-HBs, anti-HBe, ALT, and AST; HBcrAg, anti-HBs, anti-HBc, ALT, and AST; HBeAg, HBsAg, HBV DNA, HBV RNA, HBcrAg, and anti-HBs; HBeAg, an isoform of HBsAg, HBV DNA, HBV RNA, HBcrAg, and anti-HBs; HBeAg, HBsAg, HBV DNA, HBV RNA, HBcrAg, and anti-HBe; HBeAg, an isoform of HBsAg, HBV DNA, HBV RNA, HBcrAg, and anti-HBe; HBeAg, HBsAg, HBV DNA, HBV RNA, HBcrAg, and anti-HBc; HBeAg, an isoform of HBsAg, HBV DNA, HBV RNA, HBcrAg, and anti-HBe; HBeAg, HBsAg, HBV DNA, HBV RNA, HBcrAg, and AST; HBeAg, an isoform of HBsAg, HBV DNA, HBV RNA, HBcrAg, and AST; HBeAg, HBsAg, HBV DNA, HBV RNA, HBcrAg, and ALT; HBeAg, an isoform of HBsAg, HBV DNA, HBV RNA, HBcrAg, and ALT; HBeAg, HBsAg, HBV DNA, HBV RNA, anti-HBs, and anti-HBe; HBeAg, an isoform of HBsAg, HBV DNA, HBV RNA, anti-HBs, and anti-HBe; HBeAg, HBsAg, HBV DNA, HBV RNA, anti-HBs, and anti-HBc; HBeAg, an isoform of HBsAg, HBV DNA, HBV RNA, anti-HBs, and anti-HBc; HBeAg, HBsAg, HBV DNA, HBV RNA, anti-HBs, and AST; HBeAg, an isoform of HBsAg, HBV DNA, HBV RNA, anti-HBs, and AST; HBeAg, HBsAg, HBV DNA, HBV RNA, anti-HBs, and ALT; HBeAg, an isoform of HBsAg, HBV DNA, HBV RNA, anti-HBs, and ALT; HBeAg, HBsAg, HBV DNA, HBV RNA, anti-HBe, and AST; HBeAg, an isoform of HBsAg, HBV DNA, HBV RNA, anti-HBe, and AST; HBeAg, HBsAg, HBV DNA, HBV RNA, anti-HBc, and AST; HBeAg, an isoform of HBsAg, HBV DNA, HBV RNA, anti-HBc, and AST; HBeAg, HBsAg, HBV DNA, HBV RNA, anti-HBe, and ALT; HBeAg, HBV DNA, HBV RNA, anti-HBc, and ALT; HBeAg, an isoform of HBsAg, HBV DNA, HBV RNA, anti-HBe, and ALT; HBeAg, an isoform of HBsAg, HBV DNA, HBV RNA, anti-HBc, and ALT; HBeAg, HBsAg, HBV DNA, HBV RNA, AST, and ALT; HBeAg, an isoform of HBsAg, HBV DNA, HBV RNA, AST, and ALT; HBsAg, HBV DNA, HBV RNA, HBcrAG, anti-HBs, and anti-HBe; an isoform of HBsAg, HBV DNA, HBV RNA, HBcrAG, anti-HBs, and anti-HBe; HBsAg, HBV DNA, HBV RNA, HBcrAG, anti-HBs, and anti-HBc; an isoform of HBsAg, HBV DNA, HBV RNA, HBcrAG, anti-HBs, and anti-HBc; HBsAg, HBV DNA, HBV RNA, HBcrAG, anti-HBs, and AST; an isoform of HBsAg, HBV DNA, HBV RNA, HBcrAG, anti-HBs, and AST; HBsAg, HBV DNA, HBV RNA, HBcrAG, anti-HBs, and ALT; an isoform of HBsAg, HBV DNA, HBV RNA, HBcrAG, anti-HBs, and ALT; HBsAg, HBV DNA, HBV RNA, HBcrAG, anti-HBe, and AST; an isoform of HBsAg, HBV DNA, HBV RNA, HBcrAG, anti-HBe, and AST; HBsAg, HBV DNA, HBV RNA, HBcrAG, anti-HBc, and AST; an isoform of HBsAg, HBV DNA, HBV RNA, HBcrAG, anti-HBc, and AST; HBsAg, HBV DNA, HBV RNA, HBcrAG, anti-HBe, and ALT; an isoform of HBsAg, HBV DNA, HBV RNA, HBcrAG, anti-HBe, and ALT; HBsAg, HBV DNA, HBV RNA, HBcrAG, anti-HBc, and ALT; an isoform of HBsAg, HBV DNA, HBV RNA, HBcrAG, anti-HBc, and ALT; HBsAg, HBV DNA, HBV RNA, HBcrAG, AST, and ALT; an isoform of HBsAg, HBV DNA, HBV RNA, HBcrAG, AST, and ALT; HBV DNA, HBV RNA, HBcrAG, anti-HBs, anti-HBe, and AST; HBV DNA, HBV RNA, HBcrAG, anti-HBs, anti-HBc, and AST; HBV DNA, HBV RNA, HBcrAG, anti-HBs, anti-HBe, and ALT; HBV DNA, HBV RNA, HBcrAG, anti-HBs, anti-HBc, and ALT; HBV DNA, HBV RNA, HBcrAG, anti-HBs, ALT, and AST; HBV RNA, HBcrAG, anti-HBs, anti-HBe, ALT, and AST; HBV RNA, HBcrAG, anti-HBs, anti-HBc, ALT, and AST; HBeAg, HBsAg, HBV DNA, HBV RNA, HBcrAg, anti-HBs, and anti-HBe; HBeAg, an isoform of HBsAg, HBV DNA, HBV RNA, HBcrAg, anti-HBs, and anti-HBe; HBeAg, HBsAg, HBV DNA, HBV RNA, HBcrAg, anti-HBs, and anti-HBc; HBeAg, an isoform of HBsAg, HBV DNA, HBV RNA, HBcrAg, anti-HBs, and anti-HBc; HBeAg, HBsAg, HBV DNA, HBV RNA, HBcrAg, anti-HBs, and AST; HBeAg, an isoform of HBsAg, HBV DNA, HBV RNA, HBcrAg, anti-HBs, and AST; HBeAg, HBsAg, HBV DNA, HBV RNA, HBcrAg, anti-HBs, and ALT; HBeAg, an isoform of HBsAg, HBV DNA, HBV RNA, HBcrAg, anti-HBs, and ALT; HBeAg, HBsAg, HBV DNA, HBV RNA, HBcrAg, anti-HBe, and AST; HBeAg, an isoform of HBsAg, HBV DNA, HBV RNA, HBcrAg, anti-HBe, and AST; HBeAg, HBsAg, HBV DNA, HBV RNA, HBcrAg, anti-HBc, and AST; HBeAg, an isoform of HBsAg, HBV DNA, HBV RNA, HBcrAg, anti-HBc, and AST; HBeAg, HBsAg, HBV DNA, HBV RNA, HBcrAg, anti-HBe, and ALT; HBeAg, HBsAg, HBV DNA, HBV RNA, HBcrAg, anti-HBc, and ALT; HBeAg, an isoform of HBsAg, HBV DNA, HBV RNA, HBcrAg, anti-HBe, and ALT; HBeAg, an isoform of HBsAg, HBV DNA, HBV RNA, HBcrAg, anti-HBc, and ALT; HBeAg, HBsAg, HBV DNA, HBV RNA, HBcrAg, ALT, and AST; HBeAg, an isoform of HBsAg, HBV DNA, HBV RNA, HBcrAg, ALT, and AST; HBsAg, HBV DNA, HBV RNA, HBcrAg, anti-HBs, anti-HBe, and AST; an isoform of HBsAg, HBV DNA, HBV RNA, HBcrAg, anti-HBs, anti-HBe, and AST; HBsAg, HBV DNA, HBV RNA, HBcrAg, anti-HBs, anti-HBc, and AST; an isoform of HBsAg, HBV DNA, HBV RNA, HBcrAg, anti-HBs, anti-HBc, and AST; HBsAg, HBV DNA, HBV RNA, HBcrAg, anti-HBs, anti-HBe, and ALT; an isoform of HBsAg, HBV DNA, HBV RNA, HBcrAg, anti-HBs, anti-HBe, and ALT; HBsAg, HBV DNA, HBV RNA, HBcrAg, anti-HBs, anti-HBc, and ALT; an isoform of HBsAg, HBV DNA, HBV RNA, HBcrAg, anti-HBs, anti-HBc, and ALT; HBV DNA, HBV RNA, HBcrAg, anti-HBs, anti-HBe, AST and ALT; HBV DNA, HBV RNA, HBcrAg, anti-HBs, anti-HBc, AST and ALT; HBeAg, HBsAg, HBV DNA, HBV RNA, HBcrAg, anti-HBs, anti-HBe, and AST; HBeAg, an isoform of HBsAg, HBV DNA, HBV RNA, HBcrAg, anti-HBs, anti-HBe, and AST; HBeAg, HBsAg, HBV DNA, HBV RNA, HBcrAg, anti-HBs, anti-HBc, and AST; HBeAg, an isoform of HBsAg, HBV DNA, HBV RNA, HBcrAg, anti-HBs, anti-HBc, and AST; HBeAg, HBsAg, HBV DNA, HBV RNA, HBcrAg, anti-HBs, anti-HBe, and ALT; HBeAg, HBsAg, HBV DNA, HBV RNA, HBcrAg, anti-HBs, anti-HBc, and ALT; HBsAg, HBV DNA, HBV RNA, HBcrAg, anti-HBs, anti-HBe, AST, and ALT; an isoform of HBsAg, HBV DNA, HBV RNA, HBcrAg, anti-HBs, anti-HBe, AST, and ALT; HBsAg, HBV DNA, HBV RNA, HBcrAg, anti-HBs, anti-HBc, AST, and ALT; an isoform of HBsAg, HBV DNA, HBV RNA, HBcrAg, anti-HBs, anti-HBc, AST, and ALT; HBeAg, HBsAg, HBV DNA, HBV RNA, HBcrAg, anti-HBs, anti-HBe, AST, and ALT; HBeAg, an isoform of HBsAg, HBV DNA, HBV RNA, HBcrAg, anti-HBs, anti-HBe, AST, and ALT; HBeAg, HBsAg, HBV DNA, HBV RNA, HBcrAg, anti-HBs, anti-HBc, AST, and ALT; HBeAg, an isoform of HBsAg, HBV DNA, HBV RNA, HBcrAg, anti-HBs, anti-HBc, AST, and ALT, HBeAg and HBcAg; HBcAg and anti-HBc; HBsAg and HBcAg; an isoform of HBsAg and HBcAg; HBV DNA and HBcAg; HBV RNA and HBcAg; HBcAg and anti-HBs; HBcAg and anti-HBe; HBcAg and anti-HBc; HBcAg and ALT; HBcAg and AST; HBeAg, HBsAg, and HBcAg; HBeAg, an isoform of HBsAg, and HBcAg; HBeAg, HBV DNA, and HBcAg; HBeAg, HBV RNA and HBcAg; HBeAG, HBcAg, and anti-HBs; HBeAG, HBcAg, and anti-HBe; HBeAG, HBcAg, and anti-HBc; HBeAG, HBcAg, and ALT; HBeAG, HBcAg, and AST; HBsAg, HBV DNA, and HBcAg; an isoform of HBsAg, HBV DNA, and HBcAg; HBsAg, HBV RNA, and HBcAg; an isoform of HBsAg, HBV RNA, and HBcAg; HBsAg, HBcAg, and anti-HBs; an isoform of HBsAg, HBcAg, and anti-HBs; HBsAg, HBcAg, and anti-HBe; an isoform of HBsAg, HBcAg, and anti-HBe; HBsAg, HBcAg, and anti-HBc; an isoform of HBsAg, HBcAg, and anti-HBc; HBsAg. HBcAg, and ALT; an isoform of HBsAg, HBcAg, and ALT; HBsAg, HBcAg, and AST; an isoform of HBsAg, HBcAg, and AST; HBeAg, HBsAg, HBV DNA, and HBcAg; HBeAg, an isoform of HBsAg, HBV DNA, and HBcAg; HBeAg, HBsAg, HBV RNA, and HBcAg; HBeAg, HBsAg, HBV RNA, and HBcAg; HBeAg, HBsAg, HBcAg, and anti-HBs; HBeAg, an isoform of HBsAg, HBcAg, and anti-HBs; HBeAg, HBsAg, HBcAg, and anti-HBe; HBeAg, HBsAg, HBcAg, and anti-HBc; HBeAg, an isoform of HBsAg, HBcAg, and anti-HBe; HBeAg, an isoform of HBsAg, HBcAg, and anti-HBc; HBeAg, HBsAg, HBcAg, and ALT; HBeAg, an isoform of HBsAg, HBcAg, and ALT; HBeAg, HBsAg, HBcAg, and AST; HBeAg, an isoform of HBsAg, HBcAg, and AST; HBsAg, HBV DNA, HBV RNA, and HBcAg; an isoform of HBsAg, HBV DNA, HBV RNA, and HBcAg; HBsAg, HBV RNA, HBcAg and ant-HBs; an isoform of HBsAg, HBV RNA, HBcAg and ant-HBs; HBsAg, HBV RNA, HBcAg and ant-HBe; an isoform of HBsAg, HBV RNA, HBcAg and ant-HBe; HBsAg, HBV RNA, HBcAg and AST; an isoform of HBsAg, HBV RNA, HBcAg and AST; HBsAg, HBV RNA, HBcAg and ALT; an isoform of HBsAg, HBV RNA, HBcAg and ALT; HBsAg, HBcAg, anti-HBs, and ant-HBe; an isoform of HBsAg, HBcAg, anti-HBs, and ant-HBe; HBsAg, HBcAg, anti-HBs, and AST; an isoform of HBsAg, HBcAg, anti-HBs, and AST; HBsAg, HBcAg, anti-HBs, and ALT; an isoform of HBsAg, HBcAg, anti-HBs, and ALT; HBsAg, anti-HBs, anti-HBe, and ALT; HBV DNA, HBV RNA, HBcAg, and anti-HBs; HBV DNA, HBV RNA, HBcAg, and anti-HBe; HBV DNA, HBV RNA, HBcAg, and anti-HBc; HBV DNA, HBV RNA, HBcAg, and AST; HBV DNA, HBV RNA, HBcAg, and ALT; HBV RNA, HBcAg, anti-HBs, and anti-HBe; HBV RNA, HBcAg, anti-HBs, and anti-HBc; HBV RNA, HBcAg, anti-HBs, and AST; HBV RNA, HBcAg, anti-HBs, and ALT; HBV RNA, HBcAg, anti-HBe, and AST; HBV RNA, HBcAg, anti-HBc, and AST; HBV RNA, HBcAg, anti-HBe, and ALT; HBV RNA, HBcAg, anti-HBc, and ALT; HBV RNA, HBcAg, AST; and ALT; HBcAg, anti-HBs, anti-HBe, and AST; HBcAg, anti-HBs, anti-HBc, and AST; HBcAg, anti-HBs, anti-HBe, and ALT; HBcAg, anti-HBe, AST, and ALT; HBcAg, anti-HBs, anti-HBc, and ALT; HBcAg, anti-HBe, AST, and ALT; anti-HBs, anti-HBe, AST, and ALT; anti-HBs, anti-HBc, AST, and ALT; HBeAg, HBsAg, HBV DNA, HBV RNA, and HBcAg; HBeAg, an isoform of HBsAg, HBV DNA, HBV RNA, and HBcAg; HBeAg, HBsAg, HBV DNA, HBcAg, and HBeAg, HBsAg, HBV DNA, HBcAg, and anti-HBs; HBeAg, an isoform of HBsAg, HBV DNA, HBcAg, and HBeAg, HBsAg, HBV DNA, HBcAg, and anti-HBs; HBeAg, HBsAg, HBV DNA, HBcAg, and anti-HBe; HBeAg, an isoform of HBsAg, HBV DNA, HBcAg, and anti-HBe; HBeAg, HBsAg, HBV DNA, HBcAg, and anti-HBc; HBeAg, an isoform of HBsAg, HBV DNA, HBcAg, and anti-HBc; HBeAg, HBsAg, HBV DNA, HBcAg, and AST; HBeAg, HBsAg, HBV DNA, HBcAg, and AST; HBeAg, HBsAg, HBV DNA, HBcAg, and ALT; HBeAg, an isoform of HBsAg, HBV DNA, HBcAg, and ALT; HBsAg, HBV DNA, HBV RNA, HBcAg, and anti-HBs; an isoform of HBsAg, HBV DNA, HBV RNA, HBcAg, and anti-HBs; HBsAg, HBV DNA, HBV RNA, HBcAg, and anti-HBe; an isoform of HBsAg, HBV DNA, HBV RNA, HBcAg, and anti-HBe; HBsAg, HBV DNA, HBV RNA, HBcAg, and anti-HBc; an isoform of HBsAg, HBV DNA, HBV RNA, HBcAg, and anti-HBc; HBsAg, HBV DNA, HBV RNA, HBcAg, and AST; an isoform of HBsAg, HBV DNA, HBV RNA, HBcAg, and AST; HBsAg, HBV DNA, HBV RNA, HBcAg, and ALT: an isoform HBsAg, HBV DNA, HBV RNA, HBcAg, and ALT; HBV DNA, HBV RNA, HBcAg, anti-HBs, and anti-HBe; HBV DNA, HBV RNA, HBcAg, anti-HBs, and anti-HBc; HBV DNA, HBV RNA, HBcAg, anti-HBs, and AST; HBV DNA, HBV RNA, HBcAg, anti-HBs, and ALT; HBV DNA, HBV RNA, HBcAg, anti-HBe, and AST; HBV DNA, HBV RNA, HBcAg, anti-HBc, and AST; HBV DNA, HBV RNA, HBcAg, anti-HBe, and ALT; HBV DNA, HBV RNA, HBcAg, anti-HBc, and ALT; HBV DNA, HBV RNA, HBcAg, ALT, and AST; HBV RNA, HBcAg, anti-HBs, anti-HBe, and AST; HBV RNA, HBcAg, anti-HBs, anti-HBc, and AST; HBV RNA, HBcAg, anti-HBs, anti-HBe, and ALT; HBV RNA, HBcAg, anti-HBs, anti-HBc, and ALT; HBcAg, anti-HBs, anti-HBe, ALT, and AST; HBcAg, anti-HBs, anti-HBc, ALT, and AST; HBeAg, HBsAg, HBV DNA, HBV RNA, HBcAg, and anti-HBs; HBeAg, an isoform of HBsAg, HBV DNA, HBV RNA, HBcAg, and anti-HBs; HBeAg, HBsAg, HBV DNA, HBV RNA, HBcAg, and anti-HBe; HBeAg, an isoform of HBsAg, HBV DNA, HBV RNA, HBcAg, and anti-HBe; HBeAg, HBsAg, HBV DNA, HBV RNA, HBcAg, and anti-HBc; HBeAg, an isoform of HBsAg, HBV DNA, HBV RNA, HBcAg, and anti-HBe; HBeAg, HBsAg, HBV DNA, HBV RNA, HBcAg, and AST; HBeAg, an isoform of HBsAg, HBV DNA, HBV RNA, HBcAg, and AST; HBeAg, HBsAg, HBV DNA, HBV RNA, HBcAg, and ALT; HBeAg, an isoform of HBsAg, HBV DNA, HBV RNA, HBcAg, and ALT; HBsAg, HBV DNA, HBV RNA, HBcAg, anti-HBs, and anti-HBe; an isoform of HBsAg, HBV DNA, HBV RNA, HBcAg, anti-HBs, and anti-HBe; HBsAg, HBV DNA, HBV RNA, HBcAg, anti-HBs, and anti-HBc; an isoform of HBsAg, HBV DNA, HBV RNA, HBcAg, anti-HBs, and anti-HBc; HBsAg, HBV DNA, HBV RNA, HBcAg, anti-HBs, and AST; an isoform of HBsAg, HBV DNA, HBV RNA, HBcAg, anti-HBs, and AST; HBsAg, HBV DNA, HBV RNA, HBcAg, anti-HBs, and ALT; an isoform of HBsAg, HBV DNA, HBV RNA, HBcAg, anti-HBs, and ALT; HBsAg, HBV DNA, HBV RNA, HBcAg, anti-HBe, and AST; an isoform of HBsAg, HBV DNA, HBV RNA, HBcAg, anti-HBe, and AST; HBsAg, HBV DNA, HBV RNA, HBcAg, anti-HBc, and AST; an isoform of HBsAg, HBV DNA, HBV RNA, HBcAg, anti-HBc, and AST; HBsAg, HBV DNA, HBV RNA, HBcAg, anti-HBe, and ALT; an isoform of HBsAg, HBV DNA, HBV RNA, HBcAg, anti-HBe, and ALT; HBsAg, HBV DNA, HBV RNA, HBcAg, anti-HBc, and ALT; an isoform of HBsAg, HBV DNA, HBV RNA, HBcAg, anti-HBc, and ALT; HBsAg, HBV DNA, HBV RNA, HBcAg, AST, and ALT; an isoform of HBsAg, HBV DNA, HBV RNA, HBcAg, AST, and ALT; HBV DNA, HBV RNA, HBcAg, anti-HBs, anti-HBe, and AST; HBV DNA, HBV RNA, HBcAg, anti-HBs, anti-HBc, and AST; HBV DNA, HBV RNA, HBcAg, anti-HBs, anti-HBe, and ALT; HBV DNA, HBV RNA, HBcAg, anti-HBs, anti-HBc, and ALT; HBV DNA, HBV RNA, HBcAg, anti-HBs, ALT, and AST; HBV RNA, HBcAg, anti-HBs, anti-HBe, ALT, and AST; HBV RNA, HBcAg, anti-HBs, anti-HBc, ALT, and AST; HBeAg, HBsAg, HBV DNA, HBV RNA, HBcAg, anti-HBs, and anti-HBe; HBeAg, an isoform of HBsAg, HBV DNA, HBV RNA, HBcAg, anti-HBs, and anti-HBe; HBeAg, HBsAg, HBV DNA, HBV RNA, HBcAg, anti-HBs, and anti-HBc; HBeAg, an isoform of HBsAg, HBV DNA, HBV RNA, HBcAg, anti-HBs, and anti-HBc; HBeAg, HBsAg, HBV DNA, HBV RNA, HBcAg, anti-HBs, and AST; HBeAg, an isoform of HBsAg, HBV DNA, HBV RNA, HBcAg, anti-HBs, and AST; HBeAg, HBsAg, HBV DNA, HBV RNA, HBcAg, anti-HBs, and ALT; HBeAg, an isoform of HBsAg, HBV DNA, HBV RNA, HBcAg, anti-HBs, and ALT; HBeAg, HBsAg, HBV DNA, HBV RNA, HBcAg, anti-HBe, and AST; HBeAg, an isoform of HBsAg, HBV DNA, HBV RNA, HBcAg, anti-HBe, and AST; HBeAg, HBsAg, HBV DNA, HBV RNA, HBcAg, anti-HBc, and AST; HBeAg, an isoform of HBsAg, HBV DNA, HBV RNA, HBcAg, anti-HBc, and AST; HBeAg, HBsAg, HBV DNA, HBV RNA, HBcAg, anti-HBe, and ALT; HBeAg, an isoform of HBsAg, HBV DNA, HBV RNA, HBcAg, anti-HBe, and ALT; HBeAg, HBsAg, HBV DNA, HBV RNA, HBcAg, anti-HBc, and ALT; HBeAg, an isoform of HBsAg, HBV DNA, HBV RNA, HBcAg, anti-HBc, and ALT; HBeAg, HBsAg, HBV DNA, HBV RNA, HBcAg, ALT, and AST; HBeAg, an isoform of HBsAg, HBV DNA, HBV RNA, HBcAg, ALT, and AST; HBsAg, HBV DNA, HBV RNA, HBcAg, anti-HBs, anti-HBe, and AST; an isoform of HBsAg, HBV DNA, HBV RNA, HBcAg, anti-HBs, anti-HBe, and AST; HBsAg, HBV DNA, HBV RNA, HBcAg, anti-HBs, anti-HBc, and AST; an isoform of HBsAg, HBV DNA, HBV RNA, HBcAg, anti-HBs, anti-HBc, and AST; HBsAg, HBV DNA, HBV RNA, HBcAg, anti-HBs, anti-HBe, and ALT; an isoform of HBsAg, HBV DNA, HBV RNA, HBcAg, anti-HBs, anti-HBe, and ALT; HBsAg, HBV DNA, HBV RNA, HBcAg, anti-HBs, anti-HBc, and ALT; an isoform of HBsAg, HBV DNA, HBV RNA, HBcAg, anti-HBs, anti-HBc, and ALT; HBV DNA, HBV RNA, HBcAg, anti-HBs, anti-HBe, AST and ALT; HBV DNA, HBV RNA, HBcAg, anti-HBs, anti-HBc, AST and ALT; HBeAg, HBsAg, HBV DNA, HBV RNA, HBcAg, anti-HBs, anti-HBe, and AST; HBeAg, an isoform of HBsAg, HBV DNA, HBV RNA, HBcAg, anti-HBs, anti-HBe, and AST; HBeAg, HBsAg, HBV DNA, HBV RNA, HBcAg, anti-HBs, anti-HBc, and AST; HBeAg, an isoform of HBsAg, HBV DNA, HBV RNA, HBcAg, anti-HBs, anti-HBc, and AST; HBeAg, HBsAg, HBV DNA, HBV RNA, HBcAg, anti-HBs, anti-HBe, and ALT; HBeAg, HBsAg, HBV DNA, HBV RNA, HBcAg, anti-HBs, anti-HBc, and ALT; HBsAg, HBV DNA, HBV RNA, HBcAg, anti-HBs, anti-HBe, AST, and ALT; an isoform of HBsAg, HBV DNA, HBV RNA, HBcAg, anti-HBs, anti-HBe, AST, and ALT; HBsAg, HBV DNA, HBV RNA, HBcAg, anti-HBs, anti-HBc, AST, and ALT; an isoform of HBsAg, HBV DNA, HBV RNA, HBcAg, anti-HBs, anti-HBc, AST, and ALT; HBeAg, HBsAg, HBV DNA, HBV RNA, HBcAg, anti-HBs, anti-HBe, AST, and ALT; HBeAg, an isoform of HBsAg, HBV DNA, HBV RNA, HBcAg, anti-HBs, anti-HBe, AST, and ALT; HBeAg, HBsAg, HBV DNA, HBV RNA, HBcAg, anti-HBs, anti-HBc, AST, and ALT; HBeAg, an isoform of HBsAg, HBV DNA, HBV RNA, HBcAg, anti-HBs, anti-HBc, AST, and ALT, HBeAg and HBsAg immune complexes; HBsAg immune complexes and HBcAg; HBeAg, HBsAg immune complexes and HBcAg; HBsAg immune complexes and HBV DNA; HBsAg immune complexes and HBV RNA; HBsAg immune complexes and HBcrAg; HBsAg immune complexes and anti-HBs; HBsAg immune complexes and anti-HBe; HBsAg immune complexes and anti-HBc; HBsAg immune complexes and ALT; HBsAg immune complexes and AST; HBeAg, HBsAg immune complexes, and HBV DNA; HBeAg, HBeAg, HBsAg immune complexes, and HBV RNA; HBeAg, HBsAg immune complexes, and HBV RNA; HBeAg, HBsAg immune complexes, and HBcrAg; HBeAg, HBeAg, HBsAg immune complexes, and anti-HBs; HBeAg, HBsAg immune complexes, and anti-HBe; HBeAg, HBsAg immune complexes, and anti-HBc; HBeAg, HBsAg immune complexes, and AST; HBsAg immune complexes, HBV DNA, and HBcrAg; HBsAg immune complexes, HBV DNA, and anti-HBe; HBsAg immune complexes, HBV DNA, and anti-HBc; HBsAg immune complexes, HBV DNA, and ALT; HBsAg immune complexes, HBV DNA, and AST; HBsAg immune complexes, HBV RNA, and HBcrAg; HBsAg immune complexes, HBV RNA, and anti-HBs; HBsAg immune complexes, HBV RNA, and anti-HBe; HBsAg immune complexes, HBV RNA, and anti-HBc; HBsAg immune complexes, HBV RNA, and ALT; HBsAg immune complexes, HBV RNA, and AST; HBsAg immune complexes, HBcrAg, and anti-HBs; HBsAg immune complexes, HBcrAg, and anti-HBe; HBsAg immune complexes, HBcrAg, and anti-HBc; HBsAg immune complexes, HBcrAg, and ALT; HBsAg immune complexes, HBcrAg, and AST; HBsAg immune complexes, anti-HBs, and anti-HBe; HBsAg immune complexes, anti-HBs, and anti-HBc; HBsAg immune complexes, anti-HBs, and ALT; HBsAg immune complexes, anti-HBs, and AST; HBsAg immune complexes, anti-HBe, and AST; HBsAg immune complexes, anti-HBc, and AST; HBsAg immune complexes, anti-HBe, and ALT; HBsAg immune complexes, anti-HBc, and ALT; HBsAg immune complexes, AST, and ALT; HBeAg, HBsAg immune complexes, HBV DNA, and HBV RNA; HBeAg, HBsAg immune complexes, HBV DNA, and HBcrAg; HBeAg, HBsAg immune complexes, HBV DNA, and anti-HBs; HBeAg, HBsAg immune complexes, HBV DNA, and anti-HBe; HBeAg, HBsAg immune complexes, HBV DNA, and anti-HBc; HBeAg, HBsAg immune complexes, HBV DNA, and ALT; HBeAg, HBsAg immune complexes, HBV DNA, and ALT; HBeAg, HBsAg immune complexes, HBV DNA, and AST; HBeAg, HBsAg immune complexes, HBV RNA, and HBcrAg; HBeAg, HBsAg immune complexes, HBV RNA, and HBcrAg; HBeAg, HBsAg immune complexes, HBV RNA, and anti-HBs; HBeAg, HBsAg immune complexes, HBV RNA, and anti-HBe; HBeAg, HBsAg immune complexes, HBV RNA, and anti-HBc; HBeAg, HBsAg immune complexes, HBV RNA, and ALT; HBeAg, HBsAg immune complexes, HBV RNA, and AST; HBeAg, HBsAg immune complexes, HBcrAg, and anti-HBs; HBeAg, HBsAg immune complexes, HBcrAg, and anti-HBe; HBeAg, HBsAg immune complexes, HBcrAg, and anti-HBc; HBeAg, HBsAg immune complexes, HBcrAg, and ALT; HBeAg, HBsAg immune complexes, HBcrAg, and AST; HBeAg, HBsAg immune complexes, anti-HBe, and anti-HBs; HBeAg, HBsAg immune complexes, anti-HBc, and anti-HBs; HBeAg, HBsAg immune complexes, anti-HBe, and ALT; HBeAg, HBsAg immune complexes, anti-HBc, and ALT; HBeAg, HBsAg immune complexes, anti-HBe, and AST; HBeAg, HBsAg immune complexes, anti-HBs, and ALT; HBeAg, HBsAg immune complexes, anti-HBs, and ALT; HBeAg, HBsAg immune complexes, anti-HBc, and AST; HBeAg, HBsAg immune complexes, anti-HBs, and ALT; HBeAg, HBsAg immune complexes, anti-HBs, and ALT; HBeAg, HBsAg immune complexes, anti-HBs, and AST; HBeAg, HBsAg immune complexes, ALT, and AST; HBeAg, HBsAg immune complexes, ALT, and AST; HBsAg immune complexes, HBV DNA, HBV RNA, and HBcrAg; HBsAg immune complexes, HBV DNA, HBV RNA, and anti-HBs; HBsAg immune complexes, HBV DNA, HBV RNA, and anti-HBe; HBsAg immune complexes, HBV DNA, HBV RNA, and anti-HBc; HBsAg immune complexes, HBV DNA, HBV RNA, and ALT; HBsAg immune complexes, HBV DNA, HBV RNA, and AST; HBsAg immune complexes, HBV RNA, HBcrAg and ant-HBs; HBsAg immune complexes, HBV RNA, HBcrAg and ant-HBe; HBsAg immune complexes, HBV RNA, HBcrAg and ALT; HBsAg immune complexes, HBcrAg, anti-HBs, and ant-HBe; HBsAg immune complexes, HBcrAg, anti-HBs, and AST; HBsAg immune complexes, HBcrAg, anti-HBs, and ALT; HBsAg immune complexes, anti-HBs, anti-HBe, and ALT; HBsAg immune complexes, anti-HBs, anti-HBe, and AST; HBsAg immune complexes, anti-HBs, anti-HBc, and ALT; HBsAg immune complexes, anti-HBs, anti-HBc, and AST; HBsAg immune complexes, anti-HBe, AST, and ALT; HBsAg immune complexes, anti-HBc, AST, and ALT; HBeAg, HBsAg immune complexes, HBV DNA, HBV RNA, and HBcrAg; HBeAg, HBsAg immune complexes, HBV DNA, HBV RNA, and anti-HBe; HBeAg, HBsAg immune complexes, HBV DNA, HBV RNA, and anti-HBc; HBeAg, HBsAg immune complexes, HBV DNA, HBV RNA, and AST; HBeAg, HBsAg immune complexes, HBV DNA, HBV RNA, and ALT; HBeAg, HBsAg immune complexes, HBV DNA, HBcrAg, and HBeAg, HBsAg immune complexes, HBV DNA, HBcrAg, and anti-HBs; HBsAg immune complexes, HBV DNA, HBcrAg, and anti-HBs; HBeAg, HBsAg immune complexes, HBV DNA, HBcrAg, and anti-HBe; HBsAg immune complexes, HBV DNA, HBcrAg, and anti-HBc; HBeAg, HBsAg immune complexes, HBV DNA, HBcrAg, and AST; HBeAg, HBsAg immune complexes, HBV DNA, HBcrAg, and AST; HBeAg, HBsAg immune complexes, HBV DNA, HBcrAg, and ALT; HBeAg, an HBsAg immune complexes, HBV DNA, anti-HBc, AST; HBeAg, HBsAg immune complexes, HBV DNA, anti-HBe, and ALT; HBeAg, HBsAg immune complexes, HBV DNA, anti-HBc, and ALT; HBeAg, HBsAg immune complexes, HBV DNA, AST, and ALT; HBsAg immune complexes, HBV DNA, HBV RNA, HBcrAg, and anti-HBs; HBsAg immune complexes, HBV DNA, HBV RNA, HBcrAg, and anti-HBe; HBsAg immune complexes, HBV DNA, HBV RNA, HBcrAg, and anti-HBc; HBsAg immune complexes, HBV DNA, HBV RNA, HBcrAg, and AST; HBsAg immune complexes, HBV DNA, HBV RNA, HBcrAg, and ALT; HBsAg immune complexes, HBV DNA, HBV RNA, anti-HBs, and anti-HBe; HBsAg immune complexes, HBV DNA, HBV RNA, anti-HBs, and anti-HBc; HBsAg immune complexes, HBV DNA, HBV RNA, anti-HBs, and AST; HBsAg immune complexes, HBV DNA, HBV RNA, anti-HBs, and ALT; HBsAg immune complexes, HBV DNA, HBV RNA, anti-HBe, and AST; HBsAg immune complexes, HBV DNA, HBV RNA, anti-HBc, and AST; HBsAg immune complexes, HBV DNA, HBV RNA, anti-HBe, and ALT; HBsAg immune complexes, HBV DNA, HBV RNA, anti-HBc, and ALT; HBsAg immune complexes, HBV DNA, HBV RNA, AST, and ALT; HBeAg, HBsAg immune complexes, HBV DNA, HBV RNA, HBcrAg, and anti-HBs; HBeAg, HBsAg immune complexes, HBV DNA, HBV RNA, HBcrAg, and anti-HBe; HBeAg, HBsAg immune complexes, HBV DNA, HBV RNA, HBcrAg, and anti-HBc; HBeAg, HBsAg immune complexes, HBV DNA, HBV RNA, HBcrAg, and AST; HBeAg, HBsAg immune complexes, HBV DNA, HBV RNA, HBcrAg, and ALT; HBeAg, HBsAg immune complexes, HBV DNA, HBV RNA, anti-HBs, and anti-HBe; HBeAg, HBsAg immune complexes, HBV DNA, HBV RNA, anti-HBs, and anti-HBc; HBeAg, HBsAg immune complexes, HBV DNA, HBV RNA, anti-HBs, and AST; HBeAg, HBsAg immune complexes, HBV DNA, HBV RNA, anti-HBs, and ALT; HBeAg, HBsAg immune complexes, HBV DNA, HBV RNA, anti-HBe, and AST; HBeAg, HBsAg immune complexes, HBV DNA, HBV RNA, anti-HBc, and AST; HBeAg, HBsAg immune complexes, HBV DNA, HBV RNA, anti-HBe, and ALT; HBeAg, HBV DNA, HBV RNA, anti-HBc, and ALT; HBeAg, HBsAg immune complexes, HBV DNA, HBV RNA, AST, and ALT; HBsAg immune complexes, HBV DNA, HBV RNA, HBcrAG, anti-HBs, and anti-HBe; HBsAg immune complexes, HBV DNA, HBV RNA, HBcrAG, anti-HBs, and anti-HBc; anHBsAg immune complexes, HBV DNA, HBV RNA, HBcrAG, anti-HBs, and ALT; HBsAg immune complexes, HBV DNA, HBV RNA, HBcrAG, anti-HBe, and AST; HBsAg immune complexes, HBV DNA, HBV RNA, HBcrAG, anti-HBc, and AST; HBsAg immune complexes, HBV DNA, HBV RNA, HBcrAG, anti-HBe, and ALT; HBsAg immune complexes, HBV DNA, HBV RNA, HBcrAG, anti-HBc, and ALT; HBsAg immune complexes, HBV DNA, HBV RNA, HBcrAG, AST, and ALT; HBeAg, HBsAg immune complexes, HBV DNA, HBV RNA, HBcrAg, anti-HBs, and anti-HBe; HBeAg, HBsAg immune complexes, HBV DNA, HBV RNA, HBcrAg, anti-HBs, and anti-HBc; HBeAg, HBsAg immune complexes, HBV DNA, HBV RNA, HBcrAg, anti-HBs, and AST; HBeAg, HBsAg immune complexes, HBV DNA, HBV RNA, HBcrAg, anti-HBs, and ALT; HBeAg, HBsAg immune complexes, HBV DNA, HBV RNA, HBcrAg, anti-HBe, and AST; HBeAg, HBsAg immune complexes, HBV DNA, HBV RNA, HBcrAg, anti-HBc, and AST; HBeAg, HBsAg immune complexes, HBV DNA, HBV RNA, HBcrAg, anti-HBe, and ALT; HBeAg, HBsAg immune complexes, HBV DNA, HBV RNA, HBcrAg, anti-HBc, and ALT; HBeAg, HBsAg immune complexes, HBV DNA, HBV RNA, HBcrAg, ALT, and AST; HBsAg immune complexes, HBV DNA, HBV RNA, HBcrAg, anti-HBs, anti-HBe, and AST; HBsAg immune complexes, HBV DNA, HBV RNA, HBcrAg, anti-HBs, anti-HBc, and AST; HBsAg immune complexes, HBV DNA, HBV RNA, HBcrAg, anti-HBs, anti-HBe, and ALT; HBsAg immune complexes, HBV DNA, HBV RNA, HBcrAg, anti-HBs, anti-HBc, and ALT; HBeAg, HBsAg immune complexes, HBV DNA, HBV RNA, HBcrAg, anti-HBs, anti-HBe, and AST; HBeAg, HBsAg immune complexes, HBV DNA, HBV RNA, HBcrAg, anti-HBs, anti-HBc, and AST; HBeAg, HBsAg immune complexes, HBV DNA, HBV RNA, HBcrAg, anti-HBs, anti-HBe, and ALT; HBeAg, HBsAg immune complexes, HBV DNA, HBV RNA, HBcrAg, anti-HBs, anti-HBc, and ALT; HBsAg immune complexes, HBV DNA, HBV RNA, HBcrAg, anti-HBs, anti-HBe, AST, and ALT; HBsAg immune complexes, HBV DNA, HBV RNA, HBcrAg, anti-HBs, anti-HBc, AST, and ALT; HBeAg, HBsAg immune complexes, HBV DNA, HBV RNA, HBcrAg, anti-HBs, anti-HBe, AST, and ALT; HBeAg, HBsAg immune complexes, HBV DNA, HBV RNA, HBcrAg, anti-HBs, anti-HBc, AST, and ALT; HBsAg immune complexes and HBcAg; HBeAg, HBsAg immune complexes, and HBcAg; HBsAg immune complexes, HBV DNA, and HBcAg; HBsAg immune complexes, HBcAg, and anti-HBe; HBcAg, and anti-HBc; HBsAg immune complexes, HBcAg, and AST; HBeAg, HBsAg immune complexes, HBV RNA, and HBcAg; HBeAg, HBsAg immune complexes, HBV RNA, and HBcAg; HBeAg, HBsAg immune complexes, HBcAg, and anti-HBs; HBeAg, HBsAg immune complexes, HBcAg, and anti-HBe; HBeAg, HBsAg immune complexes, HBcAg, and anti-HBc; HBeAg, HBsAg immune complexes, HBcAg, and ALT; HBeAg, HBsAg immune complexes, HBcAg, and AST; HBsAg immune complexes, HBV DNA, HBV RNA, and HBcAg; HBsAg immune complexes, HBV RNA, HBcAg and ant-HBe; HBsAg immune complexes, HBV RNA, HBcAg and AST; HBsAg immune complexes, HBV RNA, HBcAg and ALT; HBsAg immune complexes, HBcAg, anti-HBs, and ant-HBe; HBsAg immune complexes, HBcAg, anti-HBs, and AST; HBsAg immune complexes, HBcAg, anti-HBs, and ALT; HBsAg immune complexes, anti-HBs, anti-HBe, and ALT; HBeAg, HBsAg immune complexes, HBV DNA, HBV RNA, and HBcAg; HBeAg, HBsAg immune complexes, HBV DNA, HBcAg, and HBeAg, HBsAg immune complexes, HBV DNA, HBcAg, and anti-HBs; HBeAg, HBsAg immune complexes, HBV DNA, HBcAg, and anti-HBe; HBeAg, HBsAg immune complexes, HBV DNA, HBcAg, and anti-HBc; HBeAg, HBsAg immune complexes, HBV DNA, HBcAg, and AST; HBeAg, HBsAg immune complexes, HBV DNA, HBcAg, and AST; HBeAg, HBsAg immune complexes, HBV DNA, HBcAg, and ALT; HBsAg immune complexes, HBV DNA, HBV RNA, HBcAg, and anti-HBs; HBsAg immune complexes, HBV DNA, HBV RNA, HBcAg, and anti-HBe; HBsAg immune complexes, HBV DNA, HBV RNA, HBcAg, and anti-HBc; HBsAg immune complexes, HBV DNA, HBV RNA, HBcAg, and AST; HBsAg immune complexes, HBV DNA, HBV RNA, HBcAg, and ALT; HBcAg, anti-HBs, anti-HBc, ALT, and AST; HBeAg, HBsAg immune complexes, HBV DNA, HBV RNA, HBcAg, and anti-HBs; HBeAg, HBsAg immune complexes, HBV DNA, HBV RNA, HBcAg, and anti-HBe; HBeAg, HBsAg immune complexes, HBV DNA, HBV RNA, HBcAg, and anti-HBc; HBeAg, HBsAg immune complexes, HBV DNA, HBV RNA, HBcAg, and AST; HBsAg immune complexes, HBV DNA, HBV RNA, HBcAg, anti-HBs, and anti-HBe;

HBsAg immune complexes, HBV DNA, HBV RNA, HBcAg, anti-HBs, and anti-HBc; HBsAg immune complexes, HBV DNA, HBV RNA, HBcAg, anti-HBs, and AST; HBsAg immune complexes, HBV DNA, HBV RNA, HBcAg, anti-HBs, and ALT; HBsAg immune complexes, HBV DNA, HBV RNA, HBcAg, anti-HBe, and AST; HBsAg immune complexes, HBV DNA, HBV RNA, HBcAg, anti-HBc, and AST; HBsAg immune complexes, HBV DNA, HBV RNA, HBcAg, AST, and ALT; HBeAg, HBsAg immune complexes, HBV DNA, HBV RNA, HBcAg, anti-HBs, and anti-HBe; HBeAg, HBsAg immune complexes, HBV DNA, HBV RNA, HBcAg, anti-HBs, and anti-HBc; HBeAg, HBsAg immune complexes, HBV DNA, HBV RNA, HBcAg, anti-HBs, and AST; HBeAg, HBsAg immune complexes, HBV DNA, HBV RNA, HBcAg, anti-HBs, and ALT; HBeAg, HBsAg immune complexes, HBV DNA, HBV RNA, HBcAg, anti-HBe, and AST; HBeAg, HBsAg immune complexes, HBV DNA, HBV RNA, HBcAg, anti-HBc, and AST; HBeAg, HBsAg immune complexes, HBV DNA, HBV RNA, HBcAg, anti-HBe, and ALT; HBeAg, HBsAg immune complexes, HBV DNA, HBV RNA, HBcAg, anti-HBc, and ALT; HBeAg, HBsAg immune complexes, HBV DNA, HBV RNA, HBcAg, ALT, and AST; HBsAg immune complexes, HBV DNA, HBV RNA, HBcAg, anti-HBs, anti-HBe, and AST; HBsAg immune complexes, HBV DNA, HBV RNA, HBcAg, anti-HBs, anti-HBc, and AST; HBsAg immune complexes, HBV DNA, HBV RNA, HBcAg, anti-HBs, anti-HBe, and ALT; HBsAg immune complexes, HBV DNA, HBV RNA, HBcAg, anti-HBs, anti-HBc, and ALT; HBeAg, HBsAg immune complexes, HBV DNA, HBV RNA, HBcAg, anti-HBs, anti-HBe, and AST; HBeAg, HBsAg immune complexes, HBV DNA, HBV RNA, HBcAg, anti-HBs, anti-HBc, and AST; HBsAg immune complexes, HBV DNA, HBV RNA, HBcAg, anti-HBs, anti-HBe, and ALT; HBsAg immune complexes, HBV DNA, HBV RNA, HBcAg, anti-HBs, anti-HBc, and ALT; HBsAg immune complexes, HBV DNA, HBV RNA, HBcAg, anti-HBs, anti-HBe, AST, and ALT; HBsAg immune complexes, HBV DNA, HBV RNA, HBcAg, anti-HBs, anti-HBc, AST, and ALT; HBeAg, HBsAg immune complexes, HBV DNA, HBV RNA, HBcAg, anti-HBs, anti-HBe, AST, and ALT; or HBeAg, HBsAg immune complexes, HBV DNA, HBV RNA, HBcAg, anti-HBs, anti-HBc, AST, and ALT are detected.

Other sub-combinations are specifically contemplated.

Exemplary detection methods are described below.

a. Detection of Nucleic Acid Markers

In some embodiments, markers are HBV DNA (including one or more splice variants of HBV DNA), and/or RNA. In some embodiments, HBV DNA or RNA markers are one or more of the presence of HBV DNA (including one or more splice variants) or RNA, the level (e.g., titer) of HBV DNA (including one or more splice variants) or RNA, the presence or absence of one or more mutations in the viral genome, and the genotype of HBV. Exemplary regions for use in detecting or characterizing HBV nucleic acids are described, for example, in U.S. Pat. Nos. 9,045,803, 7,015,317, 9,702,005, *Journal of Hepatology*, 2012. 57(1), and Hunt, C. M., et al., *Hepatology*, 2000. 31(5): p. 1037-44; each of which is herein incorporated by reference in its entirety.

Nucleic acid markers (e.g., HBV DNA or RNA) are detected using any suitable method. In some embodiments, RNA is detection by Northern blot analysis. Northern blot analysis involves the separation of RNA and hybridization of a complementary labeled probe.

In some embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, CA; Vee e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays are utilized for measuring marker mRNA levels. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be fabricated using a variety of technologies, including but not limited to: printing with fine-pointed pins onto glass slides; photolithography using pre-made masks; photolithography using dynamic micromirror devices; ink-jet printing; or, electrochemistry on microelectrode arrays.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, the markers are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., *Nonisotopic Probing, Blotting, and Sequencing*, ch. 17 (Larry J. Kricka ed., 2d ed. 1995, each of which is herein incorporated by reference in its entirety).

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through fluorometric detection means.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety.

By way of non-limiting example, probe binding pairs having interacting labels, such as those disclosed in U.S. Pat. No. 5,928,862 (herein incorporated by reference in its entirety) might be adapted for use in method of embodiments of the present disclosure. Probe systems used to detect single nucleotide polymorphisms (SNPs) might also be utilized in the present disclosure. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products methods of embodiments of the present disclosure. &e, e.g., U.S. Pat. No. 5,814,447 (herein incorporated by reference in its entirety).

In some embodiments, nucleic acid sequencing methods are utilized for detection (such as detection of HBV or in the case of one or more splice variants of HBV DNA, detection of HBV or hepatocellular carcinoma (HCC)).In some embodiments, the sequencing is Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, the sequencing is automated sequencing. In some embodiments, the sequencing is parallel sequencing of partitioned amplicons (PCT Publication No: WO2006084132 to Kevin McKernan et al., herein incorporated by reference in its entirety). In some embodiments, the sequencing is DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 *Science* 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382: U.S. Pat. Nos. 6,787,308; 6,833,246; herein incorporated by reference in their entireties), the Lynx massively parallel signature sequencing technology (Brenner et al. (2000). *Nat. Biotechnol.* 18:630-634; U.S. Pat. Nos. 5,695,934; 5,714,330; herein incorporated by reference in their entireties), and the Adessi PCR colony technology (Adessi et al. (2000). *Nucleic Acid Res.* 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding el al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, SS: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, SS: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, sequencing is nanopore sequencing (see, e.g., Astier et al., *J. Am. Chem. Soc.* 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, sequencing is HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

In some embodiments, sequencing is the technique developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, SS: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, the assays of the present disclosure measure HBV RNA, such as pgRNA. Measurement of HBV RNA, such as pgRNA, is a helpful marker, which, for example, can be employed to predict, e.g., (i) sustained loss of HBsAg without a HBV DNA increase after nucleos(t)ide analogue (NA) withdrawal in chronic hepatitis B (CHB) patients who have achieved HBsAg loss as a result of HBV therapeutic therapy; (ii) severe ALT flares after NA therapy withdrawal and/or (iii) HBeAg loss following novel siRNA therapies.

b. Detection of Protein Markers

In some embodiments, protein markers (e.g., HBV viral proteins or auto antibodies to such proteins, such as, for example, Hepatitis B e-antigen (HBeAg), Hepatitis B surface antigen (HBsAg), an isoform of HBsAg, Hepatitis B core antigen (HBcAg), Hepatitis B core-related antigen (HBcrAg), anti-Hepatitis B surface antigen antibody (anti-HBs), anti-Hepatitis B e-antigen antibody (anti-HBe), anti-Hepatitis B surface antigen antibody (anti-HBs) complexes formed between HBsAg an anti-HBs ("HBsAg immune complexes") are detected. In some embodiments, assays are quantitative or qualitative (e.g., detection of the marker or a specific variant of the marker).

Assays contemplated include immunoassays (such as sandwich and competitive immunoassays), clinical chemistry assays and enzymatic assays. Assays for determining polypeptide markers in a test sample obtained from a subject can comprise the steps of: (a) providing a test sample obtained from a subject; and (b) determining the concentration, presence, or status of one or more markers in the test sample. A specific type of assay that can be performed for determining is an immunoassay. Immunoassays can be conducted using any format known in the art, such as, but not limited to, a sandwich format, a competitive inhibition format (including both forward or reverse competitive inhibition assays) or in a fluorescence polarization format. As mentioned above, the immunoassay is in a sandwich format. Specifically, in one aspect of the present disclosure, at least two antibodies are employed to separate and quantify each of the markers in a test sample. More specifically, the at least two antibodies bind to certain epitopes of the markers forming an immune complex which is referred to as a "sandwich." Generally, in the immunoassays one or more antibodies can be used to capture the marker in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody", "detection antibodies", a "conjugate" or "conjugates"). In a sandwich assay, for example, both antibodies binding to the marker are not diminished by the binding of any other antibody in the assay to its respective binding site. In other words, antibodies should be selected so that the one or more first antibodies brought into contact with a test sample or test sample extract suspected of containing the marker do not bind to all or part of the binding site recognized by the second or subsequent antibodies, thereby interfering with the ability of the one or more second detection antibodies to bind to the marker.

In some embodiments, commercially available antibodies, which are well known in the art, are utilized.

The test sample being tested for (for example, suspected of containing) the marker can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing the marker is first brought into contact with an at least one first capture antibody under conditions which allow the formation of a first antibody-marker complex. If more than one capture antibody is used, a first multiple capture antibody-marker complex is formed. In a sandwich assay, the antibodies, such as the at least one capture antibody, are used in molar excess amounts of the maximum amount of marker expected in the test sample.

Optionally, prior to contacting the test sample with the at least one capture antibody (for example, the first capture antibody), the at least one capture antibody can be bound to a solid support or solid phase which facilitates the separation the first antibody-marker from the test sample. Any solid support known in the art can be used, including but not limited to, solid supports made out of polymeric materials in the forms of wells of a reaction tray, test tubes or beads (for example, polystyrene beads, magnetic beads), nitrocellulose strips, membranes, microparticles (for example, latex particles, sheep and DURACYTES® (Abbott Laboratories, Abbott Park, IL; DURACYTES® are red blood cells that have been "fixed" by pyruvic aldehyde and formaldehyde)).

The solid phase also can comprise any suitable porous material with sufficient porosity to allow access by detection antibodies and a suitable surface affinity to bind antigens. Microporous structures are generally used, but materials with gel structure in the hydrated state may be used as well. Such useful solid supports include, but are not limited to, nitrocellulose and nylon. Such porous solid supports are in the form of sheets of thickness from about 0.01 to 0.5 mm, including about 0.1 mm. The pore size may vary within wide limits, and can be from about 0.025 to about 15 microns, especially from about 0.15 to about 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces.

The antibody (or antibodies) can be bound to the solid support or solid phase by adsorption, by covalent bonding using a chemical coupling agent or by other means known in the art, provided that such binding does not interfere with the ability of the antibody to bind to the marker. Alternatively, the antibody (or antibodies) can be bound with microparticles that have previously coated with streptavidin or biotin (for example, using Power-Bind™-SA-MP streptavidin coated microparticles, available from Seradyn, Indianapolis, Indiana, with antibodies that have been biotinylated using means known in the art). Alternatively, the antibody (or antibodies) can be bound using microparticles that have been previously coated with anti-species specific monoclonal antibodies. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample being tested for and/or suspected of containing the marker is brought into contact with the at least one capture antibody (for example, the first capture antibody), the mixture is incubated in order to allow for the formation of a first antibody (or multiple antibody)-marker complex. The incubation can be carried out at a pH of from about 4.5 to about 10.0, at a temperature of from about 2° C. to about 45° C., and for a period from at least about one (1) minute to about eighteen (18) hours, including from about 1 to 20 minutes, also including from about 2-6 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody-marker complex, the complex is then contacted with at least one detection antibody (under conditions which allow for the formation of a (first or multiple) capture antibody-marker-(second or multiple) antibody detection complex). The at least one detection antibody can be the second, third, fourth, etc. antibodies used in the immunoassay. If the capture antibody-complex is contacted with more than one detection antibody, then a (first or multiple) capture antibody-marker detection antibody complex is formed. As with the capture antibody (e.g., the first capture antibody), when the at least second (and subsequent) detection antibody is brought into contact with the capture antibody-marker complex, a period of incubation under conditions similar to those described above is required for the formation of the (first or multiple) capture antibody-marker (second or multiple different markers) detection antibody complex. In some embodiments, at least one detection antibody contains a detectable label. The detectable label can be bound to the at least one detection antibody (e.g., the second detection antibody) prior to, simultaneously with or after the formation of the (first or multiple) capture antibody-marker (second or multiple) detection antibody complex. Any detectable label known in the art can be used. For example, the detectable label can be a radioactive label, such as, $^3H$, $^{125}I$, $^{35}S$, $^{14}C$, $^{32}P$, $^{33}P$, an enzymatic label, such as horseradish peroxidase, alkaline phosphatase, glucose 6-phosphate dehydrogenase, etc., a chemiluminescent label, such as, acridinium (e.g., acridium esters, acridinium SPSP (N10-(3-sulfopropyl)-N-(3-sulfopropyl, etc.), luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oregon.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, MO. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The (first or multiple) capture antibody-marker-(second or multiple) detection antibody complex can be, but does not have to be, separated from the remainder of the test sample prior to quantification of the label. For example, if the at least one capture antibody (e.g., the first capture antibody) is bound to a solid support or solid phase, such as, but not limited to, a well of a reaction tray, a bead or a microparticle, separation can be accomplished by removing the fluid (of the test sample) from contact with the solid support. Alternatively, if the at least first capture antibody is bound to a solid support it can be simultaneously contacted with the marker-containing sample and the at least one second detection antibody to form a first (multiple) antibody-marker antibody complex, followed by removal of the fluid (test sample) from contact with the solid support. If the at least one first capture antibody is not bound to a solid support, then the (first or multiple) capture antibody-marker (second or multiple) detection antibody complex does not have to be removed from the test sample for quantification of the amount of the label.

After formation of the labeled capture antibody-marker complex (e.g., the first capture antibody-marker complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of marker in the test sample is determined by use of a standard curve that has been generated using serial dilutions of the marker of known concentration. Other than using serial dilutions of the marker, the standard curve can be generated gravimetrically, by mass spectroscopy and by other techniques known in the art.

It goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is an ARCHITECT® diluent (Abbott Laboratories, Abbott Park, IL) containing 2-(N-morpholino)ethanesulfonic acid (MES), another salt, protein blockers, an antimicrobial and detergent. An exemplary calibrator diluent is ARCHITECT® calibrator diluent (Abbott Laboratories, Abbott Park, IL), which comprises a buffer containing MES, another salt, a protein blocker and an antimicrobial.

Furthermore, as previously mentioned, the methods and kits optionally are adapted for use on an automated or semi-automated system. Some of the differences between an automated or semi-automated system as compared to a non-automated system (e.g., ELISA) include the substrate to which the capture antibody is attached (which can impact sandwich formation and analyte reactivity), and the length and timing of the capture, detection and/or any optional wash steps. Whereas a non-automated format such as an ELISA may include a relatively longer incubation time with sample and capture reagent (e.g., about 2 hours) an automated or semi-automated format (e.g., ARCHITECT®) may have a relatively shorter incubation time (e.g., approximately 18 minutes for ARCHITECT®). Similarly, whereas a non-automated format such as an ELISA may incubate a detection antibody such as the conjugate reagent (Pb264) for a relatively longer incubation time (e.g., about 2 hours), an automated or semi-automated format (e.g., ARCHITECT®) may have a relatively shorter incubation time (e.g., approximately 4 minutes for the ARCHITECT®).

c. Detection of Enzymatic Markers

In some embodiments, the concentration of AST and/or ALT is detected (e.g., in combination with a marker described above). Such markers are generally detected using enzymatic assays in which the AST or ALT acts on a substrate to generate a detectable product (e.g., colorimetric product). In some embodiments, commercially available products are utilized (e.g., available from Abcam, Cambridge, MA or other sources). In some embodiments, Architect clinical chemistry analysis systems (Abbott, Abbott Park, IL) are utilized.

3. Monitoring, Prognosing, and Treating HBV

The compositions and methods described herein find use in determining a treatment for HBV, administering a treatment for HBV (such as, for example, administering one or more HBV therapeutics), monitoring treatment of HBV, and/or providing a prognosis to a subject diagnosed with HBV. Exemplary treatments (e.g., HBV therapeutics) include, but are not limited to, nucleos(t)ide analogue (e.g., lamivudine, adefovir, tenofovir, telbivudine, or entecavir), a nucleic acid (e.g., an siRNA, an antisense oligonucleotide, an shRNA, or a miRNA), an immunodulator (e.g., interferon alpha-2a or PEGylated interferon alpha-2a), a core protein assembly inhibitor (e.g., NVR 3-1983, GLS4, or BAY 41-4109), an HBsAg release inhibitor (e.g., REP 9 AC), an entry inhibitor (e.g., Myrcludex-B), or a combination thereof. In some embodiments, the assays of the present disclosure can be used to monitor the response of a subject receiving treatment for HBV with an anti-HBV agent (e.g., a HBV therapeutic). For example, if a subject exhibits markers indicative of higher levels of HBV viral nucleic acid or protein markers, the treatment may be altered (e.g., a different treatment or an increase dose of a drug may be administered). By way of another example, the assays of the present disclosure can be used to monitor for drug resistance of a subject receiving treatment for HBV with an HBV therapeutic. For example, it is known that the emergence of resistant strains with amino acid substitutions in the tyrosine-methionine-aspartate-aspartate (YMDD) motif of reverse transcriptase can be a serious problem for subjects receiving lamivudine therapy (see, e.g., Hatakeyama, T., et al., *Hepatology*, 45(5):1179-1186 (2007). The assays of the present disclosure can be used to monitor and/or predict the early emergence of mutants and/or drug resistance during HBV therapy. By way of another example, the assays of the present disclosure can be used to monitor or identify subjects at risk of developing one or more ALT flares and/or DNA reactivation after HBV therapy is removed, discontinued and/or withdrawn. For example, determining changes in levels (namely, one or more increases or decreases (such over one or more timepoints)) of one markers, such as for example, HBV RNA (such as HBV pgRNA), HBcrAg or combinations thereof, compared to one or more reference or predetermined levels (and determining whether said levels are favorable or unfavorable when compared to the predetermined or reference levels), can be used to identify or predict subjects at risk of developing one or more ALT flares and/or DNA activation once HBV therapy (such as therapy with one or more nucleos(t)ide analogues) is removed, discontinued and/or withdrawn.

In some embodiments, the presence, level, or status of a marker is used to optimize HBV treatment. For example, if a subject is found to have markers indicative of more virulent or aggressive or drug resistant infection, more aggressive treatment or a different drug may be administered. Conversely, if a subject is found to have markers indicative of a less virulent or aggressive infection, less aggressive treatment or monitoring (e.g., monitoring infections with no specific pharmaceutical treatment) may be chosen.

In some embodiments, monitoring or determining a treatment method (e.g., detection of markers) is repeated. In some embodiments, repeat monitoring generally is done with a specific timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition. In some embodiments, the monitoring or determining a treatment method (e.g., detection of markers) is continued and/or repeated until the subject (1) has obtained HBsAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (2) has obtained HBeAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (3) is negative for HBV DNA for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (4) demonstrates no evidence of liver injury based on ALT and/or AST levels for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; or (5) any combinations of (1)-(4). It is known in the art that a functional cure in chronic hepatitis B (CHB) patients involves one or more of a loss of HBsAg, undetectable HBV ongoing liver damage or a loss of HBsAg and undetectable HBV ongoing liver damage.

Embodiments of the present disclosure also include methods of treatment that combine the diagnostic methods described herein with literature-based treatments, protocols, analytics and combinations thereof to establish personalized treatment plans (such as individualized treatment regimens) for a subject in need of HBV therapy. In some embodiments, the methods of treatment of the present disclosure enable a prescribing physician to develop a personalized/individualized dosing regimen using one or more published mathematical models reflecting actual clinical data, without the loss of resolution in the data and/or model that results from distillation of the actual clinical data into a relatively coarsely stratified set of recommendations for an "average" or "typical" patient. Generally, the method involves assembling mathematical models developed from clinical data gathered from patients to whom a particular medication had been administered (e.g., an HBV therapeutic), processing the models to create a composite model rich in patient data, and determining patient-specific dosing regimens as a function of patient-specific observed response data processed in conjunction with data from the mathematical model(s). In some embodiments, the methods involve Bayesian averaging, Bayesian updating and Bayesian forecasting techniques to develop patient-specific dosing regimens as a function of not only generic mathematical models and patient-specific characteristics accounted for in the models as covariate patient factors, but also observed patient-specific responses that are not accounted for within the models themselves, and that reflect "between-subject variability" that distinguishes the specific patient from the typical patient reflected by the model. Examples of such models are described in U.S. Patent Publication No. 2014/0351197, the contents of which are herein incorporated by reference.

Typical models also describe the expected impact of specific patient characteristics, such as the results of a diagnostic test, on response, as well as quantify the amount of unexplained variability that cannot be accounted for solely by patient characteristics. In such models, patient characteristics are reflected as patient factor covariates within the mathematical model. Thus, the mathematical model is typically a mathematical function that describes underlying clinical data and the associated variability seen in the patient population. These mathematical functions include terms that describe the variation of an individual patient from the "average" or typical patient, allowing the model to describe or predict a variety of outcomes for a given dose and making the model not only a mathematical function, but also a statistical function, though the models and functions are referred to herein in a generic and non-limiting fashion as "mathematical" models and functions. It will be appreciated that many suitable mathematical models already exist and are used for purposes such as drug product development. Examples of suitable mathematical models describing response profiles for a population of patients and accounting for patient factor covariates include pharmacokinetic (PK) models, pharmacodynamic (PD) models, and exposure/response models, which are well known to those of skill in the art. Such mathematical models are typically published or otherwise obtainable from medication manufacturers, the peer-reviewed literature, and the FDA or other regulatory agencies. Alternatively, suitable mathematical models may be prepared by original research.

Embodiments of the present disclosure also contemplate continuing treatment in subjects currently receiving treatment with one or more HBV therapeutics in order to prevent or reduct the risk of DNA reactivation and/or relapse. In other embodiments, the assays of the present disclosure can be used to predict or determine whether a subject for whom treatment has been stopped (e.g., due to seroclearance), may have or has a potential relapse.

4. Biomarker Panels

Biomarkers of the present disclosure can be used in diagnostic tests to assess, determine, and/or qualify (used interchangeably herein) HBV status in a patient. The phrase "HBV status" includes any distinguishable manifestation of the condition, including not having HBV. For example, HBV status includes, without limitation, the presence or absence of an HBV infection in a patient, the risk of developing an HBV infection, the stage or severity of an HBV infection, the progress of an HBV infection (e.g., progress of an HBV infection over time), the effectiveness or response to treatment of an HBV infection (e.g., clinical follow up and surveillance of infection after treatment), and type of HBV infection. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. A ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

Analysis of the data described in the present disclosure, as well as clinical data from a cohort of HBV and control patients, resulted in the identification of HBV biomarkers that can be used individually, or in various combinations with each other and with other biomarkers in the form of a panel, to diagnose and/or evaluate an HBV infection in a subject. HBV biomarker panels may include any one of the HBV biomarkers disclosed herein, and may include more than one and up to 20 different biomarkers corresponding to distinct proteins. HBV biomarker panels can also include non-HBV biomarkers (e.g., assay control biomarkers), and biomarkers previously identified to be associated with HBV. In some embodiments, the biomarker panels of the present disclosure may show a statistical difference in different HBV statuses. Diagnostic tests that use these biomarkers may show an ROC of at least 0.6, at least about 0.7, at least about 0.8, or at least about 0.9.

HBV biomarkers can be differentially present/expressed depending on the type or subclass of HBV (e.g., an HBV signature) and, therefore, panels of more than one HBV biomarker can be useful in aiding in the determination of HBV status. In some embodiments, biomarkers are measured in a patient sample using the methods described herein and compared, for example, to predefined biomarker levels and correlated to HBV status. In some embodiments, the measurement(s) may then be compared with a relevant diagnostic amount(s), cut-off(s), reference levels, or multivariate model scores that distinguish a positive HBV status (e.g., seroconversion) from a negative HBV status (e.g., seroclearance). The diagnostic amount(s) represents a measured amount of a biomarker(s) above which or below which a patient is classified as having a particular HBV status. For example, if the biomarker(s) is/are unfavorable (e.g., increased) as compared to a control subject (e.g., a subject that has not sustained an HBV infection), then a measured amount(s) or levels above the diagnostic cutoff(s) or reference level can provide a diagnosis of HBV. Additionally, if the biomarker(s) is/are present during an HBV infection and not detectable in controls, then any detectably measured amount(s) can provide a diagnosis of an HBV infection. Alternatively, if the biomarker(s) is/are favorable (e.g., decreased) during HBV infection, then a measured amount(s) at or below the diagnostic cutoff(s) or reference level can provide a diagnosis of non-HBV infection. Additionally, if the biomarker(s) is/are not present during an HBV infection and are detectable in controls, then any detectably measured amount(s) can provide a diagnosis of non-HBV infection. As is well understood in the art, by adjusting the particular diagnostic cut-off(s) or reference level(s) used in an assay, one can increase sensitivity or specificity of the diagnostic assay depending on the preference of the diagnostician. In some embodiments, a particular diagnostic cut-off or reference levels can be determined, for example, by measuring the amount of biomarkers in a statistically significant number of samples from patients with the different HBV infection statuses, and drawing the cut-off to suit the desired levels of specificity and sensitivity.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present disclosure. In one embodiment of the present disclosure, the method used in a correlating a biomarker combination (e.g. to diagnose HBV status) is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 *J. OF COMPUTATIONAL AND GRAPHICAL STATISTICS* 475-511 (2003); Friedman, J. H., 84 J. OF THE AMERICAN STATISTICAL ASSOCIATION 165-75 (1989); Hastie, Trevor, Tibshirani, Robert, Friedman, Jerome, *The Elements of Statistical Learning*, Springer Series in Statistics (2001); Breiman, L., Friedman, J. H., Olshen, R. A., Stone, C. J. Classification and regression trees, California: Wadsworth (1984); Breiman, L., 45 *MACHINE LEARNING* 5-32 (2001); Pepe, M. S., *The Statistical Evaluation of Medical Tests for Classification and Prediction*, Oxford Statistical Science Series, 28 (2003); and Duda, R. O., Hart, P. E., Stork, D. G., Pattern Classification, Wiley Interscience, 2nd Edition (2001).

5. Methods of Assaying HBV Infections

In the methods described above, HBV biomarker levels can be measured by any means, such as antibody dependent methods, such as immunoassays, protein immunoprecipitation, immunoelectrophoresis, chemical analysis, SDS-PAGE and Western blot analysis, protein immunostaining, electrophoresis analysis, a protein assay, a competitive binding assay, a functional protein assay, or chromatography or spectrometry methods, such as high-performance liquid chromatography (HPLC), mass spectrometry, or liquid chromatography-mass spectrometry (LC/MS) or capillary electrophoresis (CE)-MS, or direct infusion, or any separating front end coupled with MS. Also, the assay can be employed in clinical chemistry format such as would be known by one skilled in the art.

HBV biomarker levels can also be measured by any means involving nucleic acid detection and/or amplification, such as but not limited to, polymerase chain reaction (PCR), reverse-transcriptase PCR (RT-PCR), real-time PCR, transcription-mediated amplification (TMA), rolling circle amplification, nucleic acid sequence based amplification (NASBA), strand displacement amplification (SDA), and ligase chain reaction (LCR).

a. Immunoassays

In some embodiments, measuring the level of an HBV biomarker includes contacting the sample with a first specific binding member and second specific binding member. In some embodiments the first specific binding member is a capture antibody and the second specific binding member is a detection antibody. In some embodiments, measuring the level of an HBV biomarker includes contacting the sample, either simultaneously or sequentially, in any order: (1) a capture antibody (e.g., an HBV biomarker-capture antibody), which binds to an epitope on an HBV biomarker or an HBV biomarker fragment to form a capture antibody-HBV biomarker antigen complex (e.g., HBV biomarker-capture antibody-HBV biomarker antigen complex), and (2) a detection antibody (e.g., HBV biomarker-detection antibody), which includes a detectable label and binds to an epitope on an HBV biomarker that is not bound by the capture antibody, to form an HBV biomarker antigen-detection antibody complex (e.g., HBV biomarker antigen-HBV biomarker-detection antibody complex), such that a capture antibody-HBV biomarker antigen-detection antibody complex (e.g., HBV biomarker-capture antibody-HBV biomarker antigen-HBV biomarker-detection antibody complex) is formed, and measuring the amount or concentration of an HBV biomarker in the sample based on the signal generated by the detectable label in the capture antibody-HBV biomarker antigen-detection antibody complex.

In some embodiments, the first specific binding member is immobilized on a solid support. In some embodiments, the second specific binding member is immobilized on a solid support. In some embodiments, the first specific binding member is an HBV biomarker antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instruments ARCHITECT®, Abbott Alinity instruments, and other core laboratory instruments) other than a point-of-care device may be capable of measuring levels of an HBV biomarker in a sample at about 0.032 µg/L at 10% CV or lower. Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is specifically contemplated, and includes mammalian host cells, because such eukaryotic cells (e.g., mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA*, 77: 4216-4220 (1980)), used with a DHFR selectable marker, e.g., as described in Kaufman and Sharp, *J. Mol. Biol.*, 159: 601-621 (1982), NSO myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells, or secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human troponin I) and the other heavy and light chain are specific for an antigen other than a human HBV biomarker by crosslinking an antibody to a second antibody by standard chemical crosslinking methods.

In some embodiments, a system for recombinant expression of an antibody, or antigen-binding portion thereof, includes a recombinant expression vector encoding both the antibody heavy chain and the antibody light chain that is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with an HBV biomarker or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad. Sci. USA,* 94:4937-4942; Hanes et al. (1998) *Proc. Natl. Acad. Sci. USA,* 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcook et al. (1996) *Proc. Natl. Acad. Sci. USA* 93:7843-7848); gel microdroplet and flow cytometry (Powell et al. (1990) Biotechnol. 8:333-337; One Cell Systems, (Cambridge, Mass).; Gray et al. (1995) *J. Imm. Meth.* 182:155-163; Kenny et al. (1995) Bio/Technol. 13:787-790); B-cell selection (Steenbakkers et al. (1994) *Molec. Biol. Reports* 19:125-134 (1994)).

An affinity matured antibody may be produced by any one of a number of procedures that are known in the art. For example, see Marks et al., *BioTechnology,* 10: 779-783 (1992) describes affinity maturation by VH and VL domain shuffling. Random mutagenesis of CDR and/or framework residues is described by Barbas et al., *Proc. Nat. Acad. Sci. USA,* 91: 3809-3813 (1994); Schier et al., Gene, 169: 147-155 (1995); Yelton et al., *J. Immunol.,* 155: 1994-2004 (1995): Jackson et al., *J. Immunol.,* 154(7): 3310-3319 (1995); Hawkins et al, *J. Mol. Biol.,* 226: 889-896 (1992). Selective mutation at selective mutagenesis positions and at contact or hypermutation positions with an activity enhancing amino acid residue is described in U.S. Pat. No. 6,914, 128 BI.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) *Plant Mol. Biol.* 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See, for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al., (1995) *Protein Eng.* 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, *pseudomonas* exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

b. Nucleic Acid Detection

The present disclosure includes materials and methods for amplifying and detecting HBV in a sample. HBV RNA and DNA levels can also be measured by any means involving nucleic acid detection and/or amplification, such as but not limited to, polymerase chain reaction (PCR), reverse-transcriptase PCR (RT-PCR), real-time PCR, transcription-mediated amplification (TMA), rolling circle amplification, nucleic acid sequence based amplification (NASBA), strand displacement amplification (SDA), and ligase chain reaction (LCR). The HBV genome is an enveloped DNA virus that belongs to the Hepadnaviridae family. It contains a small, partially double-stranded (DS), relaxed-circular DNA (rcDNA) genome that replicates by reverse transcription of an RNA intermediate, the pregenomic RNA (pgRNA). The HBV genome is between 3182 and 3248 base pairs (bp) depending on the genotype. The HBV genome encodes four overlapping open reading frames (ORFs) that are translated into viral core protein, surface proteins, polymerase/reverse transcriptase (RT), and Hepatitis B protein x (HBx). At least nine genotypes (A-I) and more than 24 subtypes of HBV have been identified globally.

Embodiments include the use of oligonucleotides to detect and/or amplify HBV RNA and DNA in a sample, including double- and single-stranded DNA, and double- and single-stranded RNA. Oligonucleotides for detecting HBV RNA and/or DNA include any nucleotide or polynucleotide equivalents or analogs of either RNA or DNA made from nucleotide analogs and modified polynucleotides such as, for example, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

In some embodiments, methods for detecting and/or amplifying HBV RNA and/or DNA in a sample are performed as part of evaluating a subject for an HBV infection or assessing efficacy of an HBV therapeutic. In some embodiments, methods for detecting and/or amplifying HBV RNA and/or DNA in a sample are performed as part of a clinical trial, including detecting HBV RNA as a primary or secondary endpoint for evaluating the efficacy of an HBV therapeutic. In some embodiments, methods for detecting and/or amplifying HBV RNA and/or DNA in a sample are performed in combination with other assays and assessments, including but not limited to, assessing HBV sAg status (e.g., negativity) and other tests for assessing seroconversion or seroclearance. By way of an example, methods for detecting and/or amplifying HBV RNA (such as HBV pgRNA) can be used to detect favorable and/or unfavorable changes in HBV RNA levels when compared to one or more predetermined or reference levels. In one aspect, an unfavorable or favorable change in the level of HBV RNA (such as in a subject receiving HBV therapy) when compared to one or more predetermined or reference levels can be used to predict and/or determine whether a subject has or is likely to achieve one or more of HBeAg loss or seroclearance, HBsAg loss or seroclearance, an isoform of HBsAg loss or seroclearance or combinations thereof.

Oligonucleotides that can be used to detect and/or amplify HBV RNA and DNA can be single-stranded or double-stranded, or can contain portions of both double-stranded and single-stranded sequences. Oligonucleotides can be DNA, both genomic and complimentary DNA (cDNA), RNA (e.g., pgRNA), or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Oligonucleotides can be obtained by chemical synthesis methods or by recombinant methods. A particular oligonucleotide sequence can encompass conservatively modified variants thereof (e.g., codon substitutions), alleles, orthologs, single nucleotide polymorphisms (SNPs), and complementary sequences as well as the sequence explicitly indicated.

Oligonucleotides are used in a variety of applications in biotechnology, such as, for example, artificial gene synthesis, as polymerase chain reaction (PCR) primers, in DNA sequencing, and as molecular probes. In one embodiment, the oligonucleotides described herein may be used as primers for nucleic acid amplification or as probes for nucleic acid hybridization and detection. Primers include oligonucleotides capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an agent for nucleic acid polymerization (e.g., a DNA-dependent or RNA-dependent polymerase). A primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. The primers of the present disclosure can be of any suitable size, and desirably comprise, consist essentially of, or consist of about 15 to 50 nucleotides, about 20 to 40 nucleotides, or about 22 to 30 nucleotides. For example, depending on the type of amplification process employed, primers can include, for example, a restriction endonuclease recognition site 5' to the target binding sequence (see, e.g., U.S. Pat. Nos. 5,270,184 and 5,455,166), or an RNA polymerase promoter linked to the target binding sequence of the primer. A "forward primer" is a primer that hybridizes (or anneals) to a target nucleic acid sequence (e.g., template strand) for amplification. A "reverse primer" is a primer that hybridizes (or anneals) to the complementary strand of the target sequence during amplification. A forward primer hybridizes with a target sequence 5' with respect to a reverse primer.

Probes include oligonucleotides that can selectively hybridize to at least a portion of a target sequence under appropriate amplification conditions (e.g., a portion of an HBV target sequence that has been amplified). In general, a probe sequence is identified as being either "complementary" (i.e., complementary to the coding or sense strand (+)), or "reverse complementary" (i.e., complementary to the anti-sense strand (−)). Probes can be of any suitable size, and desirably comprise, consist essentially of, or consist of about 10-50 nucleotides, about 12-35 nucleotides, or about 14-25 nucleotides.

Primer sets or probe sets include two or more oligonucleotides which together are capable of priming the amplification of a target sequence or target nucleic acid of interest (e.g., a target sequence within the HBV) and/or at least one probe which can detect the target sequence or target nucleic acid. In certain embodiments, a pair of primers includes a forward primer (or 5' (upstream) primer) that hybridizes with the 5'-end of the target sequence or target nucleic acid to be amplified and a reverse primer (or 3' (downstream) primer) that hybridizes with the complement of the target sequence or target nucleic acid to be amplified. Such primer sets or primer pairs are particularly useful in PCR amplification reactions.

Sets of oligonucleotides described herein may be used to amplify and/or detect a target HBV nucleic acid sequence in a sample. The terms "target sequence" and "target nucleic acid" are used interchangeably herein and refer to a specific nucleic acid sequence, the presence or absence of which is to be detected by the disclosed method. In the context of the present disclosure, a target sequence includes a nucleic acid sequence to which one or more primers will hybridize and from which amplification will initiate. The target sequence can also include a probe-hybridizing region with which a probe may form a stable hybrid under appropriate amplification conditions. A target sequence may be single-stranded or double-stranded. The primer and probe sequences described herein can target any suitable nucleic acid sequence, or combination of sequences, present in the HBV genome.

Oligonucleotides described herein may comprise, consist essentially of, or consist of any number of primer and probe oligonucleotides so as to amplify and detect any suitable number of HBV nucleic acid sequences. In one embodiment, the set of oligonucleotides described herein comprises, consists essentially of, or consists of two or more primers which amplify an HBV nucleic acid sequence comprising at least a portion of the HBV surface antigen gene to produce a single HBV amplicon, and at least two probes which hybridize to two different regions of the single HBV amplicon. A "portion" of a nucleic acid sequence comprises at least ten nucleotides (e.g., about 10 to about 5000 nucleotides). In some cases, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. As used herein, the term "amplicon" refers to a product of a natural or artificial amplification reaction. In one embodiment, for example, the first target HBV nucleic acid sequence comprises a highly conserved nucleic acid sequence comprising at least a portion of the HBV surface antigen gene.

In one embodiment, oligonucleotides described herein may comprise, consist essentially of, or consist of (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; and (d) a second probe oligonucleotide sequence comprising SEQ ID NO: 4 (also referred to as ALINITY$_m$™ HBV).

The set of oligonucleotides described herein may comprise a "dual-probe" design, in contrast to other commercially available HBV nucleic acid tests which utilize a single probe to detect and quantify HBV DNA (e.g., Abbott REAL-TIME™ HBV) (Abbott Molecular, Inc., Des Plaines, IL; COBAS® HBV for the COBAS® 4800 System (Roche Molecular Diagnostics, Pleasanton, CA); COBAS® HBV for the COBAS® 6800/8800 System (Roche Molecular Diagnostics, Pleasanton, CA; and VERIS/MDx® HBV Assay (Beckman Coulter, Inc., Brea, CA)). The turnaround time for sample preparation and real-time PCR for such "single-probe" detection systems can exceed 6 hours in some instances. In contrast, the amplification and detection methods described herein allow for sample-to-result analysis in approximately two and a half hours starting from a blood specimen. In addition, as discussed above, the set of oligonucleotides described herein enhances reliability of detection of multiple HBV genotypes, as the set amplifies and detects a highly conserved region of the HBV genome.

Any one or combination of the oligonucleotides described herein may be modified in any suitable manner so as to stabilize or enhance the binding affinity (also referred to as "melting temperature" or "$T_m$") of a primer or probe oligonucleotide for its target. In this respect, an oligonucleotide sequence as described herein may comprise one or more modified oligonucleotide bases. For example, the oligonucleotide sequence may comprise one or more propyne-modified bases, wherein the oligonucleotide comprises an alkyne with the chemical formula $CH_3C≡CH$. The one or more propyne-modified bases may include, for example, 5-(1-propynyl)-2'-deoxy-Uridine (pdU) and/or 5-(1-propynyl)-2'-deoxyCytidine (pdC).

Any one of the inventive oligonucleotide sequences described herein may comprise, consist essentially of, or consist of a complement of any of the sequences described herein. The terms "complement" or "complementary sequence," as used herein, refer to a nucleic acid sequence that forms a stable duplex with an oligonucleotide described herein via Watson-Crick base pairing rules, and typically shares about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater identity with the inventive oligonucleotide. Nucleic acid sequence identity can be determined using any suitable mathematical algorithm or computer software known in the art, such as, for example, CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are described in, for example, Altschul et al., *J. Molecular Biol.*, 215(3): 403-410 (1990); Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009); Soding, *Bioinformatics*, 21(7): 951-960 (2005); Altschul et al., *Nucleic Acids Res.*, 25(17): 3389-3402 (1997); and Gusfield, *Algorithms on Strings, Trees and Sequences*, Cambridge University Press, Cambridge UK (1997)).

The oligonucleotides described herein may be prepared using any suitable method, a variety of which are known in the art (see, for example, Sambrook et al., *Molecular Cloning. A Laboratory Manual*, 1989, 2. Supp. Ed., Cold Spring Harbour Laboratory Press: New York, N.Y.; M. A. Innis (Ed.), *PCR Protocols. A Guide to Methods and Applications*, Academic Press: New York, N.Y. (1990); P. Tijssen, *Hybridization with Nucleic Acid Probes—Laboratory Techniques in Biochemistry and Molecular Biology (Parts I and II)*, Elsevier Science (1993); M. A. Innis (Ed.), PCR Strategies, Academic Press: New York, N.Y. (1995); and F. M. Ausubel (Ed.), Short Protocols in Molecular Biology, John Wiley & Sons: Secaucus, N.J. (2002); Narang et al., *Meth. Enzymol.*, 68: 90-98 (1979); Brown et al., *Meth. Enzymol.*, 68: 109-151 (1979); and Belousov et al., *Nucleic Acids Res.*, 25: 3440-3444 (1997)). Primer pairs also can be designed using a variety of tools, such as the Primer-BLAST tool provided by the National Center of Biotechnology Information (NCBI). Oligonucleotide synthesis may be performed on oligo synthesizers such as those commercially available from Perkin Elmer/Applied Biosystems, Inc. (Foster City, CA), DuPont (Wilmington, DE), or Milligen (Bedford, MA). Alternatively, oligonucleotides can be custom made and obtained from a variety of commercial sources well-known in the art, including, for example, the Midland Certified Reagent Company (Midland, TX), Eurofins Scientific (Louisville, KY), BioSearch Technologies, Inc. (Novato, CA), and the like. Oligonucleotides may be purified using any suitable method known in the art, such as, for example, native acrylamide gel electrophoresis, anion-exchange HPLC (see, e.g., Pearson et al., *J. Chrom.*, 255: 137-149 (1983)), and reverse phase HPLC (see, e.g., McFarland et al., *Nucleic Acids Res.*, 7: 1067-1080 (1979)).

The sequence of the primers and probes can be verified using any suitable sequencing method known in the art, including, but not limited to, chemical degradation (see, e.g., Maxam et al., *Methods of Enzymology*, 65: 499-560 (1980)), matrix-assisted laser desorption ionization time-of-flight (MALDI-TOF) mass spectrometry (see, e.g., Pieles et al., *Nucleic Acids Res.*, 21: 3191-3196 (1993)), mass spectrometry following a combination of alkaline phosphatase and exonuclease digestions (Wu et al. *Anal. Biochem.*, 290: 347-352 (2001)), and the like.

The primer and probe oligonucleotides described herein desirably comprise a melting temperature ($T_M$) in the range 45° C. to 80° C. In accordance with the present disclosure, the oligonucleotides specifically hybridize to a target HBV nucleic acid sequence without exhibiting significant hybridization to non-HBV nucleic acids. In addition, the oligonucleotides are selected such that they hybridize to conserved regions in the HBV genome, thus minimizing mismatches with the target sequence. This selection ensures that the oligonucleotides are capable of hybridizing to HBV nucleic acids from all genotypes and subtypes. Furthermore, the oligonucleotides are selected such that they show the least likelihood of dimer formation and contain minimal sequence repeats. Such properties can be determined by methods known in the art, for example, using the computer modelling program OLIGO® Primer Analysis Software (distributed by National Biosciences, Inc., Plymouth, Minn.).

The present disclosure also provides a method for detecting hepatitis B virus (HBV) in a sample suspected of containing HBV. The method comprises: (a) contacting a sample obtained from a human with the set of oligonucleotide sequences described herein and reagents for amplification and detection of nucleic acid sequences, (b) amplifying a first target HBV nucleic acid sequence present in the sample, (c) hybridizing the first and second oligonucleotide probes to the first target HBV nucleic acid sequence, (d)

detecting hybridization of the first and second probe oligonucleotide sequences to the first target HBV nucleic acid sequence by assessing a signal from each of the detectable labels, whereby (i) the presence of the signals indicates hybridization of the first and second probe oligonucleotide sequences to the first target HBV nucleic acid sequence and the presence of HBV in the sample, and (ii) the absence of the signals indicates the absence of HBV in the sample. Descriptions of the primer and probe oligonucleotides set forth herein with respect to the aforementioned set of oligonucleotides also are applicable to those same aspects of the inventive method.

A sample, as defined herein, is "suspected" of containing HBV if the sample is obtained from a subject, preferably a human, suspected of being infected with HBV. A subject is suspected of being infected with HBV if the subject has an increased risk for HBV. An infant born to a mother infected with HBV is at a high risk of HBV infection. Other high-risk factors for HBV infection include, for example, intravenous drug use, hemophilia, high-risk sexual activity, hemodialysis, needle stick injury in health care staff, and body piercing and tattooing.

The sample can be any suitable sample obtained from any suitable subject, typically a mammal (e.g., a human). The sample may be obtained from any biological source, such as, a cervical, vaginal or anal swab or brush, or a physiological fluid including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and the like. The sample can be obtained from the subject using routine techniques known to those skilled in the art, and the sample may be used directly as obtained from the biological source or following a pretreatment to modify the character of the sample. Such pretreatment may include, for example, preparing plasma from blood, diluting viscous fluids, filtration, precipitation, dilution, distillation, mixing, concentration, inactivation of interfering components, the addition of reagents, lysing, etc.

After the sample is obtained from a subject, the sample may be contacted with the set of oligonucleotides comprising forward and reverse primers and first and second probes as described herein to form a reaction mixture. The reaction mixture is then placed under amplification conditions. The primers hybridize to a first target HBV nucleic acid sequence (e.g., at least a portion of the HBV surface antigen gene) if present in the sample, and a first target HBV nucleic acid sequence present in the sample is amplified. Amplifying an HBV nucleic acid sequence in the sample can be performed using any suitable nucleic acid sequence amplification method known in the art, including but not limited to, polymerase chain reaction (PCR), reverse-transcriptase PCR (RT-PCR), real-time PCR, transcription-mediated amplification (TMA), rolling circle amplification, nucleic acid sequence based amplification (NASBA), strand displacement amplification (SDA), and ligase chain reaction (LCR).

Because HBV comprises a DNA genome, amplification of the HBV virus nucleic acid sequence desirably is performed using PCR, and preferably real-time PCR, in which complimentary DNA (cDNA) fragments are synthesized from a substrate DNA template. The reaction typically involves the use of a synthetic oligonucleotide primer, which is complementary to nucleotide sequences in the substrate DNA, and the use of a DNA polymerase enzyme. The reaction consists of one cycle, in which the oligonucleotide primers, which are present in vast excess, hybridize to the substrate DNA to form double-stranded structures along complementary nucleotide sequences. The primer-substrate DNA:DNA complexes will then serve as initiation sites for a cDNA synthesis reaction catalyzed by DNA polymerase, resulting in the synthesis of a cDNA strand complementary to the DNA strand. "Real-time PCR," as used herein, refers to a PCR method in which the accumulation of amplification product is measured as the reaction progresses, in real time, with product quantification after each cycle, in contrast to conventional PCR in which the amplified DNA product is detected in an end-point analysis. Real-time PCR also is known in the art at "quantitative PCR (qPCR)." Real-time detection of PCR products typically involves the use of non-specific fluorescent dyes that intercalate with any double-stranded DNA and sequence-specific fluorescently-labeled DNA probes. Real-time PCR techniques and systems are known in the art (see, e.g., Dorak, M. Tevfik, ed. *Real-time PCR*. Taylor & Francis (2007); and Fraga et al., "Real-time PCR," Current protocols essential laboratory techniques: 10-3 (2008)) and are commercially available from a variety of sources (e.g., m2000rt REALTIME™ PCR system (Abbott Molecular, Inc., Des Plaines, IL); CFX Real-Time PCR Detection Systems (Bio-Rad Laboratories, Inc., Hercules, CA); and TAQMAN™ Real-Time PCR System (ThermoFisher Scientific, Waltham, MA)), any of which can be employed in the methods described herein.

In some embodiments, detection and/or quantification of HBV RNA can be performed (e.g., using the Abbott m2000sp/rt system) with an analytical sensitivity of approximately 100 U/mL using IVT RNA, with linear detection over 2-8 log U/mL range. In accordance with these embodiments, assays can be performed to discern HBV RNA from HBV DNA, including over the range of 2-6 log U/mL. In some embodiments, the HBV RNA assay limit of detection (LoD) and limit of quantitation (LoQ) can be determined. For example, the LoD and LoQ can range from 1-2 log U/mL.

Following amplification of an HBV virus nucleic acid sequence (e.g., at least a portion of the HBV surface antigen gene) that is present in the sample, the inventive method further comprises hybridizing the first and second probe oligonucleotides to the target HBV nucleic acid sequence. In one embodiment, a reaction mixture comprising an HBV amplicon may be contacted with the first and second oligonucleotide probes, as described herein, that preferentially hybridize to a target nucleic acid sequence of the amplicon, or the complement thereof, under stringent hybridization and wash conditions, thereby forming a hybrid duplex that is stable for detection. "Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Stringent hybridization conditions" as used herein means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of an oligonucleotide complementary to a target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. Any suitable method and conditions for hybridizing the first and second oligonucleotide probes to the target HBV nucleic acid sequence known in the art can be used in the inventive method.

Following hybridization of the first and second probe oligonucleotide sequences to the target HBV nucleic acid sequence, the method comprises detecting hybridization of the first and second probe oligonucleotide sequences to the target HBV nucleic acid sequence by assessing a signal from each of the detectable labels, whereby (i) the presence of the signals indicates hybridization of the first and second probe oligonucleotide sequences to the first target HBV nucleic acid sequence and the presence of HBV in the sample, and (ii) the absence of the signals indicates the absence of HBV in the sample. Detection of signals from the first and second probes may be performed using a variety of well-known methodologies, including, for example homogeneous or heterogeneous techniques.

Homogeneous detection methods involve detecting products of the amplification reaction as they are formed, namely, in a real-time manner. As a result, amplification product/probe hybrids are formed and detected while the reaction mixture is under amplification conditions. Homogeneous detection methods include, but are not limited to, the use of FRET labels that are attached to the probes and that emit a signal in the presence of the target sequence, Molecular Beacons (See, Tyagi et al., *Nature Biotechnol.*, 14: 303-308 (1996); Tyagi et al., *Nature Biotechnol.*, 16: 49-53 (1998); Kostrikis et al., *Science*, 279: 1228-1229 (1998); Sokol et al., *Proc. Natl. Acad. Sci. USA*, 95: 11538-11543 (1998); Marras et al., *Genet. Anal.*, 14: 151-156 (1999); and U.S. Pat. Nos. 5,846,726, 5,925,517, 6,277,581 and 6,235,504), TAQMAN® assays (see, e.g., U.S. Pat. Nos. 5,210,015; 5,804,375; 5,487,792 and 6,214,979 and International Patent Application Publication WO 01/86001), and hybridization protection assays (HPA) which utilize probes labeled with acridinium ester (AE) (see, e.g., Weeks et al., *Clin. Chem.*, 29: 1474-1479 (1983); Berry et al., *Clin. Chem.*, 34: 2087-2090 (1988)).

Heterogeneous detection systems generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the disclosure. Alternatively, a binding sequence may be complementary to a sequence of a capture oligonucleotide, itself comprising a sequence complementary to a tail sequence of a probe. After separation of the amplification product/probe hybrids bound to the capture agents from the remaining reaction mixture, the amplification product/probe hybrids can be detected using any suitable detection method known in the art or described herein.

c. Aptamers

The methods of the present disclosure include the use of aptamers to detect or identify one or more HBV biomarkers. Aptamers are suitable for use in developing probes having high affinity and selectivity for target molecules, such as HBV peptide biomarkers. Aptamers include single-stranded DNA (ssDNA), RNA, or modified nucleic acids, which have the ability to bind specifically to their targets, which range from small organic molecules to proteins and peptides. The basis for target recognition is the tertiary structures formed by the single-stranded oligonucleotides, as known in the art. In some embodiments, aptamers used to detect or identify one or more HBV biomarkers can be obtained through an in vitro selection process known as SELEX, in which aptamers are selected from a library of random sequences of synthetic DNA or RNA by repetitive binding of the oligonucleotides to target molecules.

In some embodiments, nucleic acids that constitute an aptamer library mixture used for screening for candidate HBV biomarker capture agents can be single-stranded DNA or RNA with or without chemical modifications. The introduction of additional chemical entities into DNA during the selection process can include, for example, the use of a 5-alkyne modified nucleobase, (e.g., thymine). Additionally, 5-C8-alkyne modified nucleotide-triphosphates, for example deoxythymidines, are commercially available or can be synthesized. Such 5-C8-alkyne modified nucleobases can be introduced into DNA by PCR Such modifications can be further derivatized with so called bio-orthogonal chemistry, for example, using the Cu(I) catalyzed 1,3-dipolar cycloaddition of respective azides with the alkyne. Beside the Cu(I) catalysed azide-alkyne cycloaddition (CuAAC), copper-free strain-promoted azide-alkyne cycloaddition (SPAAC) reactions also are useful. In some embodiments involving cellular or living systems, the strain-promoted azide-alkyne cycloaddition can overcome toxicity issues associated with the use of Cu(I). Any number of desirable chemical modifications can be added to the oligonucleotide library used for screening purposes. Examples of such modifications include without limitation aliphatic- aromatic-, charged-, basic-, acidic, heteroaromatic-, sugar-kind of-, metal-containing- or peptide-residues.

In some embodiments, a nucleobase that is to be modified to contain an azide-alkyne chemical group can include an ethynyl-, propynyl- or butynyl-dU, dA, dC or dG nucleotide. In other embodiments, a nucleobase that is to be modified to contain an azide-alkyne chemical group may be an ethynyl-dU nucleotide, or an ethynyl-dA nucleotide, an ethynyl-dC nucleotide or an ethynyl-dG nucleotide. Nucleotide aptamer libraries with these example modifications can be used in various SELEX-based selection methods, in order to enhance the chemical diversity of DNA aptamer libraries. The starting, or candidate, mixture of nucleic acids can be modified such that at least 25%, 30%, 35%, 40%0, 45%, 50%, 55%, 60%, 65%, 70%, 75%, 80%, 85%, 90%, 91%, 92%, 93%, 94%, 95%, 96%, 97%, 98%, at least 99%, or 100% of the members of the mixture are modified to comprise the functionalization introduced by click chemistry, for example. Less than 100% modification may allow for enhanced diversity by allowing certain positions in an oligonucleotide to be modified but not others, whereas 100% modification ensures consistency during the selection process. In some embodiments, different modifications are made at different positions in the oligonucleotide to further enhance diversity.

HBV biomarker-recognizing aptamers can be used in various methods to detect a presence or level of one or more HBV biomarker in a biological sample (e.g., biological entities of interest such as proteins, nucleic acids, or microvesicles). The aptamer can function as a binding agent or capture agent to assess presence or level of the cognate HBV biomarker. In various embodiments of the present disclosure directed to diagnostics and/or prognostics, one or more aptamers can be configured in a ligand-target based assay, where one or more aptamer can be contacted with a selected biological sample to allow the or more aptamer to associate with or binds to its target HBV biomarker molecule. Aptamers can also be used to identify a profile of multiple HBV biomarkers (a "biomarker" profile or signature) based on the biological samples assessed and biomarkers detected. A biomarker profile of a biological sample may comprise a presence, level or other characteristic of one or more biomarker of interest that can be assessed, including without limitation a presence, level, sequence, mutation, rearrangement, translocation, deletion, epigenetic modification, methylation, post-translational modification, allele, activity, complex partners, stability, half-life, and the like.

Biomarker profiles or signatures can be used to evaluate diagnostic and/or prognostic criteria such as presence of disease, disease staging, disease monitoring, disease stratification, or surveillance for detection, metastasis or recurrence or progression of disease. For example, methods of the present disclosure can include methods for correlating an HBV biomarker profile to a selected condition or disease. A biomarker profile can also be used clinically in making decisions concerning treatment modalities including therapeutic intervention. Biomarker profiles based on aptamer detection, identification, and/or quantification can further be used clinically to make treatment decisions, including whether to alter the course of treatment, such as administering a different HBV therapeutic to the subject.

d. Assay Variations

The disclosed methods of determining the presence or amount of analyte of interest (e.g., HBV biomarker) present in a sample may be as described herein. The methods may also be adapted in view of other methods for analyzing analytes. Examples of well-known variations include, but are not limited to, immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc.

i. Immunoassay

The analyte of interest, and/or peptides of fragments thereof (e.g., HBV biomarker and/or peptides or fragments thereof), may be analyzed using HBV biomarker antibodies in an immunoassay. The presence or amount of analyte (e.g., HBV biomarker) can be determined using antibodies and detecting specific binding to the analyte. For example, the antibody, or antibody fragment thereof, may specifically bind to the analyte. If desired, one or more of the antibodies can be used in combination with one or more commercially available monoclonal/polyclonal antibodies. Such antibodies are available from companies such as R&D Systems, Inc. (Minneapolis, MN) and Enzo Life Sciences International, Inc. (Plymouth Meeting, PA).

The presence or amount of analyte (e.g., HBV biomarker) present in a body sample may be readily determined using an immunoassay, such as sandwich immunoassay (e.g., monoclonal-monoclonal sandwich immunoassays, monoclonal-polyclonal sandwich immunoassays, including radioisotope detection (radioimmunoassay (RIA)) and enzyme detection (enzyme immunoassay (ETA) or enzyme-linked immunosorbent assay (ELISA) (e.g., Quantikine ELISA assays, R&D Systems, Minneapolis, MN)). An example of a point-of-care device that can be used is i-STAT® (Abbott, Laboratories, Abbott Park, IL). Other methods that can be used include a chemiluminescent microparticle immunoassay, including one employing the ARCHITECT® automated analyzer (Abbott Laboratories, Abbott Park, IL), as an example. Other methods include, for example, mass spectrometry, and immunohistochemistry (e.g., with sections from tissue biopsies), using anti-analyte (e.g., anti-HBV biomarker) antibodies (monoclonal, polyclonal, chimeric, humanized, human, etc.) or antibody fragments thereof against analyte (e.g., HBV biomarker). Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the analyte can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

A homogeneous format may be used. For example, after the test sample is obtained from a subject, a mixture is prepared. The mixture contains the test sample being assessed for analyte (e.g., HBV biomarker) and a specific binding partner. The order in which the test sample and the specific binding partner are added to form the mixture is not critical. The test sample is simultaneously contacted with the specific binding partner. In some embodiments, the specific binding partner and any HBV biomarker contained in the test sample may form a specific binding partner-analyte (e.g., HBV biomarker)-antigen complex. The specific binding partner may be an anti-analyte antibody (e.g., anti-HBV biomarker antibody that binds to an epitope having an amino acid sequence comprising at least three contiguous (3) amino acids of the HBV biomarker. Moreover, the specific binding partner may be labeled with or contains a detectable label as described above.

A heterogeneous format may be used. For example, after the test sample is obtained from a subject, a first mixture is prepared. The mixture contains the test sample being assessed for analyte (e.g., HBV biomarker) and a first specific binding partner, wherein the first specific binding partner and any HBV biomarker contained in the test sample form a first specific binding partner-analyte (e.g., HBV biomarker)-antigen complex. The first specific binding partner may be an anti-analyte antibody (e.g., anti-HBV biomarker antibody that binds to an epitope having an amino acid sequence comprising at least three contiguous (3) amino acids of the HBV biomarker. The order in which the test sample and the first specific binding partner are added to form the mixture is not critical.

The first specific binding partner may be immobilized on a solid phase. The solid phase used in the immunoassay (for the specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip. In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeOFe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte (e.g., HBV biomarker) antigen complex is formed, any unbound analyte (e.g., HBV biomarker) is removed from the complex using any technique known in the art. For example, the unbound analyte can be removed by washing. Desirably, however, the first specific binding partner is present in excess of any analyte present in the test sample, such that all analyte that is present in the test sample is bound by the first specific binding partner.

After any unbound analyte (e.g., HBV biomarker) is removed, a second specific binding partner is added to the mixture to form a first specific binding partner-analyte of interest (e.g., HBV biomarker)-second specific binding partner complex. The second specific binding partner may be an anti-analyte antibody (e.g., HBV biomarker antibody that binds to an epitope having an amino acid sequence comprising at least three contiguous (3) amino acids of the HBV biomarker. Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles (such as a magnetic bead), latex particles or modified surface latex particles, polymer or polymer film, plastic or plastic film, planar substrate, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

ii. Sandwich Immunoassay

A sandwich immunoassay measures the amount of antigen between two layers of antibodies (i.e., at least one capture antibody) and a detection antibody (i.e., at least one detection antibody). The capture antibody and the detection antibody bind to different epitopes on the antigen, e.g., analyte of interest such as a HBV biomarker). Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte (e.g., HBV biomarker) in a test sample. More specifically, the at least two antibodies bind to certain epitopes of analyte forming an immune complex which is referred to as a "sandwich." One or more antibodies can be used to capture the analyte in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing analyte do not bind to all or part of an epitope recognized by the second or subsequent antibodies, thereby interfering with the ability of the one or more second detection antibodies to bind to the analyte.

The antibodies may be used as a first antibody in said immunoassay. The antibody immunospecifically binds to epitopes on analyte (e.g., HBV biomarker). In addition to the antibodies of the present disclosure, said immunoassay may comprise a second antibody that immunospecifically binds to epitopes that are not recognized or bound by the first antibody.

A test sample suspected of containing analyte (e.g., HBV biomarker) can be contacted with at least one first capture antibody (or antibodies) and at least one second detection antibodies either simultaneously or sequentially. In the sandwich assay format, a test sample suspected of containing analyte is first brought into contact with the at least one first capture antibody that specifically binds to a particular epitope under conditions which allow the formation of a first antibody-analyte antigen complex. If more than one capture antibody is used, a first multiple capture antibody-HBV biomarker antigen complex is formed. In a sandwich assay, the antibodies, such as the at least one capture antibody, are used in molar excess amounts of the maximum amount of analyte expected in the test sample. For example, from about 5 μg/mL to about 1 mg/mL of antibody per ml of microparticle coating buffer may be used.

iii. Single Molecule Detection

The methods and kits as described herein may also involve single molecule counting. In certain embodiments, a method for analyte analysis may involve assessing an analyte present in a sample. In certain embodiments, the assessing may be used for determining presence of and/or concentration of an analyte in a sample. In certain embodiments, the method may also be used for determining presence of and/or concentration of a plurality of different analytes present in a sample.

Any device known in the art that allows for the detection of a single molecule of one or more analytes of interest can be used in the systems described herein. For example, the device can be a microfluidics device, digital microfluidics device (DMF), a surface acoustic wave based microfluidic device (SAW), an integrated DMF and analyte detection device, an integrated SAW and analyte detection device, or robotics based assay processing unit. Examples of other devices that can be used include the Quanterix SIMOA™

(Lexington, MA), Singulex's single molecule counting (SMC™) technology (Alameda, CA, see for example, U.S. Pat. No. 9,239,284, the contents of which are herein incorporated by reference), etc.

Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

The methods and kits as described herein can involve mass spectrometry using DIA-MS, DDA-MS or SRM/MRM-MS or PRM-MS. In certain embodiments, methods for analyte analysis can involve assessing a sample for the presence of an analyte. In certain embodiments, assessing a sample for the presence of an analyte can be used for determining presence of and/or concentration of an analyte or a fragment in a sample. In certain embodiments, a method can also be used for determining presence of and/or concentration of a plurality of different analytes or analyte fragments present in a sample. Quantification can be performed using internal control proteins or peptide fragments.

6. Samples

As used herein, "sample", "test sample", "biological sample" refer to fluid sample containing or suspected of containing an HBV biomarker. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing an HBV biomarker may be assayed directly. In one example, the source containing an HBV biomarker is a human bodily substance (e.g., bodily fluid, blood such as whole blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source containing an HBV biomarker is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source containing an HBV biomarker is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

It may be desirable to include a control. The control may be analyzed concurrently with the sample from the subject as described above. The results obtained from the subject sample can be compared to the results obtained from the control sample. Standard curves may be provided, with which assay results for the sample may be compared. Such standard curves present levels of marker as a function of assay units, i.e., fluorescent signal intensity, if a fluorescent label is used. Using samples taken from multiple donors, standard curves can be provided for reference levels of an HBV biomarker in normal healthy tissue, as well as for "at-risk" levels of the HBV biomarker in tissue taken from donors, who may have one or more of the characteristics set forth above.

Thus, in view of the above, a method for determining the presence, amount, or concentration of an HBV biomarker in a test sample is provided. The method comprises assaying the test sample for an HBV biomarker by an immunoassay, for example, employing at least one capture antibody that binds to an epitope on an HBV biomarker and at least one detection antibody that binds to an epitope on an HBV biomarker which is different from the epitope for the capture antibody and optionally includes a detectable label, and comprising comparing a signal generated by the detectable label as a direct or indirect indication of the presence, amount or concentration of an HBV biomarker in the test sample to a signal generated as a direct or indirect indication of the presence, amount or concentration of an HBV biomarker in a calibrator. The calibrator is optionally, and in some embodiments, is part of a series of calibrators in which each of the calibrators differs from the other calibrators in the series by the concentration of the HBV biomarker.

7. Kits and Systems

In some embodiments, the present disclosure further provides kits and systems for detecting the presence, level, or status of the above-named markers. In some embodiments, the kits or systems find use in multiplex and/or automated analysis methods. Exemplary reagents include, but are not limited to, nucleic acid primers, nucleic acid probes, antibodies, colorimetric reagents, enzymes, buffers, etc.

Optionally, the kit can also contain at least one calibrator or control. Any calibrator or control can be included in the kit.

Thus, the present disclosure further provides for diagnostic and quality control kits comprising one or more antibodies or other detection reagents. Optionally the assays, kits and kit components of the disclosure are optimized for use on commercial platforms (e.g., immunoassays on the Prism®, AxSYM®, ARCHITECT® and EIA (Bead) platforms of Abbott Laboratories, Abbott Park, IL, as well as other commercial and/or in vitro diagnostic assays). Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories, Abbott Park, IL) electrochemical immunoassay system. Immunosensors and methods of operating them in single-use test devices are described, for example, in U.S. Patent Applications 20030170881, 20040018577, 20050054078 and 20060160164 which are incorporated herein by reference. Additional background on the manufacture of electrochemical and other types of immunosensors is found in U.S. Pat. No. 5,063,081 which is also incorporated by reference for its teachings regarding same.

Optionally the kits include quality control reagents (for example, sensitivity panels, calibrators, and positive controls). Preparation of quality control reagents is well known in the art, and is described, e.g., on a variety of immunodiagnostic or nucleic acid product insert sheets.

In another embodiment, the present disclosure provides for a quality control kit comprising one or more antibodies described herein for use as a sensitivity panel to evaluate assay performance characteristics and/or to quantitate and monitor the integrity of the antigen(s) or nucleic acids used in the assay.

The kits can optionally include other reagents required to conduct a diagnostic assay or facilitate quality control evaluations, such as buffers, salts, enzymes, enzyme cofactors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The kit further can optionally include instructions for use, which may be provided in paper form or in computer-readable form, such as a disc, CD, DVD or the like.

The disclosure as described herein also can be adapted for use in a variety of automated and semi-automated systems (including those wherein the solid phase comprises a microparticle), as described, e.g., in U.S. Pat. Nos. 5,089, 424 and 5,006,309, and as, e.g., commercially marketed by Abbott Laboratories (Abbott Park, IL) including but not limited to Abbott's ARCHITECT®, AxSYM®, IMX, PRISM®, and Quantum II instruments, as well as other platforms. Moreover, the disclosure optionally is adaptable for the Abbott Laboratories commercial Point of Care (i-STAT™) electrochemical immunoassay system for performing sandwich immunoassays. Immunosensors, and their methods of manufacture and operation in single-use test devices are described, for example in, U.S. Pat. No. 5,063, 081, U.S. Patent Application 2003/0170881, U.S. Patent Application 2004/0018577, U.S. Patent Application 2005/ 0054078, and U.S. Patent Application 2006/0160164, which are incorporated in their entireties by reference for their teachings regarding same.

8. HBV Therapeutics

Therapeutic agents used to treat HBV include any of the following, as described further herein. Generally, the aim and/or ultimate goal of such therapeutic agents is to silence and/or eliminate cccDNA. Elimination of cccDNA can result in a functional cure in subjects suffering from HBV. Thus, a variety of therapeutic agents that are useful in silencing and/or eliminating cccDNA can be used in the methods described herein. In some embodiments, an HBV therapeutic includes tenofovir disoproxil fumarate, emtricitabine (Truvada®), adefovir, clevudine, ABX-203, lamivudine, PEG-IFNalpha, ABX-203, adefovir, PEG-IFNalpha and GBV-015. In some embodiments, an HBV therapeutic includes HBV DNA polymerase inhibitors such as besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009 and metacavir.

In some embodiments, an HBV therapeutic includes immunomodulators such as rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, polymer polyethyleneimine (PEI), Gepon, VGV-1, MOR-22, BMS-936559 and IR-103. In some embodiments, an HBV therapeutic includes toll-like receptor 7 modulators such as GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795. In some embodiments, an HBV therapeutic includes nucleic acid polymers (NAPs), such as, for example, REP 2139.

Toll-like receptor 8 modulators include motolimod, resiquimod, 3M-051, 3M-052, MCT-465, IMO-4200, VTX-763, VTX-1463. Toll-like receptor 3 modulators include rintatolimod, poly-ICLC, MCT-465, MCT-475, Riboxxon, Riboxxim and ND-1.1. Interferon alpha receptor ligands include interferon alpha-2b (Intron A®), pegylated interferon alpha-2a (Pegasys®), interferon alpha lb (Hapgen(®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (IFN), Multiferon®, interferon alfa-nl (Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B PDferon-B, interferon alfa-2b (IFN, Laboratories Biopro-farma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa).

Hyaluronidase inhibitors include astodrimer. HBsAg inhibitors include HBF-0259, PBHBV-001, PBHBV-2-15, PBHBV-2-1, REP 9 AC, REP-9C and REP 9AC. Toll like receptor 9 modulators include CYT003. Cyclophilin inhibitors include OCB-030, SCY-635 and NVP-018. HBV Prophylactic vaccines include Hexaxim, Heplisav, Mosquirix, DTwP-HBV vaccine, Bio-Hep-B, D,T/P/HBV,M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (Hansenual polymorpha yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Ka Shan6, rhHBsAG vaccine, and DTaP-rHB-Hib vaccine.

HBV Therapeutic vaccines include HBsAG-HBIG complex, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, TG-1050, NU-500, HBV ax, imTriGrid/antigen vaccine, Mega-CD40L-adjuvanted vaccine, HepB-v, NO-1800, recombinant VLP-based therapeutic vaccine (HBV infection, VLP Biotech), AdTG-17909, AdTG-17910 AdTG-18202, Chron-Vac-B, and Lm HBV.

HBV viral entry inhibitors include Myrcludex B. Antisense oligonucleotide targeting viral mRNA include ISIS-HBVRx. Interfering RNA, including short interfereing RNAs (siRNA) can be used. For example, siRNA that can be used include TKM-HBV(TKM-HepB), ALN-HBV, SR-008, ddRNAi and ARC-520. Endonuclease modulators include PGN-514. Inhibitors of ribonucleotide reductase include Trimidox. Hepatitis B virus E antigen inhibitors include wogonin. HBV antibodies targeting the surface antigens of the hepatitis B virus include GC-1102, XTL-17, XTL-19, XTL-001, K-003 and fully human monoclonal antibody therapy (hepatitis B virus infection, Humabs BioMed). HBV antibodies including monoclonal antibodies and polyclonal antibodies include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088). CCR2 chemokine antagonists include propagermanium. Thymosin agonists include Thymalfasin. Cytokines include recombinant IL-7, CYT-107, interleukin-2 (IL-2, Immunex); recombinant human interleukin-2 (Shenzhen Neptunus) and celmoleukin. Nucleoprotein inhibitors (HBV core or capsid protein inhibitors) include NVR-1221, NVR-3778, BAY 41-4109, morphothiadine mesilate and DVR-23. Stimulators of retinoic acid-inducible gene 1 include SB-9200, SB-40, SB-44, ORI-7246, ORI-9350, OR1-7537, ORI-9020, ORI-9198 and ORI-7170; (28) Stimulators of NOD2 selected from the group consisting of SB-9200. Recombinant thymosin alpha-1 include NL-004 and PEGylated thymosin alpha 1.

Hepatitis B virus replication inhibitors include isothiafludine, IQP-HBV, RM-5038 and Xingantie. PI3K inhibitors include idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401; (32) cccDNA inhibitors selected from the group consisting of BSBI-25.

PD-L1 inhibitors include MEDI-0680, RG-7446, durvalumab, KY-1003, KD-033, MSB-0010718C, TSR-042, ALN-PDL, STI-A1014 and BMS-936559. PD-1 inhibitors include nivolumab, pembrolizumab, pidilizumab, BGB-108 and mDX-400. BTK inhibitors include ACP-196, dasatinib, ibrutinib, PRN-1008, SNS-062, ONO-4059, BGB-3111, MSC-2364447, X-022, spebrutinib, TP-4207, HM-71224, KBP-7536 and AC-0025.

Other drugs for treating HBV include gentiopicrin (gentiopicroside), nitazoxanide, birinapant, NOV-205 (Molixan; BAM-205), Oligotide, Mivotilate, Feron, levamisole, Ka Shu Ning, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbama, IBPB-0061A, Hepuyinfen, DasKloster 0014-01, Jiangantai (Ganxikang), picroside, GA5 NM-HBV, DasKloster-0039, hepulantai, IMB-2613, TCM-800B, reduced glutathione and ZH-2N.

In some embodiments, an HBV therapeutic can be combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In one embodiment, an HBV therapeutic includes immunomodulators, toll-like receptor modulators (modulators of tlr1, tlr2, tlr3, tlr4, tlr5, tlr6, tdr7, tlr8, tdr9, tlr1 O, tlrl 1, tlr12 and tlr13), interferon alpha receptor ligands, hyaluronidase inhibitors, recombinant IL-7, HBsAg inhibitors, compounds targeting HbcAg, cyclophilin inhibitors, HBV therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBVcore or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD 137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), and Hepatitis B virus replication inhibitors.

In one embodiment, an HBV therapeutic includes HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2.

In one embodiment, an HBV therapeutic includes HBV viral entry inhibitors, NTCP inhibitors, HBx inhibitors, cccDNA inhibitors, HBVantibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In one embodiment, an HBV therapeutic includes immunomodulators, toll-like receptor modulators (modulators of tlr1, tlr2, tlr3, tlr4, tlr5, tlr6, tlr7, tlr8, tdr9, tlr10, tlr1, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In one embodiment, an HBV therapeutic includes adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-nl (Humoferon®), ribavirin, interferon beta-la (Avonex®), Bioferon, Ingaron, Inmutag (IFN), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin.

In some embodiments, combinations of one or more HBV therapeutics ("cocktails") can be used. Such combinations can be administered simultaneously or sequentially as part of treatment and can optionally be staggered over time with various combinations of HBV therapeutics. In some embodiments, a treating physician will develop or design an individualized treatment regimen (meaning a treatment regimen that is specific for that subject or patient) for a subject using one or more HBV therapeutics based on clinical parameters, cutoffs, publications or combinations thereof. In some embodiments, a treating physician will use an algorithm(s) designed to assess data relating to HBV treatment, as disclosed herein, as part of the development of an individualized treatment regimen for a subject. In some embodiments, the treatment being administered is part of a clinical trial. The treatment that is being administered as part of a clinical trial comprises a treatment regimen that has been designed or developed for one or more subjects or patients by a clinician or physician based on clinical parameters (such as, for example, those obtained from a prior clinical trial), cutoffs (such as, for example, those obtained from a prior clinical trial), patient profiles, publications or any combinations thereof.

9. Administration of Therapy

In some embodiments, the methods described herein can be used prior to or before treatment to select a subject or population of subjects that are believed to benefit or are likely to benefit from receiving one or more HBV therapeutics. For example, in some embodiments, methods for detecting and/or amplifying HBV RNA and/or DNA in a sample are performed as part of evaluating a subject having an HBV infection (e.g., determining the subject's state of disease or health) or assessing efficacy of an HBV therapeutic. In some embodiments, serum levels of HBV RNA (e.g., pgRNA) serve as a marker for HBV infection status and can therefore be used to evaluate or monitor treatment with one or more HBV therapeutics, including whether to initiate treatment, modify treatment, stop treatment, and/or add an additional treatment.

HBV RNA can be differentially present/expressed depending on the type or subclass of HBV, and how the virus is affected by one or more HBV therapeutics being administered. In some embodiments, multiple primers/probes are useful for detecting and/or amplifying HBV RNA and provide a more accurate diagnosis. In some embodiments, HBV RNA levels are measured in a patient sample using the methods described herein and compared, for example, to predefined HBV RNA levels and correlated to HBV status. In some embodiments, HBV RNA levels may then be compared with a relevant diagnostic amount(s), cut-off(s), or multivariate model scores that distinguish a positive HBV status (e.g., seroconversion) from a negative HBV status (e.g., seroclearance). The diagnostic amount(s) represents a measured amount of HBV RNA levels above which or below which a patient is classified as having a particular HBV status. For example, if HBV RNA levels is/are increased as compared to a control subject (e.g., a subject that does not have an HBV infection), then a measured amount(s) or levels above the diagnostic cutoff(s) can provide a diagnosis of HBV.

Additionally, if HBV RNA levels are present during an HBV infection and not detectable in controls, then any detectably measured amount(s) can provide a diagnosis of an HBV infection. Alternatively, if HBV RNA levels is/are decreased during an HBV infection, then a measured amount(s) at or below the diagnostic cutoff(s) can provide a diagnosis of non-HBV infection. As is well understood in the art, by adjusting the particular diagnostic cut-off(s) used in an assay, one can increase sensitivity or specificity of the diagnostic assay depending on the preference of the diagnostician. In some embodiments, a particular diagnostic cut-off can be determined, for example, by measuring the level of HBV RNA in a statistically significant number of samples from patients with the different HBV infection statuses, and drawing the cut-off to suit the desired levels of specificity and sensitivity.

In some embodiments, the present disclosure provides methods for characterizing HBV infection status based on the detection, non-detection, and/or detection of levels of HBV RNA. In one embodiment, the present disclosure provides methods for evaluating the development of HBV infection status in a patient over time, including progression (worsening) and regression (improvement), with or without administration of an HBV therapeutic. Over time, the amount or relative amount (e.g., the pattern or signature) of the HBV RNA levels may change as the disease progresses or as HBV treatment becomes effective. Therefore, the trend of HBV RNA levels, either towards seroconversion or seroclearance, can indicate the course of the infection. Accordingly, methods can include measuring HBV RNA levels in a patient at at least two different time points (e.g., a first time and a second time), and comparing the changes, if any.

In some embodiments, data that are generated using samples (such as known samples) can be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., HBV infected or non-infected).

Classification models can be formed using any suitable statistical classification or learning method that attempts to segregate bodies of data into classes based on objective parameters present in the data. Classification methods may be either supervised or unsupervised. Supervised and unsupervised classification processes are well known in the art, such as, for example, those described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Details about recursive partitioning processes are well known in the art and can be found, for example in U.S. Patent Application No. 2002/0138208.

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm, all of which are well known in the art.

Learning algorithms asserted for use in classifying biological information are described, for example, in PCT International Publication No. WO 01/31580, U.S. Patent Application Publication No. 2002/0193950, U.S. Patent Application Publication No. 2003/0004402 and U.S. Patent Application Publication No. 2003/0055615, all of which are herein incorporated by reference.

The classification models can be formed on and used on any suitable digital computer. Suitable digital computers include micro, mini, or large computers using any standard or specialized operating system, such as a Unix, Windows® or Linux™ based operating system. The training data set and the classification models according to embodiments of the disclosure can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc. The learning algorithms described above are useful both for developing classification algorithms, which can form the base for diagnostic tests by providing diagnostic values (e.g., cut-off points) for HBV RNA levels used singly or in combination with other clinical readouts or assays.

Embodiments of the present disclosure include treating or monitoring a subject identified or assessed as having HBV (e.g., chronic HBV) based on detecting or measuring HBV RNA (e.g., HBV pgRNA). In some embodiments, the method includes treating a human subject assessed as having an HBV infection with a therapeutic treatment, which can take a variety of forms depending on the severity of the infection (e.g., nucleos(t)ide analogs (e.g., lamivudine, entecavir, tenofovir), pegylated interferon). In some embodiments, the method includes monitoring HBV RNA levels of the human subject assessed as having an HBV infection to determine if treatment with the HBV therapeutic is effective. For example, in the context of chronic HBV, treatment with nucleos(t)ide analogs suppress HBV DNA synthesis, but does not affect synthesis of HBV pgRNA. Therefore, HBV RNA in serum or plasma can be used as a marker for HBV cccDNA activity and can be used to monitor a subject and/or determine the efficacy of an HBV therapeutic.

In some embodiments, the present disclosure provides methods for determining whether to initiate treatment with an HBV therapeutic based on the levels of HBV RNA in the subject. The risk of developing one or more characteristics of an HBV infection can be determined by measuring the HBV RNA and then either submitting them to a classification algorithm or comparing them with a reference amount (e.g., a predefined level or signature that is associated with the particular risk level).

In some embodiments, treating a subject diagnosed as HBV positive can include managing patient treatment based on HBV status or severity as established using one or more assays or clinical assessments. Such management can include the actions of the physician or clinician subsequent to determining HBV status. For example, if a physician diagnoses a subject as having an acute HBV infection, then a certain schedule/regimen of treatment would be administered, and the subject's progress would be monitored based on HBV RNA levels at certain cutoffs and timepoints. If a physician diagnoses a subject as having a chronic HBV infection, then a different schedule/regimen of treatment would be administered, and the subject's progress would be monitoring based on HBV RNA levels at different cutoffs and timepoints. For example, guidelines have been developed by the American Association for the Study of Liver Diseases, the European Association for the Study of Liver and the Asian Pacific Association for the Study of the Liver to provide treatment guidelines to provide healthcare professionals with guidance on the management of chronic HBV infections. These guidelines provide recommendations on who should be treated, what to treat with, how to monitor, when to stop therapy and management of treatment failure (See, Ghany, M. G., *Best Practice & Research Clinical Gastroenterology*, 31(3):299-309 (2017)). Alternatively, a physician may use new or recent information in the scientific literature and/or reported in clinical trials to design a schedule, regimen or course of treatment other than those recognized as the standard of care or provided in recommended treatment guidelines (and which may not yet be approved by a regulatory agency such as the FDA or EMA) to treat a subject having acute or chronic HBV infection. Such schedule, regimen or course of treatment can be considered to be an "unconventional" treatment.

In some embodiments, the present disclosure provides methods for determining the efficacy of an HBV therapeutic drug, composition or treatment based on HBV RNA levels. These methods can be useful in performing clinical trials of a drug, as well as monitoring the progress of a patient on a drug. Therapy or clinical trials involve administering an HBV therapeutic according to a particular regimen or protocol. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or signature) of HBV RNA may change toward an improved outcome (e.g., functional cure of chronic HBV).

In accordance with these embodiments, the method may involve measuring or detecting HBV RNA in a subject receiving HBV treatment, and correlating the HBV RNA levels with HBV status of the subject (e.g., by comparison to predefined or pre-determined HBV RNA levels). One embodiment of this method can involve determining HBV RNA levels at at least two different time points during a course of treatment (e.g., a first time and a second time), and comparing the change in levels of the HBV RNA, if any. For example, the levels of HBV RNA can be measured before and after treatment administration or at two different time points during treatment administration. The effect of treatment is determined based on these comparisons. If a treatment is effective, then the HBV RNA will trend toward an improved outcome and the treatment will continue at that particular schedule/regimen. In some cases, the method may involve altering the particular treatment schedule/regimen to include a shorter duration of treatment or a reduced dosage, which reflects the subject's improvement and reduced dependency on the treatment to achieve a favorable outcome (e.g., seroclearance). In some cases, the treatment can be stopped (e.g., due to seroclearance), and the subject's HBV RNA levels can be monitored periodically to predict or determine a potential relapse. If treatment is ineffective, the HBV RNA will trend toward a worse outcome or an unchanged outcome, and one or more aspects of the treatment will need to be adjusted. For example, in the case of worsening outcomes or unchanged outcomes, the method may involve stopping the current course of treatment and/or administering a different or additional HBV therapeutic, and/or increasing treatment duration, and the subject's HBV RNA levels can be monitored to assess the efficacy of these changes in treatment. Moreover, in some cases, a decrease or decline in the level of HBV RNA (such as in a subject receiving HBV therapy with at least one HBV therapeutic) and optionally, one or more additional markers (such as, for example, one or more anti-HBs antibodies, one or more anti-HBe antibodies, one or more anti-HBc antibodies or combinations thereof) over at least two or more time points levels can be used to predict and/or determine whether a subject has or is likely to achieve one or more of HBeAg loss or seroclearance, HBsAg loss or seroclearance, an isoform HBsAg loss or seroclearance or combinations thereof. Further, in some cases, a decrease or decline in the level of HBV RNA and optionally, one or more additional markers (such as, for example, HBcrAg), can be used to predict whether or not a subject is likely to experience once or more ALT flares if treatment with the HBV therapeutic is withdrawn, removed or discontinued.

In some embodiments, methods for detecting and/or amplifying HBV RNA and/or DNA in a sample include discerning between HBV DNA and HBV RNA in order to determine, for example, HBV status in an individual. For example, in the context of chronic HBV, treatment with nucleos(t)ide analogues can lead to the suppression of HBV DNA synthesis, but not the suppression of HBV RNA (pgRNA), while a lack of treatment leads to high levels of HBV DNA as compared to HBV RNA levels. Therefore, if an individual subject who is receiving HBV treatment has levels of HBV DNA that are elevated compared to HBV RNA levels, then this can indicate that the treatment is not effective. In accordance with these embodiments, an alternative course of treatment may be warranted.

In accordance with the above methods of administering and/or monitoring HBV treatment, HBV RNA levels or changes in HBV RNA levels can be determined based on a standard and/or based on cutoff levels, such as specified levels of HBV RNA (e.g., Units/mL) in plasma or serum of peripheral blood). For example, a standard level of HBV RNA can be based on the WHO HBV DNA standard (such as, for example, the WHO International Standard 4th WHO International Standard for HBV DNA for NAT: NIBSC code: 10/266) as it applies to RNA (1U of RNA=1 IU of HBV DNA) In some embodiments, this HBV RNA standard can be augmented or replaced with a different standard based on additional clinical assessments and/or empirical assessment of an individual subject, or a collection of subjects (e.g., a database of HBV RNA levels reflecting different clinical parameters).

In some embodiments, the present disclosure provides methods for selecting an HBV patient population that would be likely to benefit from a particular HBV therapeutic and/or treatment regimen. In accordance with these embodiments, the method includes assessing baseline levels of HBV RNA in these subjects and correlating these baseline levels with one or more parameters that reflect the clinical conditions of the subjects (e.g., seroconversion, age, etc.). In some embodiments, subjects having HBV RNA levels at or above a particular level will be more likely to benefit from clinical intervention. In other embodiments, subjects having HBV RNA levels at or below a particular level will not require clinical intervention, but their HBV RNA levels may continue to be monitored. In some embodiments, HBV RNA levels can be used to stratify patient populations and generate risk profiles to assess a subject for the risk of developing one or more clinical manifestations of an HBV infection, which can be correlated with various treatment options.

All patents and publications mentioned in the specification are indicative of the levels of those skilled in the art to which the disclosure pertains. All patents and publications are herein incorporated by reference to the same extent as if each individual publication was specifically and individually indicated to be incorporated by reference.

The disclosure illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure includes various embodiments and optional features, modification and variation of the concepts herein disclosed may be resorted to by those skilled in the art, and that such modifications and variations are considered to be within the scope of this disclosure as defined by the appended claims.

For reasons of completeness, various aspects of the disclosure are set out in the following numbered clauses:

Clause 1. A method of assessing and monitoring disease stage or phase, predicting likelihood of disease progression, or predicting or monitoring response to a Hepatitis B (HBV) therapy, the method comprising the steps of: (a) contacting a test sample obtained from a subject being administered a treatment for HBV or diagnosed with HBV with reagents for detection of the presence, level, or status of one or more markers selected from the group consisting of Hepatitis B e-antigen (HBeAg), Hepatitis B surface antigen (HBsAg), an isoform of HBsAg, Hepatitis B core antigen (HBcAg), HBV DNA, one or more HBV DNA splice variants, HBV RNA, Hepatitis B core-related antigen (HBcrAg), anti-Hepatitis B surface antigen antibodyanti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), and aspartate aminotransferase (AST); and (b) assessing and monitoring disease stage or phase, predicting likelihood of disease progression, or predicting or monitoring response to a Hepatitis B (HBV) therapy based on the presence, level, or status of said one or more markers.

Clause 2. A method of detecting the presence, level, or status of one or more markers, comprising: (a) contacting a test sample obtained from a subject being administered a treatment for HBV or diagnosed with HBV with reagents for detection of the presence, level, or status of one or more markers selected from the group consisting of Hepatitis B e-antigen (HBeAg), Hepatitis B surface antigen (HBsAg), an isoform of HBsAg, Hepatitis B core antigen (HBcAg), HBV DNA, one or more HBV DNA splice variants, HBV RNA, Hepatitis B core-related antigen (HBcrAg), anti-Hepatitis B surface antigen antibodyanti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), and aspartate aminotransferase (AST); and (b) determining the presence, level, or status of said one or more markers.

Clause 3. A method of treating HBV, comprising: (a) contacting a test sample obtained from a subject diagnosed with HBV with reagents for detection of the presence, level, or status of one or more markers selected from the group consisting of Hepatitis B e-antigen (HBeAg), Hepatitis B surface antigen (HBsAg), an isoform of HBsAg, Hepatitis B core antigen (HBcAg), HBV DNA, one or more HBV splice variants, HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), and aspartate aminotransferase (AST): (b) identifying a treatment for HBV based on said presence, level, or status of said one or more markers; and (c) administering said treatment.

Clause 4. The method of clauses 1 or 2, wherein said method further comprises administering a treatment for HBV to said subject.

Clause 5. The method of any one of claims 1 to 4, wherein said treatment is selected from the group consisting of an interferon, a nucleos(t)ide analogue, a nucleic acid, an immunodulator, a core protein assembly inhibitor, an HBsAg release inhibitor, interfering RNA, an entry inhibitor, and a combination thereof.

Clause 6. The method of clause 5, wherein said interferon is selected from the group consisting of interferon alpha-2a and PEGylated interferon alpha-2a.

Clause 7. The method of clause 5, wherein said nucleos(t)ide analogue is selected from the group consisting of lamivudine, adefovir, tenofovir, telbivudine, and entecavir.

Clause 8. The method of clause 5, wherein said nucleic acid is selected from the group consisting of an siRNA, an antisense oligonucleotide, an shRNA, and a miRNA.

Clause 9. The method of clause 5, wherein said core protein assembly inhibitor is selected from the group consisting of NVR 3-1983, GLS4 and BAY 41-4109.

Clause 10. The method of clause 5, wherein said HBsAg release inhibitor is REP 9 AC.

Clause 11. The method of clause 5, wherein said entry inhibitor is Myrcludex-B.

Clause 12. The method of any one of clauses 1 to 11, wherein said reagent is selected from the group consisting of a plurality of nucleic acid primers that specifically hybridize to HBV DNA or RNA, a plurality of nucleic acid probes that specifically hybridize to HBV DNA or RNA, an antibody that specifically binds to an HBV protein, and reagents for enzymatic detection of ALT and/or AST.

Clause 13. The method of any one of clauses 1 to 12, wherein said method further comprises altering said treatment of HBV based on said presence, level, or status of said one or more markers.

Clause 14. The method of clause 13, wherein said altering is selected from the group consisting of starting, stopping, or changing said treatment.

Clause 15. The method of any one of clauses 1 to 14, wherein said one or more markers comprises 3 or more markers.

Clause 16. The method of any one of clauses 1 to 14, wherein said one or more markers comprises 5 or more markers.

Clause 17. The method of any one of clauses 1 to 16, wherein said method further comprises repeating said method one or more times.

Clause 18. The method of any one of clauses 1 to 17, wherein the method is adapted for use in an automated system or semi-automated system.

Clause 19. A kit or system, comprising: reagents for detection of the presence, level, or status of one or more markers selected from the group consisting of Hepatitis B e-antigen (HBeAg), Hepatitis B surface antigen (HBsAg), an isoform of HbsAg, Hepatitis B core antigen (HBcAg), HBV DNA, one or more HBV splice variants, HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), and aspartate aminotransferase (AST).

Clause 20. The kit or system of clause 19, wherein said kit or system further comprises software and a processor for analyzing said presence, level, or status of said one or more markers and providing an assessment of disease stage or phase, a prediction of likelihood of disease progression, or a prediction of a response to a Hepatitis B (HBV) therapy.

Clause 21. The kit or system of clauses 19 or 20, wherein said reagent is selected from the group consisting of a plurality of nucleic acid primers that specifically hybridize to HBV DNA or RNA, a plurality of nucleic acid probes that specifically hybridize to HBV DNA or RNA, an antibody that specifically binds to an HBV protein, and reagents for enzymatic detection of ALT and/or AST.

Clause 22. The kit of any one of clauses 19 to 21, wherein said one or more markers comprises 3 or more markers.

Clause 23. The kit or system of any one of clauses 19 to 21, wherein said one or more markers comprises 5 or more markers.

Clause 24. The use of reagents for detection of the presence, level, or status of one or more markers selected from the group consisting of Hepatitis B e-antigen (HBeAg), Hepatitis B surface antigen (HBsAg), an isoform of HbsAg, Hepatitis B core antigen (HBcAg), HBV DNA, one or more HBV splice variants, HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs (also referred to herein as "HBsAg immune complexes"), alanine aminotransferase (ALT), and aspartate aminotransferase (AST) to provide an assessment of disease stage or phase, a prediction of likelihood of disease progression, or a prediction of a response to a Hepatitis B (HBV) therapy.

Clause 25. A method of assessing efficacy of treatment with a Hepatitis B virus (HBV) therapeutic in a subject suffering from a chronic HBV infection, the method comprising:
  (a) performing an assay on a sample obtained from the subject to detect or measure a level of at least one HBV antigen biomarker, at least one HBV genomic biomarker, or at least one HBV antigen marker and at least one HBV genomic biomarker; and
  (b) determining whether seroclearance has been achieved by comparing the level of the at least one HBV antigen biomarker, the at least one HBV genomic biomarker, or the at least one HBV antigen marker and the at least one HBV genomic biomarker to a reference level of the at least one HBV antigen biomarker, the at least one HBV genomic biomarker, or the at least one HBV antigen marker and the at least one HBV genomic biomarker;
  wherein:
    (i) the treatment is determined not to be efficacious if the level of the at least one HBV antigen biomarker, the at least one HBV genomic biomarker, or the at least one HBV antigen marker and the at least one HBV genomic biomarker is unfavorable when compared to the reference level of the at least one HBV antigen biomarker, the at least one HBV genomic biomarker, or the at least one HBV antigen marker and the at least one HBV genomic biomarker; or
    (ii) the treatment is determined to be efficacious if the level of the at least one HBV antigen biomarker, the at least one HBV genomic biomarker, or the at least one HBV antigen marker and the at least one HBV genomic biomarker is favorable when compared to the reference level of the at least one HBV antigen biomarker, the at least one HBV genomic biomarker, or the at least one HBV antigen marker and the at least one HBV genomic biomarker.

Clause 26. A method of determining whether a subject suffering from a chronic Hepatitis B virus (HBV) infection will benefit from receiving treatment with an HBV therapeutic, the method comprising:
  (a) performing an assay on a sample obtained from the subject to detect or measure a level of at least one HBV antigen biomarker, at least one HBV genomic biomarker, or at least one HBV antigen marker and at least one HBV genomic biomarker; and (b) determining the likelihood of seroclearance by comparing the level of the at least one HBV antigen biomarker, the at least one HBV genomic biomarker, or the at least one HBV antigen marker and the at least one HBV genomic biomarker to a predetermined level of the at least one HBV antigen biomarker, the at least one HBV genomic biomarker, or the at least one HBV antigen marker and the at least one HBV genomic biomarker;

wherein it is determined that:
(i) the subject will not benefit from an HBV therapeutic if the level of the at least one HBV antigen biomarker, the at least one HBV genomic biomarker, or the at least one HBV antigen marker and the at least one HBV genomic biomarker is unfavorable when compared to the reference level of the at least one HBV antigen biomarker, the at least one HBV genomic biomarker, or the at least one HBV antigen marker and the at least one HBV genomic biomarker; or
(ii) the subject will benefit from an HBV therapeutic if the level of the at least one HBV antigen biomarker, the at least one HBV genomic biomarker, or the at least one HBV antigen marker and the at least one HBV genomic biomarker is favorable than the reference level of the at least one HBV antigen biomarker, the at least one HBV genomic biomarker, or the at least one HBV antigen marker and the at least one HBV genomic biomarker.

Clause 27. The method of clause 25 or 26, wherein the at least one HBV antigen biomarker is selected from the group consisting of Hepatitis B e-antigen (HBeAg), Hepatitis B surface antigen (HBsAg), an isoform of HBsAg, Hepatitis B core antigen (HBcAg), Hepatitis B core antigen (HBcAg), and Hepatitis B core-related antigen (HBcrAg).

Clause 28. The method of clause 25 or 26, wherein the at least one HBV genomic biomarker is selected from the group consisting of HBV RNA, HBV DNA, one or more HBV splice variants, HBV rcDNA, and HBV cccDNA.

Clause 29. The method of any of clauses 25 to 28, wherein the HBV therapeutic is selected from the group consisting of entecavir, lamivudine, adefovir dipivoxil, and interferon alfa-2b.

Clause 30. The method of any of clauses 25 to 29, wherein the assay is performed on a sample that was obtained from about 24 weeks after the subject was infected.

Clause 31. The method of clause 25, wherein if the treatment is not efficacious, the method further comprises altering the treatment with the HBV therapeutic, or ceasing treatment with the HBV therapeutic.

Clause 32. The method of clause 26, wherein the beneficial HBV therapeutic is identified based on whether there is a likelihood of seroclearance or a decreased likelihood of seroclearance.

Clause 33. The method of any of clauses 25 to 32, wherein seroclearance is defined as at least two consecutive determinations, at least 1 year apart, of an HBsAg level of <0.05 IU/mL.

Clause 34. The method of any of clauses 25 to 33, wherein the method further comprises performing an assay on the test sample obtained from the subject to detect or measure a level of at least one of alanine aminotransferase (ALT), and aspartate aminotransferase (AST).

Clause 35. The method of any of clauses 25 to 34, wherein the method further comprises assessing the subject for an independent indicator of a chronic HBV infection.

Clause 36. The method of any one of clauses 3 to 18, wherein the treatment employed by a physican is based on new or recent information in scientific literature and/or reported in clinical trials and is other than that recognized as a standard of care or provided in recommended treatment guidelines to treat a subject having HBV.

Clause 37. The method of any of clauses 3 or 5 to 11, wherein the treatment being administered is an individualized treatment regimen designed or developed for the subject by a clinician based on clinical parameters, cutoffs, publications or a combination thereof.

Clause 38. The method of any of clauses 3 or 5 to 11, wherein the treatment is being administered as part of one or more clinical trial(s) and comprises a treatment regimen designed or developed for one or more subjects based on clinical parameters, cutoffs, clinical parameters and cutoffs obtained from prior clinical trials, patient profiles, publications or a combination thereof.

Clause 39. The method of any one of clauses 1 to 11, wherein the method is repeated until a subject (i) has obtained HBsAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (ii) has obtained HBeAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iii) is negative for HBV DNA for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iv) demonstrates no evidence of liver injury based on ALT and/or AST levels for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; or (v) any combinations of (i)-(iv).

Clause 40. The method of any of clauses 1 to 39, wherein the biomarker is one or more HBV DNA splice variants.

Clause 41. The method of any of clauses 1 to 11 and 24, wherein the one or more markers selected from the group consisting of Hepatitis B e-antigen (HBeAg), Hepatitis B surface antigen (HBsAg), an isoform of HBsAg, Hepatitis B core antigen (HBcAg), HBV DNA, one or more HBV DNA splice variants, HBV RNA, Hepatitis B core-related antigen (HBcrAg), anti-Hepatitis B surface antigen antibody (anti-HBs), anti-Hepatitis B e-antigen antibody (anti-HBe), Hepatitis B surface antigen antibody (anti-HBs) complexes formed between HBsAg and anti-HBs and combinations thereof.

Clause 42. The method of clause 41, wherein the one or more markers further includes alanine aminotransferase (ALT), aspartate aminotransferase (AST) or ALT and AST.

Clause 43. A method of assessing and monitoring disease stage or phase, predicting likelihood of disease progression, or predicting or monitoring response to a Hepatitis B (HBV) therapy, the method comprising the steps of: (a) contacting a test sample obtained from a subject being administered a treatment for HBV or diagnosed with HBV with reagents for detection of the presence, level, or status of one or more markers selected from the group consisting of Hepatitis B e-antigen (HBeAg), Hepatitis B surface antigen (HBsAg), an isoform of HBsAg, Hepatitis B core antigen (HBcAg), HBV DNA, one or more HBV DNA splice variants, HBV RNA, Hepatitis B core-related antigen (HBcrAg), anti-Hepatitis B surface antigen antibody; anti-Hepatitis B surface antigen antibody (anti-HBs), anti-Hepatitis B e-antigen antibody (anti-HBe), anti-Hepatitis B core antigen antibody (anti-HBc) and complexes formed between HBsAg and anti-HBs (also referred to herein as "HBsAg immune complexes"); and (b) assessing and monitoring disease stage or phase, predicting likelihood of disease progression, or predicting or monitoring response to a Hepatitis B (HBV) therapy based on the presence, level, or status of said one or more markers.

Clause 44. A method of detecting the presence, level, or status of one or more markers, comprising: (a) contacting a test sample obtained from a subject being administered a treatment for HBV or diagnosed with HBV with reagents for detection of the presence, level, or status of one or more markers selected from the group consisting of Hepatitis B e-antigen (HBeAg), Hepatitis B surface antigen (HBsAg), an isoform of HBsAg, Hepatitis B core antigen (HBcAg), HBV DNA, one or more HBV splice variants, HBV RNA, Hepatitis B core-related antigen (HBcrAg), anti-Hepatitis B surface antigen antibodyanti-Hepatitis B surface antigen antibody (anti-HBs), anti-Hepatitis B e-antigen antibody (anti-HBe), anti-Hepatitis B core antigen antibody(anti-HBc) and complexes formed between HBsAg and anti-HBs (also referred to herein as "HBsAg immune complexes"); and (b) determining the presence, level, or status of said one or more markers.

Clause 45. A method of treating HBV, comprising: (a) contacting a test sample obtained from a subject diagnosed with HBV with reagents for detection of the presence, level, or status of one or more markers selected from the group consisting of Hepatitis B e-antigen (HBeAg), Hepatitis B surface antigen (HBsAg), an isoform of HBsAg, Hepatitis B core antigen (HBcAg), HBV DNA, one or more HBV splice variants, HBV RNA, Hepatitis B core-related antigen (HBcrAg), anti-Hepatitis B surface antigen antibody (anti-HBs), anti-Hepatitis B e-antigen antibody (anti-HBe), anti-Hepatitis B core antigen antibody(anti-HBc) and complexes formed between HBsAg and anti-HBs (also referred to herein as "HBsAg immune complexes"); (b) identifying a treatment for HBV based on said presence, level, or status of said one or more markers; and (c) administering said treatment.

Clause 46. The method of clauses 43 to 45, wherein the one or more markers further includes alanine aminotransferase (ALT), aspartate aminotransferase (AST) or ALT and AST.

Clause 47. The method of clauses 43 to 44 and 46, wherein said method further comprises administering a treatment for HBV to said subject.

Clause 48. The method of any one of clauses 43 to 47, wherein said treatment is selected from the group consisting of an interferon, a nucleos(t)ide analogue, a nucleic acid, an immunodulator, a core protein assembly inhibitor, an HBsAg release inhibitor, interfering RNA, an entry inhibitor, and a combination thereof.

Clause 49. The method of clause 48, wherein said interferon is selected from the group consisting of interferon alpha-2a and PEGylated interferon alpha-2a.

Clause 50. The method of clause 48, wherein said nucleos(t)ide analogue is selected from the group consisting of lamivudine, adefovir, tenofovir, telbivudine, and entecavir.

Clause 51. The method of clause 48, wherein said nucleic acid is selected from the group consisting of an siRNA, an antisense oligonucleotide, an shRNA, and a miRNA.

Clause 52. The method of clause 48, wherein said core protein assembly inhibitor is selected from the group consisting of NVR 3-1983, GLS4 and BAY 41-4109.

Clause 53. The method of clause 48, wherein said HBsAg release inhibitor is REP 9 AC.

Clause 54. The method of clause 48, wherein said entry inhibitor is Myrcludex-B.

Clause 55. The method of any one of clauses 43 to 54, wherein said reagent is selected from the group consisting of a plurality of nucleic acid primers that specifically hybridize to HBV DNA or RNA, a plurality of nucleic acid probes that specifically hybridize to HBV DNA or RNA, an antibody that specifically binds to an HBV protein, and reagents for enzymatic detection of ALT and/or AST.

Clause 56. The method of any one of clauses 43 to 55, wherein said method further comprises altering said treatment of HBV based on said presence, level, or status of said one or more markers.

Clause 57. The method of clause 56, wherein said altering is selected from the group consisting of starting, stopping, or changing said treatment.

Clause 58. The method of any one of clauses 43 to 57, wherein said one or more markers comprises 3 or more markers.

Clause 59. The method of any one of clauses 43 to 57, wherein said one or more markers comprises 5 or more markers.

Clause 60. The method of any one of clauses 43 to 59, wherein said method further comprises repeating said method one or more times.

Clause 61. The method of any one of clauses 43 to 60, wherein the method is adapted for use in an automated system or semi-automated system.

Clause 62. A kit or system, comprising: reagents for detection of the presence, level, or status of one or more markers selected from the group consisting of Hepatitis B e-antigen (HBeAg), Hepatitis B surface antigen (HBsAg), an isoform of HbsAg, Hepatitis B core antigen (HBcAg), HBV DNA, one or more HBV DNA splice variants, HBV RNA, Hepatitis B core-related antigen (HBcrAg), anti-Hepatitis B surface antigen antibody (anti-HBs), anti-Hepatitis B e-antigen antibody (anti-HBe), anti-Hepatitis B core antigen antibody(anti-HBc), and complexes formed between HBsAg and anti-HBs (also referred to herein as "HBsAg immune complexes").

Clause 63. The kit or system of clause 62, wherein said kit or system further comprises software and a processor for analyzing said presence, level, or status of said one or more markers and providing an assessment of disease stage or phase, a prediction of likelihood of disease progression, or a prediction of a response to a Hepatitis B (HBV) therapy.

Clause 64. The kit or system of clauses 62 or 63, wherein the one or more markers further includes alanine aminotransferase (ALT), aspartate aminotransferase (AST) or ALT and AST.

Clause 65. The kit or system of any of clauses 62 to 64, wherein said reagent is selected from the group consisting of a plurality of nucleic acid primers that specifically hybridize to HBV DNA or RNA, a plurality of nucleic acid probes that specifically hybridize to HBV DNA or RNA, an antibody that specifically binds to an HBV protein, and reagents for enzymatic detection of ALT and/or AST.

Clause 66. The kit of any one of clauses 62 to 65, wherein said one or more markers comprises 3 or more markers.

Clause 67. The kit or system of any one of clauses 62 to 65, wherein said one or more markers comprises 5 or more markers.

Clause 68. The use of reagents for detection of the presence, level, or status of one or more markers selected from the group consisting of Hepatitis B e-antigen (HBeAg), Hepatitis B surface antigen (HBsAg), an isoform of HbsAg, Hepatitis B core antigen (HBcAg), HBV DNA, one or more HBV DNA splice variants, HBV RNA, Hepatitis B core-related antigen (HBcrAg), anti-Hepatitis B surface antigen antibody (anti-HBs), anti-Hepatitis B e-antigen antibody (anti-HBe), anti-Hepatitis B core antigen antibody(anti-HBc), and complexes formed between HBsAg and anti-HBs (also referred to herein as "HBsAg immune complexes") to provide an assessment of disease stage or phase, a prediction of likelihood of disease progression, or a prediction of a response to a Hepatitis B (HBV) therapy.

Clause 69. The use of clause 68, wherein the one or more markers further includes alanine aminotransferase (ALT), aspartate aminotransferase (AST) or ALT and AST.

Clause 70. The method of any of clauses 45 to 61, wherein the treatment employed by a physician is based on new or recent information in scientific literature and/or reported in clinical trials and is other than that recognized as a standard of care or provided in recommended treatment guidelines to treat a subject having HBV.

Clause 71. The method of any of clauses 45, 46 or 48 to 61, wherein the treatment being administered is an individualized treatment regimen designed or developed for the subject by a clinician based on clinical parameters, cutoffs, publications or a combination thereof Clause 72. The method of any of clauses 45, 46 or 48 to 61, wherein the treatment is being administered as part of one or more clinical trial(s) and comprises a treatment regimen designed or developed for one or more subjects based on clinical parameters, cutoffs, clinical parameters and cutoffs obtained from prior clinical trials, patient profiles, publications or a combination thereof.

Clause 73. The method of any one of clauses 43 to 61 or 68, wherein the method is repeated until a subject (i) has obtained HBsAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (ii) has obtained HBeAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iii) is negative for HBV DNA for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iv) demonstrates no evidence of liver injury based on ALT and/or AST levels for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; or (v) any combinations of (i)-(iv).

Clause 74. A method of assessing and monitoring disease stage or phase, predicting likelihood of disease progression, or predicting or monitoring response to a Hepatitis B (HBV) therapy, the method comprising the steps of:
  (a) contacting a test sample obtained from a subject being administered a treatment for HBV or diagnosed with HBV with reagents for detection of the presence, level, or status of one or more markers selected from the group consisting of an isoform of HBsAg, HBV DNA, one or more HBV splice variants, HBV RNA, and anti-Hepatitis B surface antigen antibody (anti-HBs) complexes formed between HBsAg and anti-HBs; and
  (b) assessing and monitoring disease stage or phase, predicting likelihood of disease progression, or predicting or monitoring response to a Hepatitis B (HBV) therapy based on the presence, level, or status of said one or more markers.

Clause 75. A method of detecting the presence, level, or status of one or more markers, comprising:
  (a) contacting a test sample obtained from a subject being administered a treatment for HBV or diagnosed with HBV with reagents for detection of the presence, level, or status of one or more markers selected from the group consisting of an isoform of HBsAg, HBV DNA, one or more HBV splice variants, HBV RNA, and anti-Hepatitis B surface antigen antibody (anti-HBs) complexes formed between HBsAg and anti-HBs; and
  (b) determining the presence, level, or status of said one or more markers.

Clause 76. A method of treating HBV, comprising:
  (a) contacting a test sample obtained from a subject diagnosed with HBV with reagents for detection of the presence, level, or status of one or more markers selected from the group consisting of an isoform of HBsAg, HBV DNA, one or more HBV splice variants, HBV RNA, and anti-Hepatitis B surface antigen antibody (anti-HBs) complexes formed between HBsAg and anti-HBs.
  (b) identifying a treatment for HBV based on said presence, level, or status of said one or more markers; and
  (c) administering said treatment.

Clause 77. The method of any one of clauses 74 to 76, wherein the at least one biomarker is HBV RNA.

Clause 78. The method of any one of clauses 74 to 77, wherein the at least one biomarker is HBV DNA.

Clause 79. The method of any one of clauses 74 to 78, wherein the at least one biomarker is at least one splice variant of HBV DNA.

Clause 80. The method of any one of clauses 74 to 79, wherein the at least one biomarker is an isoform of HBsAg.

Clause 81. The method of any one of clauses 74 to 80, wherein the at least one biomarker is anti-Hepatitis B surface antigen antibody (anti-HBs) complexes formed between HBsAg and anti-HBs.

Clause 82. The method of any one of clauses 74 to 75 and 77-81, wherein said method further comprises administering a treatment for HBV to said subject.

Clause 83. The method of any one of clauses 76-82, wherein said treatment is selected from the group consisting of an interferon, a nucleos(t)ide analogue, a nucleic acid, an immunodulator, a core protein assembly inhibitor, an HBsAg release inhibitor, an entry inhibitor, interfering RNA and a combination thereof.

Clause 84. The method of clause 83, wherein said interferon is selected from the group consisting of interferon alpha-2a and PEGylated interferon alpha-2a.

Clause 85. The method of clause 83, wherein said nucleos(t)ide analogue is selected from the group consisting of lamivudine, adefovir, tenofovir, telbivudine, and entecavir.

Clause 86. The method of clause 83, wherein said nucleic acid is selected from the group consisting of an siRNA, an antisense oligonucleotide, an shRNA, and a miRNA.

Clause 87. The method of clause 83, wherein said core protein assembly inhibitor is selected from the group consisting of NVR 3-1983, GLS4 and BAY 41-4109.

Clause 88. The method of clause 83, wherein said HBsAg release inhibitor is REP 9 AC.

Clause 89. The method of clause 83, wherein said entry inhibitor is Myrcludex-B.

Clause 90. The method of any one of clauses 74 to 89, wherein said reagent is selected from the group consisting of a plurality of nucleic acid primers that specifically hybridize to HBV DNA or RNA, a plurality of nucleic acid probes that specifically hybridize to HBV DNA or RNA, an antibody that specifically binds to an HBV protein, and reagents for enzymatic detection of ALT and/or AST.

Clause 91. The method of any one of clauses 74 to 90, wherein said method further comprises altering said treatment of HBV based on said presence, level, or status of said one or more markers.

Clause 92. The method of clause 91, wherein said altering is selected from the group consisting of starting, stopping, or changing said treatment.

Clause 93. The method of any one of clauses 74 to 92, wherein said one or more markers comprises 3 or more markers.

Clause 94. The method of any one of clauses 74 to 93, wherein said one or more markers comprises 5 markers.

Clause 95. The method of any one of clauses 74 to 94, wherein said method further comprises repeating said method one or more times.

Clause 96. The method of any one of clauses 74 to 95, wherein the method is adapted for use in an automated system or semi-automated system.

Clause 97. A kit or system, comprising:
reagents for detection of the presence, level, or status of one or more markers selected from the group consisting of an isoform of HBsAg, HBV DNA, one or more HBV splice variants, HBV RNA, and anti-Hepatitis B surface antigen antibody (anti-HBs) complexes formed between HBsAg and anti-HBs.

Clause 98. The kit or system of clause 97, wherein the at least one biomarker is HBV RNA.

Clause 99. The kit or system of any one of clauses 97 or 98, wherein the at least one biomarker is HBV DNA.

Clause 100. The kit or system of any one of clauses 97 to 99, wherein the at least one biomarker is at least one splice variant of HBV DNA.

Clause 101. The kit or system of any one of clauses 97 to 100, wherein the at least one biomarker is an isoform of HBsAg.

Clause 102. The kit or system of any one of clauses 97 to 101, wherein the at least one biomarker is anti-Hepatitis B surface antigen antibody (anti-HBs) complexes formed between HBsAg and anti-HBs.

Clause 103. The kit or system of any one of clauses 97 to 102, wherein said kit or system further comprises software and a processor for analyzing said presence, level, or status of said one or more markers and providing an assessment of disease stage or phase, a prediction of likelihood of disease progression, or a prediction of a response to a Hepatitis B (HBV) therapy.

Clause 104. The kit or system of clauses 97 to 103, wherein said reagent is selected from the group consisting of a plurality of nucleic acid primers that specifically hybridize to HBV DNA or RNA, a plurality of nucleic acid probes that specifically hybridize to HBV DNA or RNA, an antibody that specifically binds to an HBV protein, and reagents for enzymatic detection of ALT and/or AST.

Clause 105. The kit of any one of clauses 97 to 104, wherein said one or more markers comprises 3 or more markers.

Clause 106. The kit or system of any one of clauses 97 to 104, wherein said one or more markers comprises 5 markers.

Clause 107. The use of reagents for detection of the presence, level, or status of one or more markers selected from the group consisting of an isoform of HBsAg, HBV DNA, one or more HBV splice variants, HBV RNA, and anti-Hepatitis B surface antigen antibody (anti-HBs) complexes formed between HBsAg and anti-HBs to provide an assessment of disease stage or phase, a prediction of likelihood of disease progression, or a prediction of a response to a Hepatitis B (HBV) therapy.

Clause 108. The use of clause 107, wherein the at least one biomarker is HBV RNA.

Clause 109. The use of any one of clauses 107 or 108, wherein the at least one biomarker is HBV DNA.

Clause 110. The use of any one of clauses 107 to 109, wherein the at least one biomarker is at least one splice variant of HBV DNA.

Clause 111. The use of any one of clauses 107 to 110, wherein the at least one biomarker is an isoform of HBsAg.

Clause 112. The use of any one of clauses 107 to 111, wherein the at least one biomarker is anti-Hepatitis B surface antigen antibody (anti-HBs) complexes formed between HBsAg and anti-HBs.

Clause 113. The method of any of clauses 76 to 96, wherein the treatment employed by a physician is based on new or recent information in scientific literature and/or reported in clinical trials and is other than that recognized as a standard of care or provided in recommended treatment guidelines to treat a subject having HBV.

Clause 114. The method of any of clauses 76 or 83 to 89, wherein the treatment being administered is an individualized treatment regimen designed or developed for the subject by a clinician based on clinical parameters, cutoffs, publications or a combination thereof.

Clause 115. The method of any of clauses 76 or 83 to 89, wherein the treatment is being administered as part of one or more clinical trial(s) and comprises a treatment regimen designed or developed for one or more subjects based on clinical parameters, cutoffs, clinical parameters and cutoffs obtained from prior clinical trials, patient profiles, publications or a combination thereof.

Clause 116. The method of any one of clauses 74 to 96 or 107 to 112, wherein the method is repeated until a subject (i) has obtained HBsAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (ii) has obtained HBeAg loss for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iii) is negative for HBV DNA for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; (iv) demonstrates no evidence of liver injury based on ALT and/or AST levels for a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years; or (v) any combinations of (i)-(iv).

Clause 117. A method of determining whether a subject suffering from a chronic Hepatitis B virus (HBV) infection will benefit from receiving treatment with an HBV therapeutic, the method comprising:
 (a) performing an assay on a sample obtained from the subject to detect or measure a level of at least one HBV antigen biomarker, at least one HBV genomic biomarker, or at least one HBV antigen marker and at least one HBV genomic biomarker; and
 (b) comparing the level of the at least one HBV antigen biomarker, the at least one HBV genomic biomarker, or the at least one HBV antigen marker and the at least one HBV genomic biomarker to a predetermined level of the at least one HBV antigen biomarker, the at least one HBV genomic biomarker, or the at least one HBV antigen marker and the at least one HBV genomic biomarker;
wherein it is determined that:
 (i) the subject will not benefit from an HBV therapeutic if the level of the at least one HBV antigen biomarker, the at least one HBV genomic biomarker, or the at least one HBV antigen marker and the at least one HBV genomic biomarker is unfavorable when compared to the reference level of the at least one HBV antigen biomarker, the at least one HBV genomic biomarker, or the at least one HBV antigen marker and the at least one HBV genomic biomarker; or
 (ii) the subject will benefit from an HBV therapeutic if the level of the at least one HBV antigen biomarker, the at least one HBV genomic biomarker, or the at least one HBV antigen marker and the at least one HBV genomic biomarker is favorable than the reference level of the at least one HBV antigen biomarker, the at least one HBV genomic biomarker, or the at least one HBV antigen marker and the at least one HBV genomic biomarker.

Clause 118. The method of clause 117, wherein the at least one HBV antigen biomarker is selected from the group consisting of Hepatitis B e-antigen (HBeAg), Hepatitis B surface antigen (HBsAg), an isoform of HBsAg, Hepatitis B core antigen (HBcAg), Hepatitis B core antigen (HBcAg), and Hepatitis B core-related antigen (HBcrAg).

Clause 119. The method of clause 117, wherein the at least one HBV genomic biomarker is selected from the group consisting of HBV RNA, HBV DNA, one or more HBV DNA splice variants, HBV rcDNA, and HBV cccDNA.

Clause 120. The method of clause 117, wherein the HBV therapeutic is selected from the group consisting of entecavir, lamivudine, adefovir dipivoxil, and interferon alfa-2b.

Clause 121. The method of any of clauses 117 to 120, wherein the assay is performed on a sample that was obtained from about 24 weeks after the subject was infected.

Clause 122. The method of clause 117, wherein the subject is determined to benefit from a HBV therapeutic.

What is claimed is:

1. A method comprising the steps of:
(a) receiving an indication of presence, level, or status of at least two markers obtained from an assay using a test sample obtained from a subject being administered a treatment for Hepatitis B Virus (HBV) or diagnosed with HBV, wherein the at least two markers are and aspartate aminotransferase (AST); and
(b) (1) assessing and monitoring disease stage or phase, or monitoring response to a HBV therapy based on the presence, level, or status of the at least two markers; or
(2) (i) identifying a treatment for HBV based on said presence, level, or status of the at least two markers, wherein said treatment is selected from the group consisting of: (aa) an interferon, a nucleoside analogue, a nucleotide analogue, a nucleic acid, an immunodulator, a core protein assembly inhibitor, an HBsAg release inhibitor, an entry inhibitor, interfering RNA, and a combination thereof; (bb) a treatment employed by a physician is based on new or recent information in scientific literature and/or reported in clinical trials and is other than that recognized as a standard of care or provided in recommended treatment guidelines to treat a subject having HBV; (cc) a treatment being administered as an individualized treatment regimen designed or developed for the subject by a clinician based on clinical parameters, cutoffs, publications or a combination thereof; and (dd) a treatment being administered as part of one or more clinical trial(s) and comprises a treatment regimen designed or developed for one or more subjects based on clinical parameters, cutoffs, clinical parameters and cutoffs obtained from prior clinical trials, patient profiles, publications or a combination thereof; and
(ii) administering said treatment if it is determined that the subject will benefit from an HBV therapeutic if the level of the at least two markers is favorable when compared to a predetermined or reference level of said at least two markers or not administering said treatment if it is determined that the subject will not benefit from an HBV therapeutic if the level of the at least two markers is unfavorable when compared to the predetermined or reference level of the at least two markers.

2. The method of claim 1,
wherein said:
(a) interferon is selected from the group consisting of interferon alpha-2a and PEGylated interferon alpha-2a;
(b) nucleoside analogue is selected from the group consisting of lamivudine, adefovir, tenofovir, telbivudine, and entecavir;
(c) nucleic acid is selected from the group consisting of an siRNA, an antisense oligonucleotide, an shRNA, and a miRNA,
(d) core protein assembly inhibitor is selected from the group consisting of NVR 3-1983, GLS4 and BAY 41-4109;
(e) HBsAg release inhibitor is REP 9 AC;
(f) entry inhibitor is Myrcludex-B; or
(g) nucleoside analogue is selected from the group consisting of lamivudine, adefovir, tenofovir, telbivudine, and entecavir.

3. A kit or system, comprising:
reagents for detection of the presence, level, or status of at least two markers, wherein the at least two markers are: Hepatitis B core-related antigen (HBcrAg), and aspartate aminotransferase (AST).

4. The kit or system of claim 3, wherein said reagent is for enzymatic detection of AST.

5. A method comprising the steps of:
(a) receiving an indication of presence, level, or status of one or more markers obtained from an assay using a test sample obtained from a subject being administered a treatment for Hepatitis B Virus (HBV) or diagnosed with HBV, wherein the one or more markers are selected from the group consisting of Hepatitis B core-related antigen (HBcrAg), and aspartate aminotransferase (AST); and
(b) (1) assessing and monitoring disease stage or phase or monitoring response to a HBV therapy based on the presence, level, or status of said one or more markers; or
(2) (i) identifying a treatment for HBV based on said presence, level, or status of said one or more markers, wherein said treatment is selected from the group consisting of: (aa) an interferon, a nucleoside analogue, a nucleotide analogue, a nucleic acid, an immunodulator, a core protein assembly inhibitor, an HBsAg release inhibitor, an entry inhibitor, interfering RNA, and a combination thereof; (bb) a treatment employed by a physician is based on new or recent information in scientific literature and/or reported in clinical trials and is other than that recognized as a standard of care or provided in recommended treatment guidelines to treat a subject having HBV; (cc) a treatment being administered as an individualized treatment regimen designed or developed for the subject by a clinician based on clinical parameters, cutoffs, publications or a combination thereof; and (dd) a treatment being administered as part of one or more clinical trial(s) and comprises a treatment regimen designed or developed for one or more subjects based on clinical parameters, cutoffs, clinical parameters and cutoffs obtained from prior clinical trials, patient profiles, publications or a combination thereof; and
(ii) administering said treatment if it is determined that the subject will benefit from an HBV therapeutic if the level of the one or more markers is favorable when compared to a predetermined or reference level of said one or more markers or not administering said treatment if it is determined that the subject will not benefit from an HBV therapeutic if the level of the one or more markers is unfavorable when compared to the predetermined or reference level of the one or more markers.

6. The method of claim 5,
wherein said:
(a) interferon is selected from the group consisting of interferon alpha-2a and PEGylated interferon alpha-2a;
(b) nucleoside analogue is selected from the group consisting of lamivudine, adefovir, tenofovir, telbivudine, and entecavir;
(c) nucleic acid is selected from the group consisting of an siRNA, an antisense oligonucleotide, an shRNA, and a miRNA,
(d) core protein assembly inhibitor is selected from the group consisting of NVR 3-1983, GLS4 and BAY 41-4109;
(e) HBsAg release inhibitor is REP 9 AC;
(f) entry inhibitor is Myrcludex-B; or (g) nucleoside analogue is selected from the group consisting of lamivudine, adefovir, tenofovir, telbivudine, and entecavir.

\* \* \* \* \*

UNITED STATES PATENT AND TRADEMARK OFFICE
CERTIFICATE OF CORRECTION

PATENT NO. : 12,235,273 B2
APPLICATION NO. : 17/052685
DATED : February 25, 2025
INVENTOR(S) : Gavin A. Cloherty et al.

Page 1 of 1

It is certified that error appears in the above-identified patent and that said Letters Patent is hereby corrected as shown below:

In the Claims

Claim 1, Column 99, Line 13 reads:
"with HBV, wherein the at least two markers are and;"

Whereas it should read:
-- with HBV, wherein the at least two markers are Hepatitis B core-related antigen (HBcrAg) and; --

Signed and Sealed this
Ninth Day of September, 2025

Coke Morgan Stewart
*Acting Director of the United States Patent and Trademark Office*